(12) United States Patent
Stromgaard et al.

(10) Patent No.: US 7,473,788 B2
(45) Date of Patent: Jan. 6, 2009

(54) **ANALOGS OF TERPENE TRILACTONES FROM *GINKGO BILOBA* AND RELATED COMPOUNDS AND USES THEREOF**

(75) Inventors: Kristian Stromgaard, New York, NY (US); Makiko Suehiro, White Plains, NY (US); Koji Nakanishi, New York, NY (US); Stine B. Vogensen, Copenhagen N (DK)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 11/634,429

(22) Filed: Dec. 5, 2006

(65) Prior Publication Data

US 2007/0098632 A1     May 3, 2007

Related U.S. Application Data

(63) Continuation of application No. 10/401,931, filed on Mar. 28, 2003, now Pat. No. 7,145,021, which is a continuation-in-part of application No. 10/109,965, filed on Mar. 29, 2002, now Pat. No. 6,693,091.

(60) Provisional application No. 60/436,916, filed on Dec. 27, 2002.

(51) Int. Cl.
    *C07D 305/14*   (2006.01)
    *A01K 43/12*    (2006.01)

(52) U.S. Cl. ........................ 549/265; 514/443

(58) Field of Classification Search ................. 549/265; 514/443
    See application file for complete search history.

(56) References Cited

U.S. PATENT DOCUMENTS

| | | | |
|---|---|---|---|
| 4,981,688 | A | 1/1991 | Ayroles et al. |
| 5,389,370 | A | 2/1995 | O'Reilley et al. |
| 5,399,348 | A | 3/1995 | Schwabe |
| 5,466,829 | A | 11/1995 | Park et al. |
| 5,512,286 | A | 4/1996 | Schwabe |
| 5,541,183 | A | 7/1996 | Park et al. |
| 5,599,950 | A | 2/1997 | Teng |
| 6,030,621 | A | 2/2000 | DeLong et al. |
| 6,117,431 | A | 9/2000 | Ramazanov et al. |
| 6,143,725 | A | 11/2000 | Vasella et al. |
| 6,174,531 | B1 | 1/2001 | Zhang et al. |
| 6,187,314 | B1 | 2/2001 | Xie et al. |
| 6,221,356 | B1 | 4/2001 | Junsheng |

(Continued)

FOREIGN PATENT DOCUMENTS

DE          2117429         10/1972

(Continued)

OTHER PUBLICATIONS

Jaracz et al. Journal of Organic Chemistry, 67, 4623-, 2002.*

(Continued)

*Primary Examiner*—D. Margaret Seaman
*Assistant Examiner*—Nizal S Chandrakumar
(74) *Attorney, Agent, or Firm*—John P. White; Cooper & Dunham LLP

(57) ABSTRACT

The subject invention provides compounds having the structure:

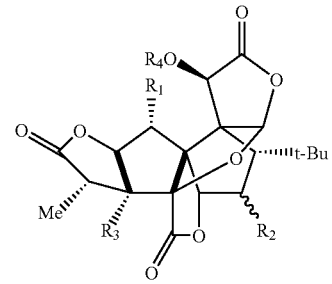

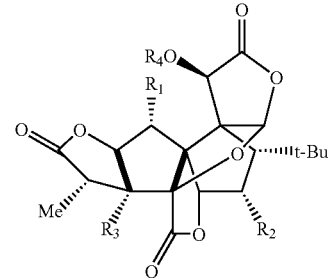

wherein $R_1$ is H, OH, a photoactivatable moiety, a fluorescent moiety, or a radioactive moiety; $R_2$ is H, OH, a photoactivatable moiety, a fluorescent moiety, or a radioactive moiety; $R_3$ is H or OH; $R_4$ is H, OH, a photoactivatable moiety, a fluorescent moiety, or a radioactive moiety; and wherein at least one of $R_1$, $R_2$, $R_3$, or $R_4$ is a photoactivatable moiety, a fluorescent moiety, or a radioactive moiety, or an optically pure enantiomer of the compound or wherein R1 is H or OH; R2 is H, OH, halogen, unsubstituted or substituted, straight or branched ($C_1$-$C_5$) alkyl group, ($C_2$-$C_5$) alkenyl, or a ($C_2$-$C_5$) alkynyl, ($C_1$-$C_5$) alkoxy, ($C_2$-$C_5$) alkenyloxy, or ($C_2$-$C_5$) alkynyloxy, —N3, —COR5, —CONR5R6, —CO2R5, —OCOR5, —NH(OH), —NR5R6, —NHCOR5, —N(OH)COR5, —CH2OR5, —OCH2CO2R5, —CH2SR5, —CH2NR5R6, —SR5, —OSR5, or —NR5SO2R6, where R5 and R6 are each independently hydrogen, substituted or unsubstituted ($C_1$-$C_5$) alkyl, ($C_2$-$C_5$) alkenyl, or ($C_2$-$C_5$) alkynyl, or a cycloalkyl or aryl group having 3 to 10 carbon atoms; R3 is H or OH; R4 is H, (C1-C10) alkyl, (C1-C10) alkenyl, (C1-C10) alkynyl, -A-Ar, -A-Z-Ar, —SO2—Ar, or -A-NR5, or —R7, where A, Z and Ar are as defined herein, and the use of the compounds for detecting or identifying a receptor which binds the compounds of the invention or for treating a PAF associated condition in a subject.

19 Claims, 8 Drawing Sheets

U.S. PATENT DOCUMENTS

| | | | |
|---|---|---|---|
| 6,274,621 | B1 | 8/2001 | Drieu |
| 6,328,999 | B1 | 12/2001 | Schwabe et al. |
| 6,590,109 | B2 | 7/2003 | Lichtblau et al. |
| 6,693,091 | B2 | 2/2004 | Stromgaard et al. |
| 6,844,451 | B2 | 1/2005 | Lichtblau et al. |
| 7,145,021 | B2 | 12/2006 | Stromgaard et al. |
| 2003/0194370 | A1 | 10/2003 | Stromgaard et al. |
| 2003/0225052 | A1 | 12/2003 | Stromgaard et al. |
| 2005/0119336 | A1 | 6/2005 | Nakanishi et al. |
| 2005/0136136 | A1 | 6/2005 | Lichtblau et al. |
| 2008/0108837 | A1 | 5/2008 | Nakanishi et al. |

FOREIGN PATENT DOCUMENTS

| | | |
|---|---|---|
| GB | 2288599 | 11/1995 |
| WO | WO 9302204 | 2/1993 |
| WO | WO 9952911 | 10/1999 |
| WO | WO 02083158 | 10/2002 |
| WO | WO 03006040 | 1/2003 |
| WO | WO 03082185 | 10/2003 |
| WO | WO 2005021496 | 3/2005 |
| WO | WO 2005046829 | 5/2005 |
| WO | WO 2005092324 | 10/2005 |
| WO | WO 2006/083366 | 8/2006 |
| WO | WO 2006083366 | 8/2006 |
| WO | WO 07002410 | 1/2007 |
| WO | WO 2007/002410 | 12/2007 |

OTHER PUBLICATIONS

Corey, E. J. & Su, W. G. (1987) *J. Am. Chem. Soc.* 109, 7534-7536.
Corey, E. J., Kang, M. C., Desai, M. C., Ghosh, A. K., & Houpis, I. N. (1988) *J. Am. Chem. Soc.* 110, 649-651.
Corey, E. J. & Ghosh, A. K. (1988) *Tetrahedron Lett.*. 29, 3205-3206.
Corey, E.J. & Gavai, A. V. (1989) *Tetrahedron Lett.* 30 6959-6962.
Corey, E.J. & Rao, K. S. (1991) *Tetrahedron Lett.* 32 4623-4626.
Ahlemeyer, B. et al. (2003) PMID: 13130383.
Jaracz et al. (2002) *J. Org. Chem* 67 (13): pp. 4623-2626.
Lang, Q. et al. (2001) *Talanta* 54:673-680.
Hu, L., Chen, Z., Cheng, X., & Xie, Y. (1999) *Pure Appl. Chem.* 71, 1153-1156.
Hu, L., Chen, Z., Xie, Y., Jiang, H., & Zhen, H. (2000) *Bioorg. Med. Chem.* 8, 1515-1521.
Hu, L., Chen, Z., Xie, Y., Jiang, Y., & Zhen, H. (2000) *J. Asian Nat. Prod. Res.* 2, 103-110.
Hu, L., Chen, Z., & Xie, Y. (2001) *J. Asian Nat. Prod. Res.* 3, 219-227.
McKenna, D.J. et al., (2001) Efficacy, Safety and Use of Gingko Biloba in Clinical and Preclinical Applications, Abstract; *Altern. Ther. Health. Med.*, 7(5):70.
Supplementary European Search Report issued Sep. 30, 2005 in connection with Application No. 02748132.4.
International Search Report issued Sep. 12, 2002 in connection with PCT/US02/22101.
International Search Report issued on Sep. 2, 2003 in connection with Application No. PCT/US03/12651.
International Search Report issued Mar. 17, 2005 in connection with Application No. PCT/US04/27671.
International Search Report issued Jun. 8, 2005 in connection with Application No. PCT/US04/037412.
International Search Report issued Jan. 3, 2007 in connection with Application No. PCT/US06/24492.
International Preliminary Examination Report issued Apr. 21, 2003 in connection with PCT/US02/22101.
Written Opinion of the International Searching Authority issued by the International Searching Authority (ISA/US) on Jun. 8, 2005 in connection with Application No. PCT/US04/037412.
Tanaka, K. et al. (2005) "Unique Reactivity of α-Alkoxy Ginkgolide Lactones to Nucleophilic Reagents: Preparation of New Lactol Derivatives", *Bull. Chem. Soc. Jpn.*, 78:1843-1850.
Tanaka, K. et al. (2005) "Preparation of Ginkgolide and F-seco-ginkgolide Lactols: the Unique Reactivity of α-hydroxy Lactones toward $NaBH_4$,", Tetrahedron Letters, 46:531-534.
Vogensen, S.B. et al. (2003) "Preparation of 7-Substituted Ginkgolide Derivatives: Potent Platelet Activating Factor (PAF) Receptor Antogonists", *J. Med. Chem.*, 46:601-608.
International Search Report issued on Mar. 22, 2007 in connection with PCT/US05/42647.
Written Opinion of the International Searching Authority issued on Mar. 22, 2007 in connection with PCT/US05/42647.
Non-final Office Action issued Jan. 6, 2006 in connection with U.S. Appl. No. 10/925,209.
Non-final Office Action issued Apr. 24, 2006 in connection with U.S. Appl. No. 10/925,209.
Non-final Office Action issued Oct. 17, 2006 in connection with U.S. Appl. No. 10/925,209.
Non-final Office Action issued Aug. 2, 2007 in connection with U.S. Appl. No. 10/925,209.
Notice of Allowance issued May 22, 2008 in connection with U.S. Appl. No. 10/925,209.
U.S. Appl. No. 09/903,049, filed Jul. 11, 2001, Dirk Lichtblau et al.
U.S. Appl. No. 11/791,422, filed Nov. 23, 2005, Koji Nakanishi et al.
International Search Report issued Jan. 3, 2007 in PCT International Publication No. WO 2007/002410.
Written Opinion issued Mar. 22, 2007 in connection with PCT International Publication No. WO 2006/083366.
International Preliminary Examination Report issued on May 30, 2007 in connection with PCT International Publication No. WO 2006/083366.
Office Action issued Jan. 10, 2008 in connection with U.S. Appl. No. 10/925,209.
Notification Concerning Transmittal of Copy of International Preliminary Report on Patentability issued Jan. 10, 2008 in connection with PCT International Application No. PCT/US2006/024492.

\* cited by examiner

Bilobalide (BB, 6)

| | $R_1$ | $R_2$ | $R_3$ |
|---|---|---|---|
| Ginkgolide A (GA 1) | H | H | OH |
| Ginkgolide B (GB, 2) | OH | H | OH |
| Ginkgolide C (GC, 3) | OH | OH | OH |
| Ginkgolide J (GJ, 4) | H | OH | OH |
| Ginkgolide M (GM, 5) | OH | OH | H |

WEB 2086

PAF (n = 11-13)

ANALOGS OF TERPENE TRILACTONES FROM *GINKGO BILOBA* AND RELATED COMPOUNDS AND USES THEREOF

This application is a continuation of U.S. Ser. No. 10/401,931, filed Mar. 28, 2003, now U.S. Pat. No. 7,145,021, issued Dec. 5, 2006, which is a continuation-in-part of U.S. Ser. No. 10/109,965, filed Mar. 29, 2002, now U.S. Pat. No. 6,693,091, issued Feb. 17, 2004, and also claims the benefit of U.S. Provisional Application No. 60/436,916, filed Dec. 27, 2002, the entire contents of each of which are hereby incorporated by reference.

Throughout this application, various publications are referenced by the first author's last name and the year of publication in parenthesis. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

*Ginkgo biloba* L., the last surviving member of a family of trees (Ginkgoacea) that appeared more than 250 million years ago, has been mentioned in the Chinese Materia Medica for more than 2,500 years (Drieu, 2000). A number of *G. biloba* natural products have been isolated (Hasler, 2000), the most unique being the terpene trilactones, i.e. ginkgolides A, B, C, J and M (1-5) and bilobalide (6) (FIG. 1) (Nakanishi, 1967; Okabe, 1967; Nakanishi, 1971; Weinges, 1987). The ginkgolides are diterpenes with an aesthetic cage skeleton consisting of six 5-membered rings, i.e., a spiro[4.4]nonane carbocycle, three lactones and a tetrahydrofuran. The difference between the five ginkgolides lies in the variation in the number and positions of hydroxyl groups on the spirononane framework (FIG. 1).

A standardized *G. biloba* extract (EGb 761) containing terpene trilactones (5-7%) and flavonoids (22-24%) has demonstrated neuromodulatory properties (DeFeudis, 2000), and several clinical studies using EGb 761 have reported positive effects on various neurodegenerative diseases (Logani, 2000; Oken, 1998; Kleijnen, 1992; Søholm, 1998; Diamond, 2000; van Dongen, 2000), including Alzheimer's disease (AD). In two studies involving a total of 549 AD patients, EGb 761 significantly slowed the loss of cognitive symptoms of dementia, with an efficacy in between donezepil (Aricept®) and rivastigmine (Exelon®), the two currently marketed drugs for treatment of AD symptoms (Le Bars, 1997; Kanowski, 1996). Moreover, a recent study by Schultz and co-workers found that EGb 761 upregulated several genes in rat hippocampus and cortex, including genes expressing proteins such as transthyretin and neuronal tyrosine/threonine phosphatase, both of which are believed to be involved in AD (Watanabe, 2001). Several recent studies on healthy volunteers have shown positive effects of EGb 761 on short-term working memory (Kennedy, 2000; Polich, 2001; Rigney, 1999; Stough, 2001) indicating that constituents of *G. biloba* also influence the brain under physiological conditions.

Although the molecular basis for the action of *G. biloba* terpene trilactone constituents on the central nervous system (CNS) is only poorly understood, it is known that the ginkgolides, particularly ginkgolide B (GB, 2), is a potent in vitro antagonist of the platelet-activating factor receptor (PAFR) (Braquet, 1985).

A number of *G. biloba* constituents have been isolated, including the unique terpene trilactones, i.e., ginkgolides A, B, C, J and M and bilobalide (Nakanishi, 1967; Okabe, 1967; Nakanishi, 1971; Weinges, 1987). Ginkgolides are diterpenes with a cage skeleton consisting of six 5-membered rings, the difference between the five ginkgolides being in the variation in the number and positions of hydroxyl groups on the spirononane framework. Although the molecular basis for the action of *G. biloba* terpene trilactone constituents in the central nervous system (CNS) is only poorly understood, it is known that ginkgolides, particularly ginkgolide B (GB, 1, FIG. 1), is a potent in vitro antagonist of the platelet-activating factor receptor (PAFR) (Braquet, 1987; Braquet, 1991). The PAFR is a potential target for neurodegenerative diseases (Singh, 2001) such as senile dementia (http://www.herbs.org/greenpapers/ginkgo.htm), stroke (Lindsberg, 1990) and nerve cell damage due to ischemia (Krieglstein, 1994).

PAF (1-O-alkyl-2-acetyl-sn-glycero-3-phosphocholine, FIG. 2) is a phospholipid mediator involved in numerous disorders. PAF (1-O-alkyl-2-acetyl-sn-glycero-3-phosphocholine) has been suggested as a retrograde messenger in long-term potentiation (LTP) (Kato, 1994), thus indicating the importance of the PAFR as a target for ginkgolides. PAF has been implicated in a number of immunological, inflammatory and vascular disorders (Chung, 1995) including asthma (Nagase, 2002) and endotoxic shock (Tsuneyuki, 1996). In the latter case, PAFR antagonists have been shown to attenuate the effects of endotoxic shock in rats. Hyperacute rejections arising from PAF-associated reactions of either xenoperfusion (Cruzado, 1997) or renal transplants (Grino, 1994) have been found to be preventable by PAFR antagonists. In a separate study, PAFR antagonists significantly prevented pulmonary edema after myocardial ischemia in dogs (Taniguchi, 1992). The role PAF plays in a broad range of physiological conditions appears well-documented given the above examples, underscoring the importance of PAFR antagonists in inhibiting their undesirable effects.

These effects are manifested through binding of PAF to the PAFR, a G protein-coupled receptor that is found in organs such as the lungs, liver, kidneys (Ishii, 2000; Prescott, 2000; Shukla, 1996), and brain (Bito, 1992; Mori, 1996). The function of PAF in the brain is still not clear, although PAF has been suggested to play a role in diseases of aging (Kroegel, 1992), and in initiating HIV-related neuropathogenesis (Perry, 1998).

With few exceptions previous structure-activity relationship (SAR) studies of terpene trilactones on the PAFR have focused almost entirely on derivatives of GB (2). In all cases the derivatives were evaluated for their ability to prevent PAF-induced aggregation of rabbit platelets. Corey et al. investigated various intermediates encountered in the total syntheses of ginkgolide A (GA, 1) (Corey, 1988), GB (2) (Corey, 1988) and bilobalide (BB, 6) (Corey, 1987), and found that although the terminal methyl-bearing lactone was not essential for activity and could be replaced by other lipophilic groups (Corey, 1989), the tert. butyl group was important for PAFR antagonism (Corey, 1991). Park et al. synthesized over 200 derivatives of GB (2), with particular focus on aromatic substituents at 10-OH, and found most of them to be more potent than the parent compound (Park, 1996). Similar derivatives recently synthesized by Hu et al. also yielded compounds more potent than GB (2) (Hu, 1999; Hu, 2000), whereas other variations in GA (1) and GB (2) led to a decrease in activity (Hu, 2000; Hu, 2001).

However, none of the cited references disclose labeled analogs of ginkgolides useful for imaging studies. The following describes the preparation of a series of ginkgolide derivatives with photoactivatable groups and fluorescent groups, as well as groups that potentially can be radiolabeled with positron emitters such as $^{11}$C or $^{18}$F. These analogs, together with the native terpene trilactones (1-6), have been assessed for their ability to displace radioligand binding to cloned PAFR.

SUMMARY OF THE INVENTION

The subject invention provides a compound having the structure:

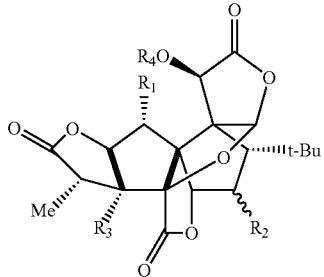

wherein $R_1$ is H, OH, a photoactivatable moiety, a fluorescent moiety, or a radioactive moiety;
wherein $R_2$ is H, OH, a photoactivatable moiety, a fluorescent moiety, or a radioactive moiety;
wherein $R_3$ is H or OH;
wherein $R_4$ is H, OH, a photoactivatable moiety, a fluorescent moiety, or a radioactive moiety; and
wherein at least one of $R_1$, $R_2$, $R_3$, or $R_4$ is a photoactivatable moiety, a fluorescent moiety, or a radioactive moiety,
or an optically pure enantiomer of the compound.

The invention also provides a compound having the structure:

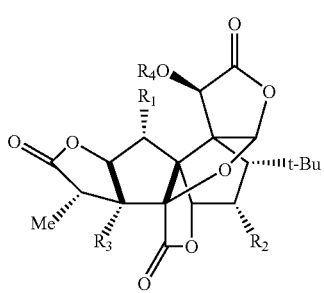

wherein $R_1$ is H, OH;
wherein $R_2$ is H, OH, F, Br, unsubstituted or substituted, straight or branched ($C_1$-$C_5$) alkyl, ($C_2$-$C_5$) alkenyl, or ($C_2$-$C_5$) alkynyl;
wherein $R_3$ is H or OH; and
wherein $R_4$ is H, OH, -A-Ar, -A-Z-Ar, —SO$_2$—Ar, or -A-NR$_5$, or —R$_6$,
where A is a ($C_1$-$C_8$) alkyl group, which is unsubstituted or substituted by a straight or branched ($C_1$-$C_5$) alkyl chain;
Z is carbon, oxygen, sulfur or nitrogen;
Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, ($C_1$-$C_{10}$) alkyl, ($C_2$-$C_{10}$) alkenyl, ($C_2$-$C_{10}$) alkynyl, ($C_1$-$C_{10}$) haloalkyl, ($C_1$-$C_{10}$) alkoxy, ($C_2$-$C_{10}$) alkenyloxy, ($C_2$-$C_{10}$) alkynyloxy, ($C_1$-$C_{10}$) haloalkoxy, a phenyl group, a phenoxy group, an aralkyl group, an aralkyloxy group, a substituted phenyl group, a substituted phenoxy group, a substituted aralkyl group, a substituted aralkyloxy group, —COR$_5$, —COR$_6$, —CONR$_5$R$_6$, —CO$_2$R$_5$, —NHCOR$_5$, —NH(OH), —N(OH)COR$_5$, —CHOR$_5$, —OCH$_2$CO$_2$R$_5$, —CH$_2$SR$_5$, —CH$_2$NR$_5$R$_6$, —SR$_5$, —OSR$_5$, —O$_2$NR$_5$R$_6$, —NR$_5$R$_6$, —NR$_5$SO$_2$R$_6$,
in which $R_5$ and $R_6$ are the same or different and each is hydrogen, a ($C_1$-$C_{10}$)alkyl or a ($C_1$-$C_3$) cycloalkyl group, —SCX$_3$ in which X is a halogen, —CN, —NO$_2$ or -Z-A-Z'- in which Z and A are as defined above and Z' represents carbon, oxygen, sulfur, or nitrogen, or an optically pure enantiomer or a salt of the compound.

The invention also provides a compound having the structure:

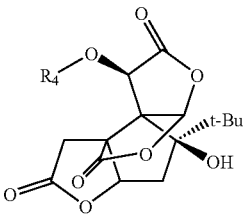

wherein $R_4$ is a photoactivatable moiety, a fluorescent moiety, or a radioactive moiety. The photoactivatable moiety, fluorescent moiety, and radioactive moiety are as defined above.

The invention also provides a compound having the structure:

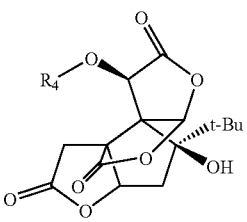

wherein $R_4$ is H, OH, -A-Ar, -A-Z-Ar, —SO$_2$—Ar, or -A-NR$_5$, or —R$_6$,
where A is a ($C_1$-$C_8$) alkyl group, which is unsubstituted or substituted by a straight or branched ($C_1$-$C_5$)alkyl chain;
Z is carbon, oxygen, sulfur or nitrogen;
Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, ($C_1$-$C_{10}$) alkyl, ($C_2$-$C_{10}$) alkenyl, ($C_2$-$C_{10}$) alkynyl, ($C_1$-$C_{10}$) haloalkyl, ($C_1$-$C_{10}$) alkoxy, ($C_2$-$C_{10}$) alkenyloxy, ($C_2$-$C_{10}$) alkynyloxy, ($C_1$-$C_{10}$) haloalkoxy, a phenyl group, a phenoxy group, an aralkyl group, an aralkyloxy group, a substituted phenyl group, a substituted phenoxy group, a substituted aralkyl group, a substituted aralkyloxy group, —COR$_5$, —COR$_6$, —CONR$_5$R$_6$, —CO$_2$R$_5$, —NHCOR$_5$, —NH(OH), —N(OH)COR$_5$, —CHOR$_5$, —OCH$_2$CO$_2$R$_5$, —CH$_2$SR$_5$, —CH$_2$NR$_5$R$_6$, —SR$_5$, —OSR$_5$, —O$_2$NR$_5$R$_6$, —NR$_5$R$_6$, —NR$_5$SO$_2$R$_6$, in which R$_5$ and R$_6$ are the same or different and each is hydrogen, a (C$_1$-C$_{10}$) alkyl or a (C$_3$-C$_{10}$) cycloalkyl group, —SCX$_3$ in which X is a halogen, —CN, —NO$_2$ or -Z-A-Z'- in which Z and A are as defined above and Z' represents carbon, oxygen, sulfur, or nitrogen.

The subject invention also provides a compound having the structure:

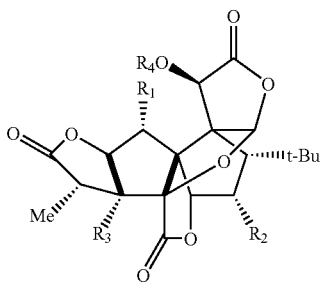

wherein R1 is H or OH;
wherein R2 is H, OH, halogen, unsubstituted or substituted, straight or branched (C$_1$-C$_5$) alkyl group, (C$_2$-C$_5$) alkenyl, or a (C$_2$-C$_5$) alkynyl, (C$_1$-C$_5$) alkoxy, (C$_2$-C$_5$) alkenyloxy, or (C$_2$-C$_5$) alkynyloxy, —N3, —COR5, —CONR5R6, —CO2R5, —OCOR5, —NH(OH), —NR5R6, —NHCOR5, —N(OH)COR5, —CH2OR5, —OCH2CO2R5, —CH2SR5, —CH2NR5R6, —SR5, —OSR5, or —NR5SO2R6,
where R5 and R6 are each independently hydrogen, substituted or unsubstituted (C$_1$-C$_5$) alkyl, (C$_2$-C$_5$) alkenyl, or (C$_2$-C$_5$) alkynyl, or a cycloalkyl or aryl group having 3 to 10 carbon atoms;
wherein R3 is H or OH;
wherein R4 is H, (C1-C10) alkyl, (C1-C10) alkenyl, (C1-C10) alkynyl, -A-Ar, -A-Z-Ar, —SO$_2$—Ar, or -A-NR$_5$, or —R$_7$,
where A is (C1-C8) alkyl, (C2-C8) alkenyl, (C2-C8) alkynyl, which is unsubstituted or substituted by a straight or branched (C$_1$-C$_5$) alkyl chain;
Z is carbon, oxygen, sulfur or nitrogen;
Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, substituted or unsubstituted (C1-C10) alkyl, (C2-C10) alkenyl, (C2-C10) alkynyl, (C1-C10) haloalkyl, (C1-C10) alkoxy, (C2-C10) alkenyloxy group, (C2-C10) alkynyloxy, (C1-C10) haloalkoxy, a phenyl group, a phenoxy group, an aralkyl group, an aralkyloxy group, a substituted phenyl group, a substituted phenoxy group, a substituted aralkyl group, a substituted aralkyloxy group, —COR$_6$, —CONR$_6$R$_6$, —CO$_2$R$_6$, —NHCOR$_6$, —NH(OH), —N(OH)COR$_6$, —CHOR$_6$, —OCH$_2$CO$_2$R$_6$, —CH$_2$SR$_6$, —CH$_2$NR$_6$R$_6$, —SR$_6$, —OSR$_6$, —NR$_6$R$_6$, —NR$_6$SO$_2$R$_6$,
where R6 is hydrogen, (C1-C10) alkyl, (C3-C10) cycloalkyl, —SCX3 in which X is a halogen, —CN, —NO2 or -Z-A-Z'- in which Z and A are as defined above and Z' represents carbon, oxygen, sulfur or nitrogen, or an optically pure enantiomer, or a tautomer, or a salt of the compound.

The invention further provides a method of inhibiting activation of the platelet-activating factor receptor (PAFR) which comprises contacting the PAFR with any of the disclosed compounds so as to thereby inhibit activation of the PAFR.

The invention further provides a method of treating a platelet-activating factor (PAF) associated condition in a subject comprising administering to the subject an amount of any of the disclosed compounds effective to treat the PAF-associated disease.

The invention further provides a process for synthesizing compounds of the invention.

The invention also provides a process of forming a secondary amine compound from an azide of the compound by contacting the azide of the compound with hydrogen, palladium and carbon in a polar-protic solvent.

The invention also provides a method of detecting the localization of a receptor that binds any of the described compounds in a subject, comprising administering the compound to the subject and imaging the subject's body to identify the point of accumulation of the compound in the subject, thereby detecting the localization of the receptor in the subject.

The invention also provides a method of identifying a receptor that binds any of the described compounds in a subject, comprising administering the compound to the subject, imaging the subject's body to identify the point of accumulation of the compound in the subject, and identifying the receptor present at the point of accumulation of the compound, thereby identifying the receptor in the subject.

The terpene trilactones, ginkgolides and bilobalide, are structurally unique constituents of *Ginkgo biloba* extracts, which exhibit various neuromodulatory properties. Although the terpene trilactones are believed to be responsible for some of these effects, the specific interactions with targets in the central nervous system remain to be elucidated on a molecular level. Ginkgolides are known antagonists of the platelet-activating factor (PAF) receptor. Herein we have prepared several ginkgolide derivatives carrying photoactivatable and fluorescent groups, as wells as groups where radioactive labels can be incorporated for the purpose of performing photolabeling, ex vivo autoradiography, and positron emission tomography (PET) studies. The first examination of the binding of native terpene trilactones and their derivatives to the cloned PAF receptor is described. These studies have shown that ginkgolide derivatives with aromatic photoactivatable substituents are potent PAF receptor antagonists with K$_i$ values of 0.09-0.79 μM and hence excellent ligands for clarifying the binding of ginkgolides to PAF receptor by photolabeling studies. Ginkgolide derivatives incorporating both fluorescent and photoactivatable groups still retained binding affinity to the PAF receptor, and are promising ligands for photolabeling and sequencing. Finally, among the candidates for incorporation of radiotracers one compound was a potent antagonist of PAF receptor with a K$_i$ value of 0.99 μM and is therefore a potential ligand for probing ginkgolide-PAF receptor interactions in the brain, as well as elucidating new targets for ginkgolides.

DETAILED DESCRIPTION OF THE INVENTION

Figure 1:
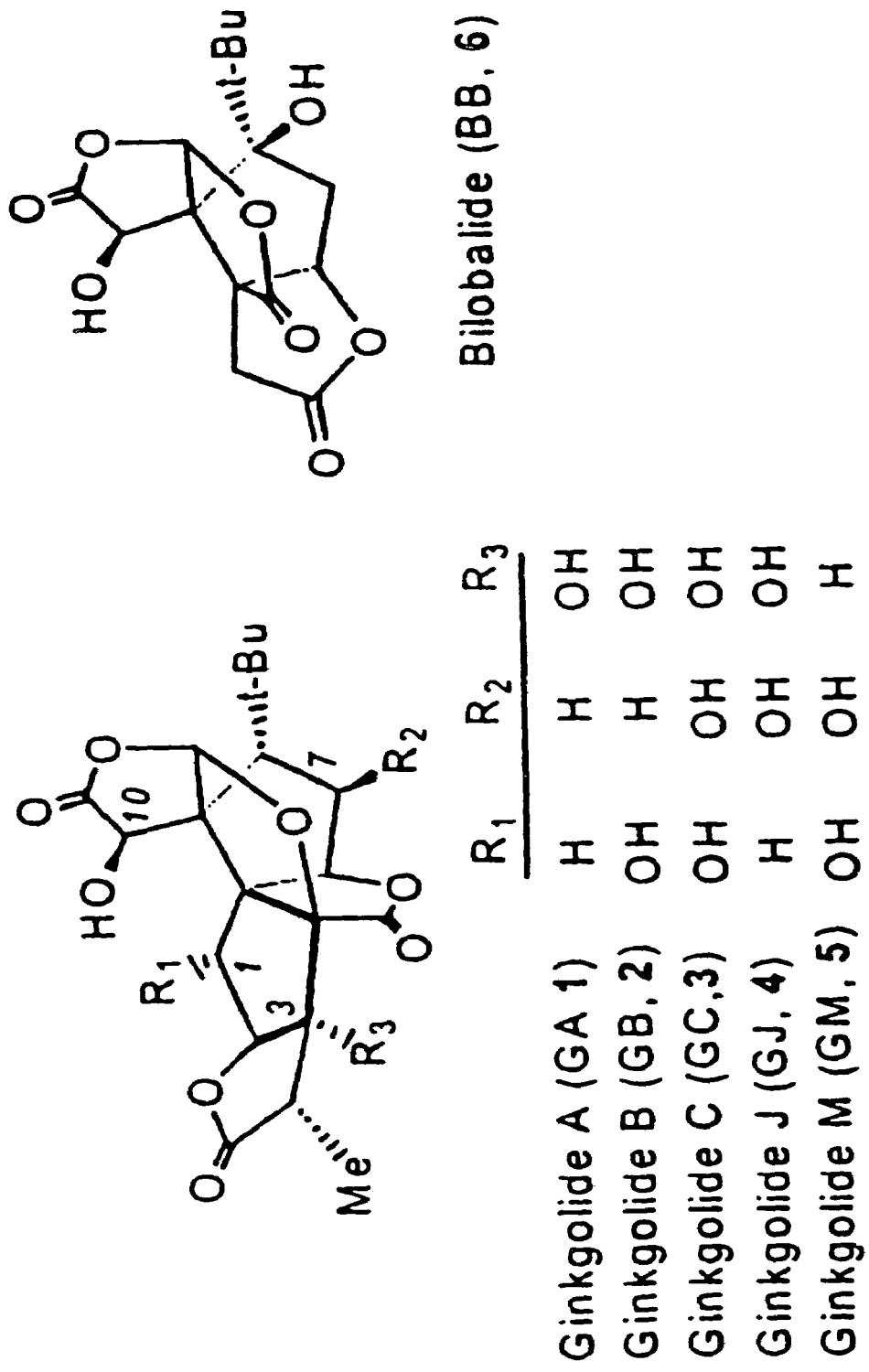
FIG. 1. Terpene trilactones isolated from *Ginkgo biloba*. GA, GB, and GC are found in the leaves and root bark of *G. biloba*, but GJ is found only in the leaves, and GM only in the root bark FIG. 2. Structures of platelet-activating factor (PAF), the endogenous ligand for the PAFR, and WEB 2086, a potent and selective antagonist, both of which have been used in radioligand binding studies.

The invention provides a compound having the structure:

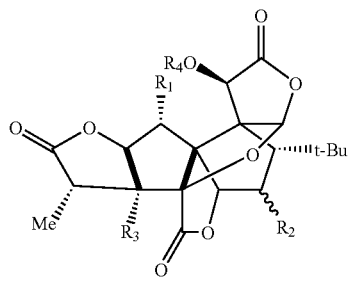

(I)

wherein $R_1$ is H, OH, a photoactivatable moiety, a fluorescent moiety, or a radioactive moiety;
  wherein $R_2$ is H, OH, a photoactivatable moiety, a fluorescent moiety, or a radioactive moiety;
  wherein $R_3$ is H or OH;
  wherein $R_4$ is H, OH, a photoactivatable moiety, a fluorescent moiety, or a radioactive moiety; and
  wherein at least one of $R_1$, $R_2$, $R_3$, or $R_4$ is a photoactivatable moiety, a fluorescent moiety, or a radioactive moiety,
  or an optically pure enantiomer of the compound.

In the compound, $R_1$ may be a fluorescent moiety and each of $R_2$ and $R_4$ may be H or OH; $R_2$ may be a fluorescent moiety or a radioactive moiety and each of $R_1$ and $R_4$ may be H or OH; or $R_4$ may be a photoactivatable moiety or a radioactive moiety and each of $R_1$ and $R_2$ may be H or OH.

The photoactivatable moiety may be a phenylazide, a purine or pyrimidine azides, a diazoacetate, a diazoketone, a nitrobenzene, or an aryldiazonium salt. In some embodiments, the photoactivatable moiety may be benzophenone, trifluoromethyldiazirine tetrafluorophenyl, 8-azidoadenosine, 2-azidoadenosine, or 3H,3-aryldiazirine.

The fluorescent moiety may be a fluorescent amine. In some embodiments, the fluorescent moiety may be 5-(dimemethylamino)naphthalene-sulfonyl chloride, 1-(Bromoacetyl)pyrene, 3-Bromoacetyl-7-diethylaminocoumarin, 3-Bromomethyl-6,7-dimethoxycoumarin, 8-Bromomethyl-4,4-difluoro-1,3,5,7-tetramethyl-4-bora-3a,4a-diaza-s-indacene, 3-Bromomethyl-6,7-dimethoxy-1-methyl-2(1H)-quinoxazolinone, 6-Bromoacetyl-2-dimethylaminonaphthalene, or 4-(9-Anthroyloxy)phenacyl bromide.

The radioactive moiety may be $^{11}$C, $^{13}$N, $^{15}$O, $^3$H or $^{18}$F.

In specific embodiments of the compounds of this invention, the photoactivatable moiety may be benzophenone, trifluoromethyldiazirine or tetrafluorophenyl; the fluorescent moiety may be 5-(dimemethylamino)naphthalene-sulfonyl ("dansyl"); and the radioactive moiety may be $^{18}$F, $^{11}$C or $^3$H.

In a specific embodiment the invention also provides compounds having the structure:

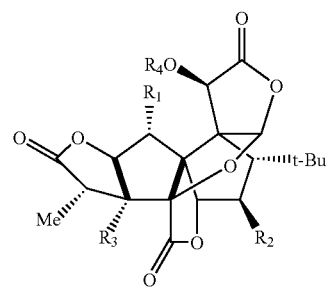

where $R_1$, $R_2$, $R_3$ and $R_4$ are defined as above.

In specific embodiments, $R_1$ may be H, OH, a fluorescent moiety; $R_2$ may be H, OH, a fluorescent moiety, or a radioactive moiety; $R_3$ may be H or OH; and $R_4$ may be H, OH, a photoactivatable moiety, or a radioactive moiety.

In yet further embodiments, $R_1$ may be —O-dansyl; or $R_2$ may be —O-dansyl; or $R_2$ may be —$^{11}$CH$_3$; or $R_2$ may be —CH$_2$CH$_2{}^{18}$F; or $R_2$ may be $^{18}$F; or $R_2$ may be $^3$H; or $R_4$ may be a benzophenone moiety; or $R_4$ may be a trifluoromethyldiazirine moiety; or $R_4$ may be a tetrafluorophenyl azide moiety; or $R_4$ may be —$^{11}$CH$_3$; or $R_4$ may be —CH$_2$CH$_2{}^{18}$F.

In one specific embodiment, the compound has the structure:

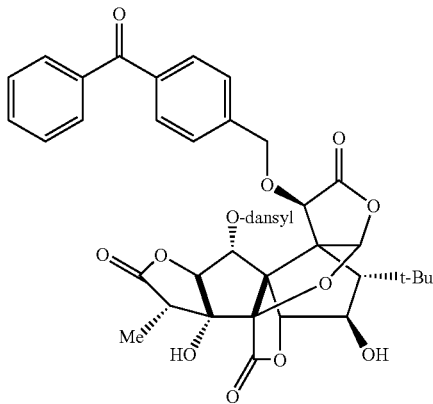

In another specific embodiment, the compound has the structure:

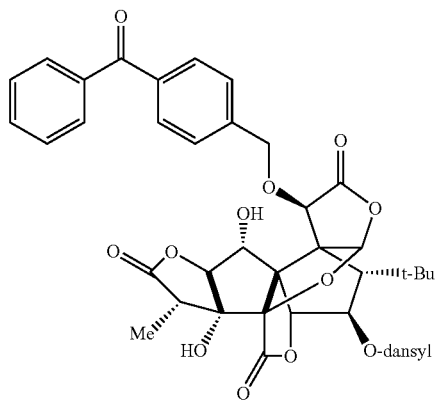

In another specific embodiment, the compound has the structure:

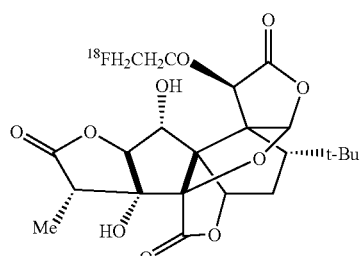

In another specific embodiment, the compound has the structure:

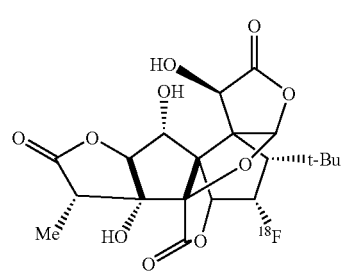

In another specific embodiment, the compound has the structure:

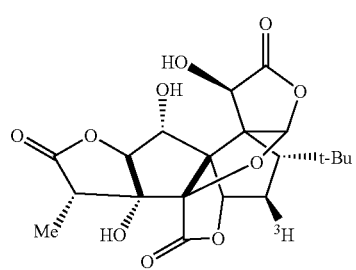

In another specific embodiment, the compound has the structure:

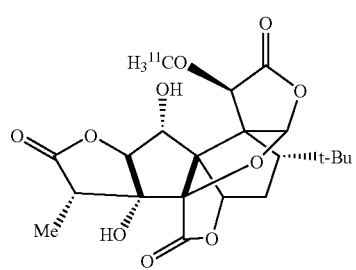

In another specific embodiment, the compound has the structure:

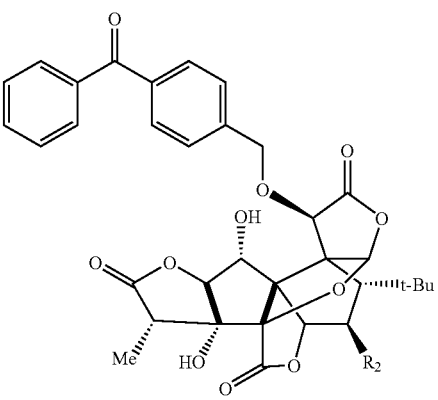

wherein $R_2$ is H or OH.

In another specific embodiment, the compound has the structure:

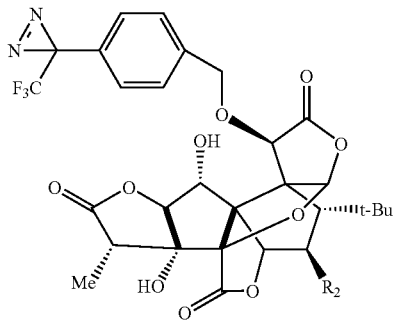

wherein R₂ is H or OH.

In another specific embodiment, the compound has the structure:

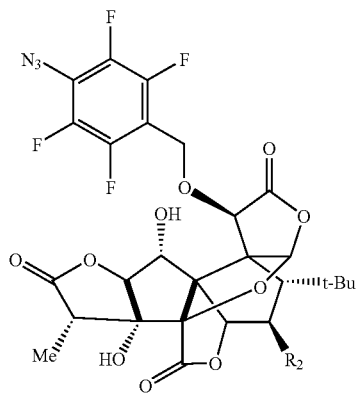

wherein R₂ is H or OH.

The invention also provides a compound having the structure:

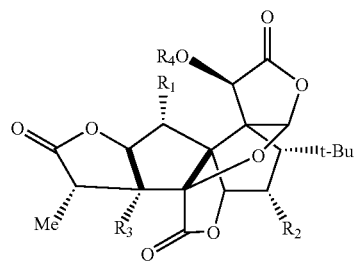

wherein $R_1$ is H or OH, wherein $R_2$ is H, OH, halogen, unsubstituted or substituted, straight or branched ($C_1$-$C_5$) alkyl group, ($C_2$-$C_5$) alkenyl, or a ($C_2$-$C_5$) alkynyl, ($C_1$-$C_5$) alkoxy, ($C_2$-$C_5$) alkenyloxy, or ($C_2$-$C_5$) alkynyloxy, —$N_3$, —$COR_5$, —$CONR_5R_6$, —$CO_2R_5$, —$OCOR_5$, —NH(OH), —$NR_5R_6$, —$NHCOR_5$, —N(OH)$COR_5$, —$CH_2OR_5$, —$OCH_2CO_2R_5$, —$CH_2SR_5$, —$CH_2NR_5R_6$, —$SR_5$, —$OSR_5$, or —$NR_5SO_2R_6$, where $R_5$ and $R_6$ are each, independently, hydrogen, substituted or unsubstituted ($C_1$-$C_5$) alkyl, ($C_2$-$C_5$) alkenyl, or ($C_2$-$C_5$) alkynyl, or a cycloalkyl or aryl group having 3 to 10 carbon atoms;

wherein $R_3$ is H or OH; and wherein $R_4$ is H, OH, ($C_1$-$C_{10}$) alkyl, ($C_2$-$C_{10}$) alkenyl, ($C_2$-$C_{10}$) alkynyl, -A-Ar, -A-Z-Ar, —$SO_2$—Ar, or -A-$NR_6$, or —$R_6$, where A is ($C_1$-$C_8$) alkyl, ($C_2$-$C_8$) alkenyl, ($C_2$-$C_8$)alkynyl, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, substituted or unsubstituted ($C_1$-$C_{10}$) alkyl, ($C_2$-$C_{10}$) alkenyl, ($C_2$-$C_{10}$) alkynyl, ($C_1$-$C_{10}$) haloalkyl, ($C_1$-$C_{10}$) alkoxy, ($C_2$-$C_{10}$) alkenyloxy, ($C_2$-$C_{10}$) alkynyloxy, ($C_1$-$C_{10}$) haloalkoxy, a phenyl group, a phenoxy group, an aralkyl group, an aralkyloxy group, a substituted phenyl group, a substituted phenoxy group, a substituted aralkyl group, a substituted aralkyloxy group, —$COR_6$, —$CONR_6R_6$, —$CO_2R_6$, —$NHCOR_6$, —NH(OH), —N(OH)$COR_6$, —$CH_2OR_6$, —$OCH_2CO_2R_6$, —$CH_2SR_6$, —$CH_2NR_6R_6$, —$SR_6$, —$OSR_6$, —$NR_6R_6$, —$NR_6SO_2R_6$, where $R_6$ is hydrogen, ($C_1$-$C_{10}$) alkyl, ($C_3$-$C_{10}$) cycloalkyl, —$SCX_3$ in which X is a halogen, —CN, —NO2 or -Z-A-Z'- in which Z and A are as defined above and Z' represents carbon, oxygen, sulfur, or nitrogen;

or an optically pure enantiomer, or a tautomer, or a salt of the compound.

In one embodiment, the compound has the structure:

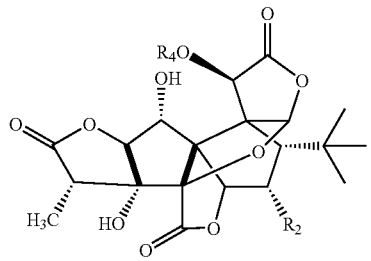

wherein $R_2$ is Cl, F, OH, a substituted or unsubstituted, straight or branched ($C_1$-$C_5$) alkyl, ($C_2$-$C_5$) alkenyl, ($C_2$-$C_5$) alkynyl, ($C_1$-$C_5$) alkoxy, ($C_2$-$C_5$) alkenyloxy, or ($C_2$-$C_5$) alkynyloxy, —$N_3$, —$COR_5$, —$CONR_5R_6$, —$CO_2R_5$, —$OCOR_5$, —NH(OH), —$NR_5R_6$, —NH$COR_5$, —N(OH)$COR_5$, —$CH_2OR_5$, —$OCH_2CO_2R_5$, —$CH_2SR_5$, —$CH_2NR_5R_6$, —$SR_5$, —$OSR_5$, or —$NR_5SO_2R_6$, where $R_5$ and $R_6$ are each, independently, hydrogen, substituted or unsubstituted ($C_1$-$C_5$) alkyl, ($C_2$-$C_5$) alkenyl, or ($C_2$-$C_5$) alkynyl, or a cycloalkyl or aryl group having 3 to 10 carbon atoms;

wherein $R_4$ is H or $R_8$;

wherein $R_4$ is $R_8$ when $R_2$ is F;

wherein $R_8$ is ($C_1$-$C_{10}$) alkyl, ($C_2$-$C_{10}$) alkenyl, ($C_2$-$C_{10}$) alkynyl, -A-Ar, -A-Z-Ar, —$SO_2$—Ar, or -A-$NR_6$, where A is an unsubstituted, straight chain $(C_1-C_5)$alkyl, $(C_2-C_5)$ alkenyl, $(C_2-C_5)$ alkynyl;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, hydroxy, substituted or unsubstituted $(C_1-C_{10})$ alkyl, $(C_2-C_{10})$ alkenyl, $(C_2-C_{10})$ alkynyl, $(C_1-C_{10})$ alkoxy, $(C_2-C_{10})$ alkenyloxy, $(C_2-C_{10})$ alkynyloxy, phenyl, phenoxy, aralkyl, or aralkyloxy, —$COR_6$, —$CONR_6R_6$, —$CO_2R_6$, —$NHCOR_6$, —$NH(OH)$, —$N(OH)COR_6$, —$CH_2OR_6$, —$OCH_2CO_2R_6$, —$CH_2SR_6$, —$CH_2NR_6R_6$, —$SR_6$, —$OSR_6$, —$NR_6R_6$, or —$NR_6SO_2R_6$, where $R_6$ is hydrogen, $(C_1-C_{10})$ alkyl, $(C_3-C_{10})$ cycloalkyl, —$SCX_3$ in which X is a halogen, —CN, —$NO_2$ or -Z-A-Z'- in which Z and A are as defined above and Z' represents carbon, oxygen, sulfur, or nitrogen, or an optically pure enantiomer, or a tautomer, or a salt of the compound.

In another embodiment, $R_4$ is H or -A-Ar.

In another embodiment, $R_4$ is H or —$CH_2C_6H_5$.

In another embodiment, $R_2$ is OH, Cl, —$N_3$, —$OCOR_3$, or —$NR_3R_4$.

In another embodiment, $R_2$ is OH, Cl, —$OCOCH_3$, —$OCOCH_2C_6H_5$, —$N_3$, —$NH_2$, —$NHCH_3$, —$NHCH_2CH_3$.

In another embodiment, $R_2$ is OH, Cl, —$OCOCH_3$, —$OCOCH_2C_6H_5$, —$N_3$, —$NH_2$, —$NHCH_3$, —$NHCH_2CH_3$; and wherein $R_4$ is H or —$CH_2C_6H_5$.

In another embodiment, $R_1$ is OH, $R_2$ is F, $R_3$ is OH, and $R_4$ is H.

In another embodiment, $R_2$ is Cl, and $R_4$ is H.

In another embodiment, $R_2$ is —$N_3$, and $R_4$ is H.

In another embodiment, $R_2$ is —$NHCH_3$, and $R_4$ is H.

In another embodiment, $R_2$ is —$NHCH_2CH_3$, and $R_4$ is H.

In another embodiment, $R_2$ is —$OCOCH_2C_6H_5$, and $R_4$ is H.

In another embodiment, $R_2$ is F, and $R_4$ is —$CH_2C_6H_5$.

In another embodiment, $R_2$ is Cl, and $R_4$ is —$CH_2C_6H_5$.

In another embodiment, $R_2$ is H, and $R_4$ is —$CH_2C_6H_5$.

In another embodiment, $R_2$ is OH, and wherein $R_4$ is —$CH_2C_6H_5$.

In another embodiment, the compound has the structure:

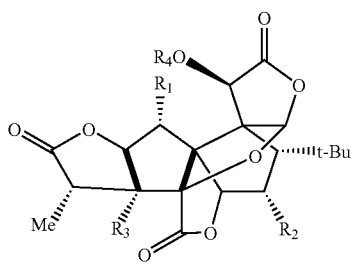

wherein $R_1$ is H or OH;

wherein $R_2$ is H, F, Br, unsubstituted or substituted, straight or branched $(C_1-C_5)$ alkyl group, $(C_2-C_5)$ alkenyl, or a $(C_2-C_5)$ alkynyl;

wherein $R_3$ is H or OH; and wherein $R_4$ is H, -A-Ar, -A-Z-Ar, —$SO_2$—Ar, or -A-$NR_6$, or —$R_6$, where A is an alkylene group having 1 to 8 carbon atoms, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, $(C_1-C_{10})$ alkyl, $(C_2-C_{10})$ alkenyl, $(C_2-C_{10})$ alkynyl, a $(C_1-C_{10})$ haloalkyl, an $(C1-C_{10})$ alkoxy, an $(C_2-C_{10})$ alkenyloxy, an $(C_2-C_{10})$ alkynyloxy, a $(C_1-C_{10})$ haloalkoxy, a phenyl group, a phenoxy group, an aralkyl group, an aralkyloxy group, a substituted phenyl group, a substituted phenoxy group, a substituted aralkyl group, a substituted aralkyloxy group, —$COR_6$, —$CONR_6R_6$, —$CO_2R_6$, —$NHCOR_6$, —$NH(OH)$, —$N(OH)COR_6$, —$CH_2OR_6$, —$OCH_2CO_2R_6$, —$CH_2SR_6$, —$CH_2NR_6R_6$, —$SR_6$, —$OSR_6$, —$NR_6R_6$, —$NR_6SO_2R_6$, where $R_6$ is hydrogen, $(C_1-C_{10})$ alkyl, $(C_3-C_{10})$ cycloalkyl, —$SCX_3$ in which X is a halogen, —CN, —$NO_2$ or -Z-A-Z'- in which Z and A are as defined above and Z' represents carbon, oxygen, sulfur, or nitrogen, or an optically pure enantiomer, or a salt of the compound.

In one embodiment, $R_2$ is F.

In another embodiment, the compound has the structure:

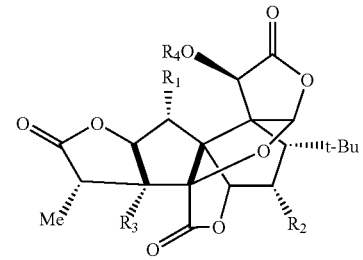

wherein $R_1$ is H, or OH;

wherein $R_2$ is H, OH, F, Br, unsubstituted or substituted, straight or branched $(C_1-C_5)$ alkyl, $(C_2-C_5)$ alkenyl, or $(C_2-C_5)$ alkynyl;

wherein $R_3$ is H or OH; and wherein $R_4$ is H, OH, -A-Ar, -A-Z-Ar, —$SO_2$—Ar, or -A-$NR_5$, or —$R_6$, where A is an $(C_1-C_8)$ alkyl group, which is unsubstituted or substituted by a straight or branched $(C_1-C_5)$ alkyl chain;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, $(C_1-C_{10})$ alkyl, $(C_2-C_{10})$ alkenyl, $(C_2-C_{10})$ alkynyl, $(C_1-C_{10})$ haloalkyl, $(C_1-C_{10})$ alkoxy, $(C_2-C_{10})$ alkenyloxy, $(C_2-C_{10})$ alkynyloxy, $(C_1-C_{10})$ haloalkoxy, a phenyl group, a phenoxy group, an aralkyl group, an aralkyloxy group, a substituted phenyl group, a substituted phenoxy group, a substituted aralkyl group, a substituted aralkyloxy group, —COR$_5$, —COR$_6$, —CONR$_5$R$_6$, —CO$_2$R$_5$, —NHCOR$_5$, —NH(OH), —N(OH)COR$_5$, —CHOR$_5$, —OCH$_2$CO$_2$R$_5$, —CH$_2$SR$_5$, —CH$_2$NR$_5$R$_6$, —SR$_5$, —OSR$_5$, —O$_2$NR$_5$R$_6$, —NR$_5$R$_6$, —NR$_5$SO$_2$R$_6$, in which R$_5$ and R$_6$ are the same or different and each is hydrogen, (C$_1$-C$_{10}$) alkyl or a (C$_3$-C$_{10}$) cycloalkyl, —SCX$_3$ in which X is a halogen, —CN, —NO$_2$ or -Z-A-Z'- in which Z and A are as defined above and Z' represents carbon, oxygen, sulfur, or nitrogen, or an optically pure enantiomer, or a salt of the compound.

In another embodiment, R$_2$ is F.

The subject invention also provides a compound having the structure:

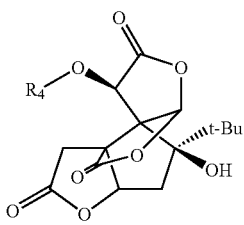

wherein R$_4$ is a photoactivatable moiety, a fluorescent moiety, or a radioactive moiety.

In one embodiment, the photoactivatable moiety is a phenylazide, a purine or pyrimidine azides, a diazoacetate, a diazoketone, a nitrobenzene, or an aryldiazonium salt.

In another embodiment, the photoactivatable moiety is benzophenone, trifluoromethyldiazirine tetrafluorophenyl, 8-azidoadenosine, 2-azidoadenosine, or 3H,3-aryldiazirine.

In another embodiment, the fluorescent moiety is a fluorescent amine.

In another embodiment, the fluorescent moiety is 5-(dimemethylamino)naphthalene-sulfonyl(dansyl), 1-(Bromoacetyl)pyrene, 3-Bromoacetyl-7-diethylaminocoumarin, 3-Bromomethyl-6,7-dimethoxycoumarin, 8-Bromomethyl-4,4-difluoro-1,3,5,7-tetramethyl-4-bora-3a,4a-diaza-s-indacene, 3-Bromomethyl-6,7-dimethoxy-1-methyl-2(1H)-quinoxazolinone, 6-Bromoacetyl-2-dimethylaminonaphthalene, or 4-(9-Anthroyloxy)phenacyl bromide.

In another embodiment, the radioactive moiety is $^{18}$F, $^{11}$C, $^3$H.

The invention also provides a compound having the structure:

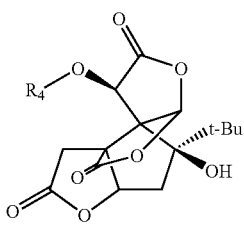

wherein R$_4$ is H, OH, -A-Ar, -A-Z-Ar, —SO$_2$—Ar, or -A-NR$_5$, or —R$_6$, where A is a (C$_1$-C$_8$) alkyl group, which is unsubstituted or substituted by a straight or branched (C$_1$-C$_5$) alkyl chain;

Z is carbon, oxygen, sulfur or nitrogen;

Ar is a phenyl group, a pyridyl group, a naphthyl group, a pyrimidyl group, or a quinolyl group, each of which may contain heteroatoms and may be unsubstituted or substituted by one to five substituents selected from the group consisting of hydrogen, halogen, a hydroxy group, a carboxylic acid group, (C$_1$-C$_{10}$) alkyl, (C$_2$-C$_{10}$) alkenyl, (C$_2$-C$_{10}$) alkynyl, (C$_1$-C$_{10}$) haloalkyl, (C$_1$-C$_{10}$) alkoxy, (C$_2$-C$_{10}$) alkenyloxy, (C$_2$-C$_{10}$) alkynyloxy, (C$_1$-C$_{10}$) haloalkoxy, a phenyl group, a phenoxy group, an aralkyl group, an aralkyloxy group, a substituted phenyl group, a substituted phenoxy group, a substituted aralkyl group, a substituted aralkyloxy group, —COR$_5$, —COR$_6$, —CONR$_5$R$_6$, —CO$_2$R$_5$, —NHCOR$_5$, —NH(OH), —N(OH)COR$_5$, —CHOR$_5$, —OCH$_2$CO$_2$R$_5$, —CH$_2$SR$_5$, —CH$_2$NR$_5$R$_6$, —SR$_5$, —OSR$_5$, —O$_2$NR$_5$R$_6$, —NR$_5$R$_6$, —NR$_5$SO$_2$R$_6$, in which R$_5$ and R$_6$ are the same or different and each is hydrogen, (C$_1$-C$_{10}$) alkyl or a (C$_3$-C$_{10}$) cycloalkyl group, —SCX$_3$ in which X is a halogen, —CN, —NO$_2$ or -Z-A-Z'- in which Z and A are as defined above and Z'represents carbon, oxygen, sulfur, or nitrogen, or an optically pure enantiomer, or a salt of the compound.

In one embodiment of the above compounds, if any group is substituted, the substituent is halogen, hydroxyl, straight chain (C$_1$-C$_5$)alkyl, branched chain (C$_3$-C$_5$)alkyl, (C$_3$-C$_{10}$) cycloalkyl, straight chain (C$_1$-C$_5$)alkylcarbonyloxy, branched chain (C$_3$-C$_5$)alkylcarbonyloxy, arylcarbonyloxy, straight chain (C$_1$-C$_5$) alkoxycarbonyloxy, branched chain (C$_3$-C$_5$)alkoxycarbonyloxy, aryloxycarbonyloxy, carboxylate, straight chain (C$_1$-C$_5$)alkylcarbonyl, branched chain (C$_3$-C$_5$)alkylcarbonyl, straight chain (C$_1$-C$_5$)alkoxycarbonyl, branched chain (C$_3$-C$_5$)alkoxycarbonyl, aminocarbonyl, straight chain (C$_1$-C$_5$)alkylthiocarbonyl, branched chain (C$_3$-C$_5$) alkylthiocarbonyl, straight chain (C$_1$-C$_5$)alkoxyl, branched chain (C$_1$-C$_5$)alkoxyl, phosphate, phosphonate, cyano, amino, straight chain (C$_1$-C$_5$)alkylamino, branched chain (C$_3$-C$_5$)alkylamino, straight chain (C$_1$-C$_5$)dialkylamino, branched chain (C$_3$-C$_5$)dialkylamino, arylamino, diarylamino, straight chain (C$_1$-C$_5$)alkylarylamino, branched chain (C$_3$-C$_5$)alkylarylamino, acylamino, straight chain (C$_1$-C$_5$)alkylcarbonylamino, branched chain (C$_3$-C$_5$)alkylcarbonylamino, arylcarbonylamino, carbamoyl, ureido, amidino, imino, sulfhydryl, straight chain (C$_1$-C$_5$)alkylthio, branched chain (C$_3$-C$_5$)alkylthio, arylthio, thiocarboxylate, sulfates, sulfonato, sulfamoyl, sulfonamido, nitro, trifluoromethyl, azido, 4-10 membered heterocyclyl, straight chain (C$_1$-C$_{30}$) alkylaryl, branched chain (C$_3$-C$_{30}$)alkylaryl, or an aromatic or 5-6 membered heteroaromatic moiety, which substituent may be further substituted by any of the above.

The subject invention also provides a pharmaceutically acceptable salt of above compounds, wherein the salt is the chloride, mesylate, maleate, fumarate, tartarate, hydrochloride, hydrobromide, esylate, p-toluenesulfonate, benzoate, acetate, phosphate and sulfate salts.

The subject invention also provides a pharmaceutical composition comprising a therapeutically effective amount of one of the above compounds and a pharmaceutically acceptable carrier.

The subject invention also provides a process for the manufacture of a pharmaceutical composition comprising admixing any of the above compounds with a pharmaceutically acceptable carrier.

The subject invention also provides a method of inhibiting activation of the platelet-activating factor receptor (PAFR) which comprises contacting the PAFR with any of the above compounds so as to thereby inhibit activation of the PAFR.

The subject invention also provides a method of treating a platelet-activating factor (PAF) associated condition in a subject comprising administering to the subject an amount of any of the above compounds effective to treat the PAF-associated disease.

In one embodiment, the PAF-associated condition is a neurodegenerative disease, Alzheimer's disease, senile dementia, stroke, nerve cell damage due to ischemia, asthma, abnormal blood clot formation, end toxic shock, myocardial ischemia or hyperacute rejection arising from post-renal transplant or xenoperfusion.

The subject invention also provides a process of preparing the above compound comprising the steps of:
  i) reacting a compound having the structure

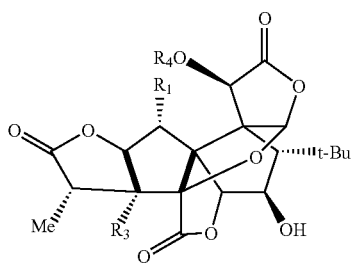

wherein $R_1$, $R_3$ and $R_4$ are as defined above, with trifluoromethanesulfonic anhydride under inert conditions to form a triflate; and
  ii) reacting the triflate of step i) with a nucleophilic reagent in a polar-aprotic solvent to substitute the triflate with the nucleophile and to form the compound.

In one embodiment of the above process, the nucleophilic reagent is sodium acetate, sodium phenylacetate, sodium azide, tetrabutylammonium fluoride hydrate, or tetrabutylammonium chloride.

In another embodiment, the polar-aprotic solvent is dichloromethane, pyridine, dimethylformamide, methylsulfoxide, or acetonitrile.

In another embodiment, the nucleophilic reagent is sodium acetate or sodium phenylacetate, further comprising hydrolyzing the product of step ii) in the presence of 1N hydrochloric acid.

In another embodiment, the nucleophilic reagent is sodium azide, further comprising reacting the product of step ii) with hydrogen in the presence of palladium and carbon in methanol or ethanol.

In another embodiment, the nucleophile is tetrabutylammonium fluoride hydrate, further comprising reacting the product of step ii) with benzyl chloride.

The subject invention also provides a process of forming a secondary amine compound from an azide of the compound by contacting the azide of the compound with hydrogen, palladium and carbon in a polar-protic solvent.

In one embodiment, the polar-protic solvent is an alcohol.

In another embodiment, the secondary amine compound has the structure:

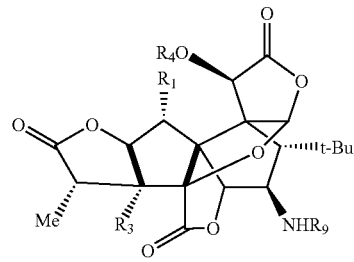

wherein $R_1$, $R_3$ and $R_4$ are as defined above and $R_9$ is an alkyl group,
and wherein the azide of the compound has the structure:

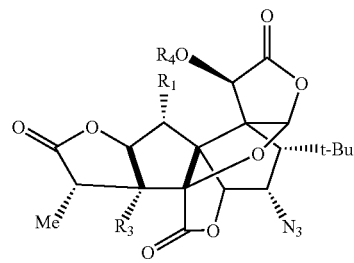

In another embodiment, the polar-protic solvent is an alcohol.

In another embodiment, the alcohol is $CH_3OH$ and $R_9$ is $CH_3$.

In another embodiment, the alcohol is $CH_3CH_2OH$ and $R_9$ is $CH_3CH_2$.

The subject invention also provides a process for detecting the binding of compound (I) to a target, comprising contacting the compound with the target and detecting the binding of the compound to the target.

In one embodiment, the target is DNA.

In another embodiment, the target is a receptor.

In another embodiment, the target is an enzyme.

The subject invention also provides a process for detecting the localization of a receptor in a subject comprising administering compound (I) to the subject and detecting at any location in the subject's body to identify a point of accumulation of the compound so as to thereby localize the receptor in the subject, wherein localization of a receptor means a higher concentration of that receptor then at other points in the subject's body.

The subject invention also provides a process of identifying a target that binds compound (I), comprising contacting the compound with the target, isolating the target so as to thereby identify the target.

In one embodiment, the target is DNA.

In another embodiment, the target is a receptor.

In another embodiment, the target is an enzyme.

The subject invention also provides a process of identifying a receptor that binds compound (I) in a subject, comprising administering the compound to the subject, imaging the subject's body to identify the point of accumulation of the compound in the subject, and identifying the receptor present at the point of accumulation of the compound, so as to thereby identify the receptor in the subject.

The invention also provides a process for detecting the binding of any of the described the compounds to a target, comprising contacting the compound with the target and detecting the binding of the compound to the target The target may be a DNA, enzyme or a receptor.

The invention also provides a process for detecting the localization of a receptor in a subject comprising administering any of the described compounds to the subject and detecting at any location in the subject's body to identify a point of accumulation of the compound so as to thereby localize the receptor in the subject, wherein localization of a receptor means a higher concentration of that receptor then at other points in the subject's body.

The invention also provides a process of identifying a target that binds any of the described compounds, comprising contacting the compound with the target and identifying target. The target may be a DNA, enzyme or a receptor.

The invention also provides a process of identifying a receptor that binds to any of the described compounds in a subject, comprising administering the compound to the subject, imaging the subject's body to identify the point of accumulation of the compound in the subject, and identifying the receptor present at the point of accumulation of the compound, thereby identifying the receptor in the subject.

The photoactivatable moieties react with a receptor, enzyme or other target upon irradiation and enable researchers to identify the targets of compounds, to determine the affinity and selectivity of the drug-target interaction, and to identify the binding site on the target. Examples are presented from three fundamentally different approaches: (1) photoaffinity labeling of target macromolecules; (2) photoactivation and release of "caged ligands"; and (3) photoimmobilization of ligands onto surfaces. A number of photoactivatable moieties are described in the literature, for example, aryl azides, which, when photoactivated to yield aryl nitrenes, can label any binding site containing carbon-hydrogen bonds by insertion into the C—H bond (Galardy, et al., J. Biol. Chem., 249: 350 (1974); U.S. Pat. No. 4,689,310; and U.S. Pat. No. 4,716, 122); and a number of others are described in U.S. Pat. No. 6,077,698, the contents of which are hereby incorporated by reference.

The photoactivatable groups can be used for treatment as well as screening studies and diagnostics. Photoactivatable groups can be used to irreversibly bind compounds to their targets. Thus, the subject invention also provides compounds useful in methods of treatment where a desired compound is irreversibly bound to its target.

The photoactivatable groups may be phenylazides, purine and pyrimidine azides, 8-azidoadenosine, 2-azidoadenosine, diazoacetates, diazoketones, nitrobenzenes, aryldiazonium salts, or 3H,3-aryldiazirines. The preferred photoactivatable moieties for use with ginkgolides are benzophenone, trifluoromethyldiazirine and tetrafluorophenyl.

The fluorescent moiety, for example, may be 5-(dimemethylamino)naphthalene-sulfonyl chloride (dansyl chloride), a fluorescent amine such as 1-pyrenemethylamine, or any number of other groups readily available from Molecular Probes—http://www.probes.com/, the contents of which are hereby incorporated by reference. Other specific groups which are useful in this invention are 1-(Bromoacetyl)pyrene, 3-Bromoacetyl-7-diethylaminocoumarin, 3-Bromomethyl-6,7-dimethoxycoumarin, 8-Bromomethyl-4,4-difluoro-1,3, 5,7-tetramethyl-4-bora-3a,4a-diaza-s-indacene, 3-Bromomethyl-6,7-dimethoxy-1-methyl-2(1H)-quinoxazolinone, 6-Bromoacetyl-2-dimethylaminonaphthalene, and 4-(9-Anthroyloxy)phenacyl bromide.

Radioactive moieties are widely known in the art and include radionuclides, radionuclides covalently attached to other groups, and metal chelates. The appropriate ginkgolide-based radioligands can be prepared using known radioactive moieties to suit the environment of use and detection method. Gamma-emitter and positron-emitter radionuclides are well-known in the art and include $^{111}$In, $^{198}$Au, $^{113}$Ag, $^{111}$Ag, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{109}$Pd, $^{105}$Rh, $^{128}$Ba, $^{197}$Hg, $^{203}$Pb, $^{212}$Pb, $^{67}$Ga, $^{68}$Ga, $^{64}$Cu, $^{67}$Cr, $^{97}$Ru, $^{75}$Br, $^{76}$Br, $^{77}$Br, $^{99m}$Tc, $^{11}$C, $^{13}$N, $^{15}$O, $^{3}$H and $^{18}$F. For positron emission tomography (PET) studies contemplated by this disclosure, ginkgolide derivatives labeled with the radionuclides [$^{18}$F]- and [$^{11}$C] possessing half lives of 110 min and 20 min, respectively, are preferred. While [$^{3}$H] is preferred for other radioactivity based studies.

This invention will be better understood from the Experimental Details which follow. However, one skilled in the art will readily appreciate that the specific, methods and results discussed are merely illustrative of the invention as described more fully in the claims which follow thereafter.

EXPERIMENTAL DETAILS

Methods

Synthesis
Ginkgolides and bilobalide (1-6) were obtained as previously described (Nakanishi, 1967). The syntheses of ginkgolide derivatives are outlined in FIGS. 3-7, and details appear below:

General Procedures.

Anhydrous solvents were dried by eluting through alumina columns. Triethylamine was freshly distilled from NaOH pellets. Unless otherwise noted, materials were obtained from a commercial supplier and were used without further purification. All reactions were performed in predried glassware under argon or nitrogen, and all reactions of involving azides or diazirines were performed in dim red light. Flash column chromatography was performed using ICN silica gel (32-63 mesh) or ICN silica gel (32-63 mesh) impregnated with sodium acetate. [van Beek, T. A. & Lelyved, G. P. (1993) Phytochem. Anal. 4, 109-114].

Thin-layer chromatography was carried out using pre-coated silica gel 60 $F_{254}$ plates with thickness of 0.25 μm. Spots were observed at 254 nm, and by staining with acetic anhydride, or cerium/molybdenum in $H_2SO_4$. $^1$H and $^{13}$C NMR spectra were obtained on Bruker DMX 300 or 400 MHZ spectrometers and are reported in parts per million (ppm) relative to internal solvent signal, with coupling constants (J) in Hertz (Hz). For $^{19}$F NMR spectra hexafluorobenzene (−162.9 ppm) was used as internal standard. High resolution mass spectra (HRMS) were measured on a JEOL JMS-HX110/100A HF mass spectrometers using a 3-nitrobenzyl alcohol (NBA) matrix and Xe ionizing gas.

Example 1

FIG. 3

Synthesis of 8a-c and 9a-c—General synthetic procedure. GB (2) or GC (3) (0.07 mmol) was dissolved in THF (4 mL) and KH (0.008 g, 0.24 mmol) was added at room temperature. The reaction mixture was stirred for 10 min., when a solution of 7a, 7b, or 7c (0.212 mmol) in THF (1 mL) was added dropwise. The reaction was stirred at room temperature for 4 hours. The solution was then cooled to 0° C. and concentrated HCl (0.3 mL) was added. The mixture was diluted with $H_2O$ (10 mL), extracted with EtOAc (3×10 mL) and washed with sat. aq. $NH_4Cl$-solution (30 mL), brine (30 mL) and water (30 mL). The organic phase was dried ($MgSO_4$) and removed in vacuo.

Purification. The crude material is purified by flash column chromatography using either A: CHCl$_3$/MeOH (100:1 and 50:1), B: CHCl$_3$/MeOH (30:1 and 20:1), or C: cyclohexane/acetone (3:1 and 2:1) giving a white solid.

10-O-benzophenone ginkgolide B (8a). Purified by method B. Yield: 0.035 g (78%). $^1$H NMR (400 MHZ, CD$_3$OD): δ 1.13 (s, tert-butyl), 1.24 (d, J=7.1, CH$_3$), 1.92 (dd, J=14.3, 4.5, 8-H), 2.07 (td, J=13.9, 4.4, 7α-H), 2.27 (dd, J=13.5, 4.6, 7β-H), 3.06 (q, J=7.1, 14-H), 4.31 (d, J=7.2, 1-H), 4.55 (d, J=7.2, 2-H), 4.85 (d, J=11.5, benzylic-H, 1H), 5.28 (s, 10-H), 5.42 (d, J=4.0, 6-H), 5.59 (d, J=11.5, benzylic-H, 1H), 6.15 (s, 12-H), 7.53-7.60 (m, Ar—H, 4H), 7.65-7.67 (m, Ar—H, 1H), 7.77-7.82 (m, Ar—H, 4H). $^{13}$C NMR (100 MHZ, CD$_3$OD): δ 7.25, 28.46 (3C), 32.18, 37.26, 42.29, 49.61, 68.21, 72.59, 72.80, 74.45, 76.76, 79.48, 83.53, 93.15, 99.78, 110.83, 127.96 (2C), 128.58 (2C), 130.03 (2C), 130.52 (2C), 132.94, 137.76 (2C), 141.67, 171.52, 172.70, 177.33, 196.45. HRMS: C$_{34}$H$_{34}$O$_{11}$ requires M+Na at m/z 641.1999, found 641.2018.

10-O-(trifluoromethyl-3H-diazirine)benzyl ginkgolide B (8b). Purified by method B. Yield: 0.024 g (59%). $^1$H NMR (400 MHz, CD$_3$OD): δ 1.11 (s, tert-butyl), 1.23 (d, J=7.1, CH$_3$), 1.89 (dd, J=14.3, 4.3, 8-H), 2.01 (td, J=13.9, 4.3, 7α-H), 2.25 (dd, J=13.4, 4.4, 7β-H), 3.05 (q, J=7.1, 14-H), 4.27 (d, J=7.3, 1-H), 4.53 (d, J=7.3, 2-H), 4.77 (d, J=11.2, benzylic-H, 1H), 5.24 (s, 10-H), 5.39 (d, J=3.9, 6-H), 5.51 (d, J=11.2, benzylic-H, 1H), 6.14 (s, 12-H), 7.29 and 7.53 (AA'BB' system, Ar—H, 4H). $^{13}$C NMR (75 MHz, CDCl$_3$): δ 7.67, 21.57 (q, $^2$J$_{CF}$=40.9, CCF$_3$), 29.56 (3C), 32.65, 37.49, 49.31, 68.07, 72.88, 73.57, 74.57, 76.56, 77.65, 80.08, 83.90, 90.90, 99.05, 110.68, 122.33 (q, $^1$J$_{CF}$=274.3, CF$_3$), 127.83 (2C), 129.53 (2C), 131.06, 136.44, 171.25, 171.50, 175.87. $^{19}$F NMR (282 MHz, CDCl$_3$): δ-66.23 (s, 3F). HRMS: C$_{29}$H$_{29}$F$_3$N$_2$O$_{10}$ requires M+1 at m/z 623.1853, found 623.1834.

10-O-tetrafluorobenzylazide ginkgolide B (8c). Purified by method B. Yield: 0.023 g (50%). $^1$H NMR (400 MHz, CDCl$_3$): δ 1.13 (s, tert-butyl), 1.32 (d, J=7.0, CH$_3$), 1.84-1.97 (m, 8-H and 7α-H), 2.27-2.33 (m, 7β-H), 2.84 (d, J=3.5, 1-OH), 2.99 (s, 3-OH), 3.06 (q, J=7.0, 14-H), 4.29 (dd, J=7.9, 3.5, 1-H), 4.61 (d, J=7.9, 2-H), 4.81 (d, J=10.7, benzylic-H, 1H), 4.94 (s, 10-H), 5.39 (d, J=3.4, 6-H), 5.64 (d, J=10.7, benzylic-H, 1H), 6.03 (s, 12-H); $^{13}$C NMR (100 MHz, CDCl$_3$): δ 7.70, 29.52 (3C), 32.62, 37.37, 42.03, 49.30, 61.21, 68.11, 72.79, 74.65, 80.07, 83.89, 91.00, 99.12, 108.95, 110.73, 139.71, 142.24, 144.45, 147.10, 170.69, 171.45, 175.83. $^{19}$F NMR (282 MHz, CDCl$_3$) δ-143.31 (m, 2F), -150.85 (m, 2F). HRMS: C$_{27}$H$_{25}$F$_4$N$_3$O$_{10}$ requires M+1 at m/z 628.1554, found 628.1565.

10-O-benzophenone ginkgolide C (9a). Purified by method A. Yield: 0.023 g (64%). $^1$H NMR (400, MHz, CD$_3$OD): δ 1.20 (s, tert-butyl), 1.24 (d, J=7.1, CH$_3$,), 1.78 (d, J=12.5, 8-H), 3.04 (q, J=7.1, 14-H), 4.21 (dd, J=12.5, 4.3, 7-H), 4.28 (d, J=7.0, 1-H), 4.54 (d, J=7.0, 2-H), 4.87 (d, J=11.6, benzylic-H, 1H), 5.13 (d, J=4.3, 6-H), 5.28 (s, 10-H), 5.60 (d, J=11.6, benzylic-H, 1H), 6.17 (s, 12-H) 7.53-7.61 (m, Ar—H, 4H), 7.65-7.67 (m, Ar—H, 1H), 7.77-7.83 (m, Ar—H, 4H). $^{13}$C NMR (100 MHz, CD$_3$OD): δ 7.34, 28.50 (3C), 32.12, 42.26, 50.00, 64.48, 67.40, 72.77, 74.28, 75.14, 76.74, 79.49, 83.55, 93.28, 99.54, 110.63, 127.95 (2C), 128.59 (2C), 130.03, 130.53 (2C), 132.96, 137.68 (2C), 141.65, 171.41, 172.55, 177.27, 197.03. HRMS: C$_{34}$H$_{34}$O$_{12}$ requires M+1 at m/z 635.2129, found 635.2098.

10-O-(trifluoromethyl-3H-diazirine)benzyl ginkgolide C (9b). Purified by method A. Yield: 0.023 g (51%). $^1$H NMR (400 MHz, CD$_3$OD): δ 1.17 (s, tert-butyl), 1.24 (d, J=7.1, CH$_3$,), 1.76 (d, J=12.5, 8-H), 3.02 (q, J=7.1, 14-H), 4.15 (dd, J=12.5, 4.3, 7-H) 4.24 (d, J=7.0, 1-H), 4.52 (d, J=7.0, 2-H), 4.79 (d, J=11.3, benzylic-H, 1H), 5.10 (d, J=4.3, 6-H), 5.23 (s, 10-H), 5.52 (d, J=11.3, benzylic-H, 1H), 6.15 (s, 12-H), 7.29 and 7.54 (AA'BB' system, aromatic-H, 4H). $^{13}$C NMR (75 MHz, CDCl$_3$): δ 7.65, 23.77 (q, $^2$J$_{CF}$=38.9, CCF$_3$), 29.52 (3C), 32.65, 41.94, 50.92, 64.43, 67.48, 73.89, 74.30, 76.03, 76.34, 79.63, 83.90, 90.91, 98.94, 110.53, 122.32 (q, $^1$J$_{CF}$=275.0, CF$_3$), 127.94 (2C), 129.68 (2C), 131.26, 136.07, 170.97, 171.07, 175.69. $^{19}$F NMR (282 MHz, CDCl$_3$): δ-66.23 (s, 3F). HRMS: C$_{29}$H$_{29}$F$_3$N$_2$O$_{11}$ requires M+1 at m/z 639.1802, found 639.1790.

10-O-tetrafluorobenzylazide ginkgolide C (9c). Purified by method C. Yield: 0.080 g (54%). $^1$H NMR (400 MHz, CDCl$_3$): δ 1.22 (s, tert-butyl), 1.33 (d, J=7.0, CH$_3$,), 1.71 (d, J=12.4, 8-H), 2.33 (d, J=10.6, 7-OH), 2.88 (d, J=3.4, 1-OH), 3.01 (s, 3-OH), 3.08 (q, J=7.0, 14-H), 4.08 (m, 7-H) 4.27 (dd, J=7.8, 3.4, 1-H), 4.62 (d, J=7.8, 2-H), 4.83 (d, J=10.7, benzylic-H, 1H), 4.96 (s, 10-H), 5.09 (d, J=4.4, 6-H), 5.58 (d, J=10.7, benzylic-H, 1H), 6.04 (s, 12-H). $^{13}$C NMR (75 MHz, CDCl$_3$): δ 7.64, 29.42 (3C), 32.59, 42.08, 50.64, 51.16, 61.47, 64 35, 67.32, 74.27, 75.88, 79.64, 83.88, 91.26, 99.14, 110.71, 120-150 (m, 6C), 170.72, 171.17, 176.29. $^{19}$F NMR (282 MHz, CDCl$_3$): δ-143.56 (m, 2F), -151.08 (m, 2F); HRMS: C$_{27}$H$_{25}$F$_4$N$_3$O$_{11}$, requires M+1 at m/z 644.1503, found 644.1527.

Example 2A

FIG. 4

10-O-benzophenone-7-O-dansyl ginkgolide C (10a). A solution of dansyl chloride (0.010 g, 0.035 mmol) in acetonitrile (0.3 mL) was added to a solution of 9a (0.020 g, 0.032 mmol) and DMAP (0.008 g, 0.063 mmol) in acetonitrile (1.5 mL). The reaction mixture was stirred for 16 h at room temperature, then a sat. aq. NH$_4$Cl0-solution (2 mL) was added, and the mixture was extracted with EtOAc (3×5 mL). The combined organic phases were washed with sat. aq. NaCl-solution (3×15 mL), dried (MgSO$_4$) and removed in vacuo. The crude product was purified by flash column chromatography eluting with cyclohexane/acetone (2:1) to give the product as a slightly yellow solid (0.015 g, 56%). $^1$H NMR (400 MHz, DMSO-d$_6$): δ 0.83 (s, tert-butyl), 1.09 (d, J=7.2, CH$_3$,), 1.94 (d, J=12.5, 8-H), 2.81 [m, 14-H and N(CH$_3$)$_2$], 4.26 (t, J=5.3, 1-H), 4.53 (d, J=5.4, 2-H), 4.79 (d, J=13.2, benzylic-H, 1H), 4.89 (dd, J=12.5, 4.0, 7-H), 5.19 (d, J=4.0, 6-H), 5.23 (s, 10-H), 5.46 (d, J=13.2, benzylic-H, 1H), 6.07 (d, J=5.3, 1-OH), 6.21 (s, 12-H), 6.51 (s, 3-OH), 7.28-7.30 (m, Ar—H, 1H), 7.50-7.70 (m, Ar—H, 7H), 7.79-7.82 (m, Ar—H, 4H), 8.18-8.20 (m, Ar—H, 2H), 8.54-8.56 (m, Ar—H, 1H); ). HRMS: C$_{46}$H$_{45}$NO$_{14}$S requires M+1 at m/z 868.2639, found 868.2642.

Example 2B

10-O-benzophenone-1-O-dansyl ginkgolide C (10b). Synthesized as 10a, but using 2 equivalents of dansyl chloride (instead of 1.1 equivalent) give rise to a 1:1 mixture of 10a and 10b. The two products were separated on analytical TLC giving 10b (0.008 g, 30%) as a slightly yellow solid. $^1$H NMR (400 MHz, DMSO-d$_6$): δ 0.91 (s, tert-butyl), 1.16 (d, J=7.6, CH$_3$,), 1.78 (d, J=12.5, 8-H), 2.80 [s, N(CH$_3$)$_2$], 2.97 (q, J=7.6, 14-H), 4.22 (d, J=3.8, 1-H), 4.26 (m, 7-H), 4.57 (d, J=3.9, 6-H), 4.80 (d, J=13.2, benzylic-H, 1H), 5.20 (d, J=3.8, 2-H), 5.30 (s, 10-H), 5.31 (d, J=4.9, 7-OH), 5.49 (d, J=13.2, benzylic-H, 1H), 5.95 (s, 12-H), 5.98 (s, 3-OH), 7.25-7.27 (m, Ar—H, 1H), 7.54-7.79 (m, Ar—H, 11H), 8.18-8.24 (m, Ar—H, 2H), 8.47-8.49 (m, Ar—H, 1H);). HRMS: $C_{46}H_{45}NO_{14}S$ requires M+1 at m/z 868.2639, found 868.2668.

Example 3

FIG. 5

10-O-benzoylbenzoic ginkgolide C (11). 4-Benzoylbenzoic acid (0.018 g, 0.08 mmol) and 2 (0.028 g, 0.07 mmol) was dissolved in THF (5 mL), and the mixture cooled to 0° C. 1-[3-(Dimethylamino)propyl]-3-ethylcarbodiimide HCl (EDC) (0.018 g, 0.092 mmol) and DMAP (0.002 g, 0.01 mmol) was added, and the reaction mixture stirred at 0° C. for 1 h, and continued overnight at room temperature. The solvent was removed in vacuo, the crude product dissolved in EtOAc (20 mL), and washed with a sat. 5% $NaHCO_3$-solution (20 mL) and brine (20 mL). The organic fraction was dried ($MgSO_4$) and the solvent evaporated in vacuo. The crude product was purified by flash column chromatography eluting with hexane/EtOAc (2:1) to give the product as white crystals (0.026 g, 62%). $^1H$ NMR (400 MHz, $CD_3OD$): δ 1.07 (s, tert-butyl), 1.26 (d, J=7.1, $CH_3$), 1.98-2.10 (m, 8-H and 7α-H), 2.30-2.36 (m, 7β-H), 3.12 (q, J=7.1, 14-H), 4.37 (d, J=6.5, 1-H), 4.55 (d, J=6.5, 2-H), 5.66 (d, J=3.2, 6-H), 6.32 (s, 10-H), 6.45 (s, 12-H), 7.54-7.58 (m, Ar—H, 2H), 7.67-7.69 (m, Ar—H, 1H), 7.80-7.83 (m, Ar—H, 2H), 7.86-7.88 (m, Ar—H, 2H), 8.42-8.44 (m, Ar—H, 2H). $^{13}C$ NMR (100 MHz, $CD_3OD$): δ 7.42, 28.22 (3C), 32.16, 37.27, 42.29, 49.42, 67.81, 70.64, 72.74, 74.42, 79.29, 83.64, 95.13, 100.51, 111.12, 128.73 (2C), 129.92 (2C), 130.17 (2C), 130.58 (2C), 131.61, 133.41, 137.06, 142.66, 164.56, 168.93, 171.41, 177.33, 196.48. HRMS: $C_{34}H_{31}O_{12}$ requires M+Na at m/z 655.1791, found 655.1790.

Example 4A

FIG. 6

7-trifluoromethanesulfonyloxy ginkgolide B (12). Trifluoromethanesulfonic anhydride (0.2168 mL, 1.281 mmol) was added dropwise to a cooled solution of $CH_2Cl_2$ (2.84 mL) and pyridine (0.115 mL, 1.405 mmol) at −20° C. The solution was added dropwise to a solution of 3 (0.500 g, 1.134 mmol) in pyridine (4.83 mL) and the reaction was stirred for 2 hours at −20°. The reaction mixture was heated to room temperature and the solvent was in vacuo. The residue was dissolved in EtOAc (30 mL) and washed with 1M HCl (30 mL), and an aqueous, saturated NaCl solution (30, mL). The organic phase was dried ($MgSO_4$), then treated with activated carbon and filtered through Celite. The solvent was removed in vacuo and remaining solid was precipitated from heptane/methyl tert-butyl ether (2:1) to give a colorless solid. The solid was purified by flash column chromatography eluting with $CHCl_3$/MeOH/EtOAc (30:1:1, 20:1:1, 10:1:1) give the product as white crystals (0.61 g, 93%). $^1H$ NMR (400 MHz, DMSO-$d_6$): δ 1.11 (s, tert-butyl), 1.13 (d, J=9.6 Hz, $CH_3$,), 2.22 (d, J=16.5, 8-H), 2.82 (q, J=9.6 Hz, 14-H), 4.15 (dd, J=8.0, 5.9 Hz, 1-H), 4.73 (d, J=8.0 Hz, 2-H), 5.08 (d, J=7.4 Hz, 10-H), 5.24 (dd, J=16.5, 5.6 Hz, 7-H) 5.41 (d, J=5.6 Hz, 6-H), 5.54 (d, J=5.9 Hz, 1-OH), 6.20 (s, 12-H), 6.62 (s, 3-OH), 7.63 (d, J=7.4 Hz, 10-OH). $^{13}C$ NMR (100 MHz, DMSO-$d_6$): δ 9.1, 29.2 (3C), 32.6, 42.1, 49.0, 64.2, 68.1, 69.4, 74.4, 75.2, 84.0, 86.3, 93.2, 99.9, 109.4, 118.6 (q, $^1J_{CF}$=316.6, $CF_3$), 173.9, 176.9, 179.2. HRMS: $C_{21}H_{23}F_3O_{13}S$ requires M+1 at m/z 573.0890, found 573.0872.

Example 4B

7-Fluoro ginkgolide B (13). 7-trifluoromethanesulfonyloxy-ginkgolide B (12) (0.035 g, 0.061 mmol) and tetrabutylammonium fluoride hydrate (0.038 g, 0.145 mmol) were dissolved in acetonitrile (0.2 mL) and heated at 80° C. for 30 min. The crude product was applied on an HPLC semi-preparative C18 column (7.8 mm×30 cmL) with a mobile phase of MeOH/$H_2O$ (40:60) at a flow of 2 mL/min. The HPLC purified product was purified by flash column chromatography eluting with $CHCl_3$/MeOH (25:1) to give the final product as a white solid (0.016 g, 60%). $^1H$ NMR (400 MHz, $CD_3OD$): δ 1.25 (s, tert-butyl), 1.26 (d, J=7.1, $CH_3$), 1.94 (dd, $J_{HF}$=45.5, J=2.3, 8-H), 3.05 (q, J=7.1, 14-H), 4.24 (d, J=8.0, 1-H), 4.59 (d, J=8.0, 2-H), 5.18 (s, 10-H), 5.35 (d, $J_{HF}$=10.9, 6-H), 5.38 (dd, $J_{HF}$=48.8, J=2.3, 7-H), 6.14 (s, 12-H). $^{13}C$ NMR (75 MHz, $CD_3OD$): δ 7.0, 29.5 (3 C), 32.9, 42.4, 53.7 ($^2J_{CF}$=20.4), 68.8, 69.1, 71.5, 74.5, 79.5 ($^2J_{CF}$=36.0), 83.7, 91.7, 96.9 ($^1J_{CF}$=184.2), 98.8, 111.6, 171.2, 173.9, 177.1. HRMS: $C_{20}H_{23}FO_{10}$ requires M+1 at m/z 443.1354, found 443.1370.

Example 4C

10-O-Methyl ginkgolide B (14). To a suspension of ginkgolide B (0.030 g, 0.071 mmol) and $K_2CO_3$ (0.030 g, 0.212 mmol) in acetonitrile (0.5 mL) was added iodomethane (0.020 g, 0.141 mmol): The reaction mixture was heated under reflux for 30 min. This reaction resulted in a mixture of 10-methoxy-ginkgolide B and 1-methoxy ginkgolide B in a ratio of 4 to 1. 10-Methoxy-ginkgolide B was separated using an HPLC semi-preparative C18 column (7.8 mm×30 cmL) with a mobile phase of MeOH/$H_2O$ (40:60) at a flow of 2 mL/min to give the final product as a white solid (0.017 g, 56%). $^1H$ NMR (400 MHz, $CD_3OD$): δ 1.14 (s, tert-butyl), 1.24 (d, J=7.1, $CH_3$), 1.90 (dd, J=14.2, 4.6, 8-H), 2.06 (td, J=13.9, 4.3, 7α-H), 2.25 (dd, J=13.6, 4.6, 7β-H), 3.05 (q, J=7.1, 14-H), 3.80 (s, $OCH_3$), 4.24 (d, J=7.4, 1-H), 4.57 (d, J=7.4, 2-H), 4.93 (s, 10-H), 5.43 (d, J=4.1, 6-H), 6.10 (s, 12-H). $^{13}C$ NMR (75 MHz, $CD_3OD$): δ 7.6, 7.0, 29.6 (3 C), 32.9, 37.6, 41.8, 48.8, 68.6, 70.5, 71.5, 74.4, 80.4, 82.2, 84.8, 90.9, 98.2, 110.3, 171.1, 173.0, 175.4. [Hu, L., Chen, Z., Xie, Y., Jiang, Y., & Zhen, H. (2000) *Bioorg. Med. Chem.* 8, 1515-1521]

Example 4D

10-O-(2-Fluoroethyl)ginkgolide B (15). Ginkgolide B (2) (0.031 g, 0.073 mmol) and 1-bromo-2-fluoroethane (0.102 g, 0.803 mmol) were dissolved in acetonitrile/DMF (4:1 0.25 mL) and heated at 80° C. for 30 min in the presence of tetrabutylammonium hydroxide (1M in MeOH, 0.125 mL). The crude product was a mixture of 10-fluoroethoxy ginkgolide B and 1-fluoroethoxy ginkgolide B in a 5 to 1 ratio (as determined by $^1H$ NMR). The crude product was applied on an HPLC semi-preparative C18 column (7.8 mm i.d.×30 cmL) with a mobile phase of MeOH/$H_2O$ (50:50) at a flow of 2 mL/min The HPLC purified product was purified by flash column chromatography eluting with $CHCl_3$/MeOH (50:1 and 25:1) to give the final product as a white solid (0.022 g, 63%). $^1H$ NMR (400 MHz, $CD_3OD$): δ 1.14 (s, tert-butyl), 1.25 (d, J=7.1, $CH_3$), 1.93 (dd, J=14.3, 4.7, 8-H), 2.10 (td, J=14.0, 4.3, 7α-H), 2.28 (dd, J=13.6, 4.7, 7β-H), 3.05 (q, J=7.1, 14-H), 3.90-4.01 (m, 1H, $FCH_2CH_2O$), 4.27 (d, J=7.4, 1-H), 4.53-4.78 (m, 3H, $FCH_2CH_2O$), 4.60 (d, J=7.4, 2-H), 5.15 (s, 10-H), 5.45 (d, J=4.1, 6-H), 6.13 (s, 12-H). $^{13}C$ NMR (75 MHz, $CD_3OD$): δ 7.1, 28.4 (3 C), 32.1, 37.1, 42.3, 49.6, 68.1, 70.4 ($^2J_{CF}$=21.0), 72.7, 74.5, 77.8 ($^1J_{CF}$=182.6), 81.7, 83.4, 83.9, 92.9, 99.6, 110.8, 171.5, 172.6, 177.3. HRMS: $C_{22}H_{27}FO_{10}$ requires M+1 at m/z 471.1667, found 471.1687.

Example 5

FIG. 7

Synthesis of [$^3$H]-Ginkgolide B

Initially, nBu$_4$NB$^3$H$_4$ was synthesized as follows:

NaB$^3$H$_4$ (4.69 mg, 100 µmol specific activity 100 Ci/mmol, total activity 100 mCi) and NaOH (0.20 mg, 5 µmol) is dissolved in $^3$H$_2$O (100 µL, specific activity 5 Ci/g, total activity 500 mCi) in a vial. nBu$_4$NCl (18.53 mg, 66.7 µmol) in $^3$H$_2$O (100 µL, specific activity 5 Ci/g, total activity 500 mCi) is added and the reaction mixture is stirred for 1 min. CH$_2$Cl$_2$ (500 µL) is added to the vial, the mixture is shaken, the water layer is removed, MgSO$_4$ is added and the suspension stirred. The CH$_2$Cl$_2$ solution is filtered through MgSO$_4$ (in a syringe) into vial, and the solvent is removed by flowing nitrogen over the solution, and heating.

Figure 7:
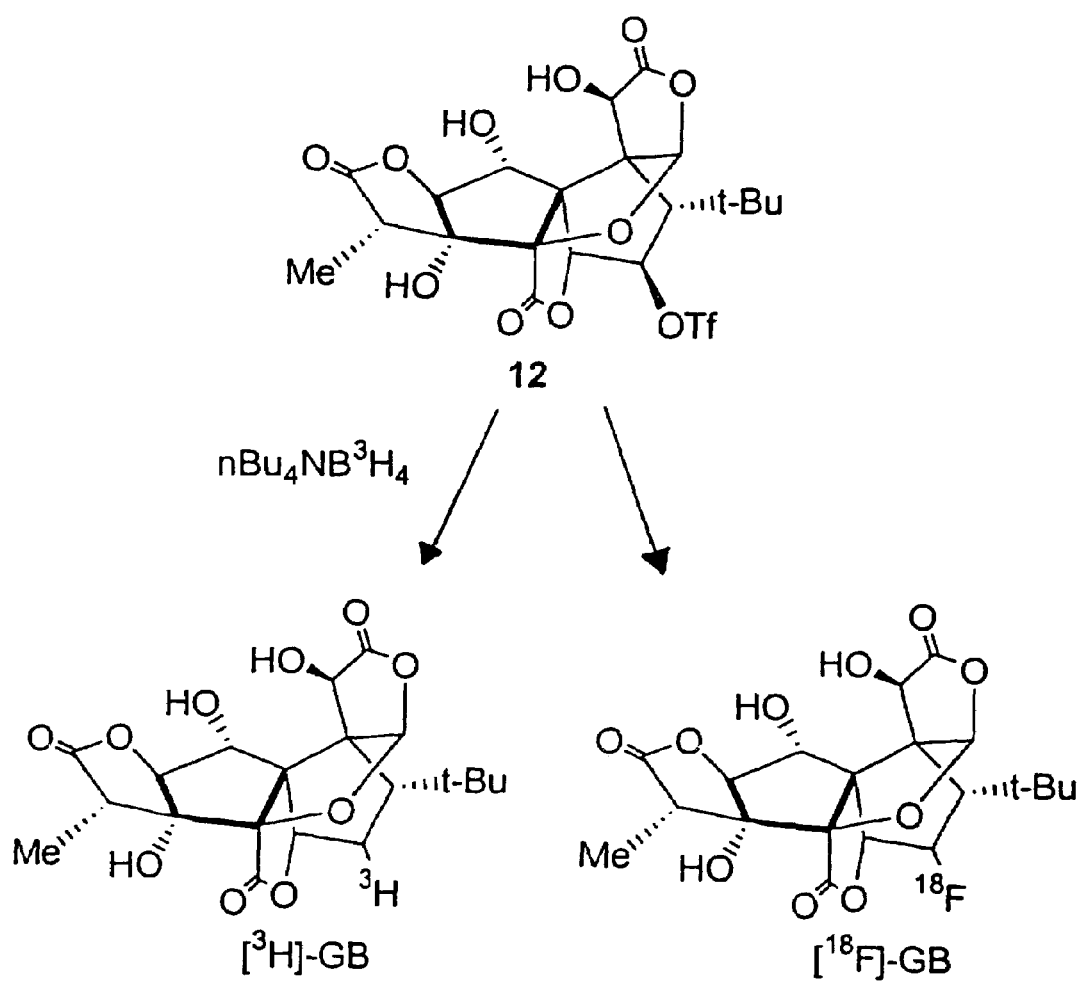
FIG. 7. [$^3$H]-Ginkgolide B ([$^3$H]-GB).

Then, the synthesis of [$^3$H]-Ginkgolide B followed (FIG. 7).

nBu$_4$NB$^3$H$_4$ (1.1 mg) in dry THF (20 µL) is added to a solution of 7-triflate-Ginkgolide C (14.5 mg, in dry THF (100 µL) precooled to 0° C. The mixture is stirred for 1.5 h at room temperature. MeOH (25 µL) is added, the mixture is shaken, and the solvent removed by flowing nitrogen over the solution, and heating. The residue is dissolved in acetonitrile (50 µL) and a mixture of H$_2$0/CH$_3$CN (1:1, 50 µL), and the solution is injected into the (preparative) HPLC (the product has a retention time of ca. 9.6 min.). Fractions is collected every 30 s (until 8 min.) then every 20 s, and an aliquot (5 µL) is taken into a scintillation vial, scintillation liquid is added and the vials is placed in a scintillation counter. Fractions corresponding to the peak of [$^3$H]-GB are collected and diluted with water, and passed through a C18 Sep-pak column, that is washed with water and [$^3$H]-GB is eluted with absolute ethanol into a vial, and the solvent is removed to give the product as a white solid (total activity 2.4 mCi, specific activity 3.8 mCi/µmol).

Example 6

Bilobalide (6) derivatives. Bilobalide derivatives having modifications at the 10-OH corresponding position are prepared following the procedures used herein to prepare Ginkgolide derivatives having modifications at the 10-OH position. Derivatization of Bilobalide (BB, 6) is performed as follows:

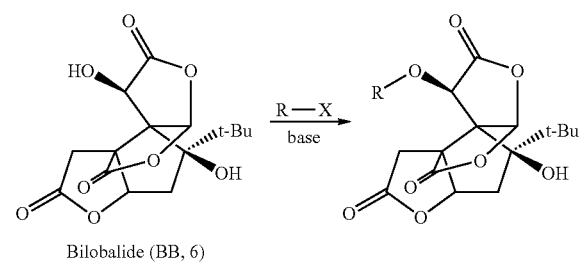

Bilobalide (BB, 6)
X = leaving group
R = any alkyl, phenyl etc. group

Methods

Synthesis

For the synthesis of derivatives with variation at C-7, a useful intermediate was 7β-OTf-GB (16). GC (2) reacted with high selectivity at 7-OH with trifluoromethanesulfonic (Tf) anhydride giving 16 in very high yield, with no reactions occurring at other hydroxyl groups (Teng, B.-P., U.S. Pat. No. 5,599,950). This selectivity is noteworthy, as 10-OH, and in some cases 1-OH, of GC (2) is generally the more reactive hydroxyl group (U.S. Pat. No. 5,541,183; Hu, 2000), although we recently observed higher reactivity of 7-OH when acetylation was performed under strong acidic conditions (Jaracz, 2002).

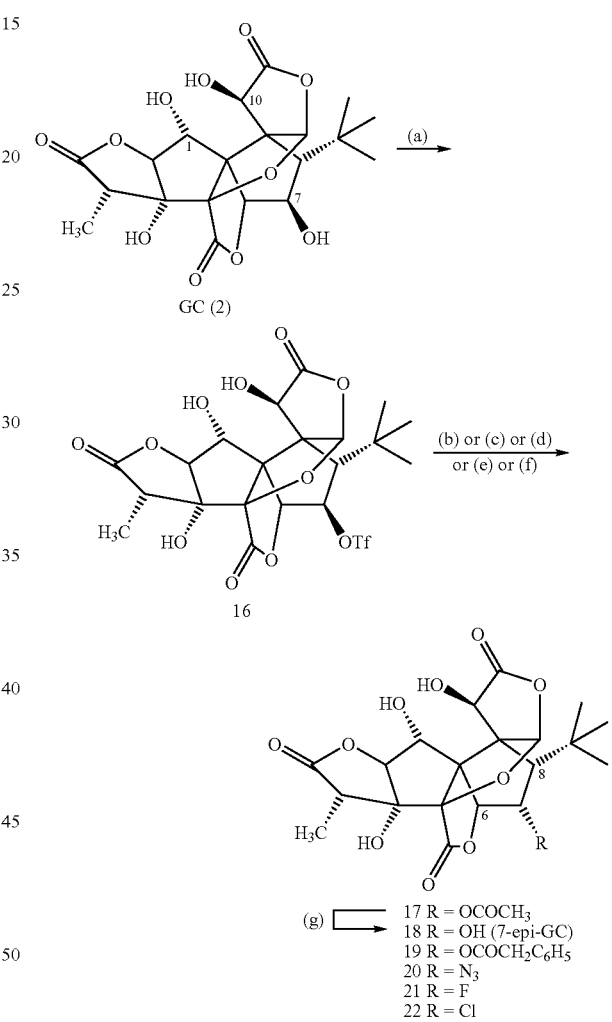

Scheme 1. Reagents:
(a) Tf$_2$O, Pyridine, CH$_2$Cl$_2$;
(b) NaOCOCH$_3$, DMSO;
(c) NaOCOCH$_2$C$_6$H$_5$, DMSO;
(d) NaN$_3$, DMSO;
(e) TBAF, CH$_3$CN;
(f) TBACl, CH$_3$CN;
(g) 2N NaOH.

7β-OTf-GB (16) was reacted with various nucleophiles as depicted in Scheme 1 to give derivatives 17-22. The inverted configuration at C-7 was reflected by considerable changes in coupling constants in $^1$H NMR spectra, i.e., $^3J_{7,8}$ and $^3J_{6,7}$ are 12 and 4 Hz in GC (2), whereas they are 3-5 Hz and ca. 0 Hz, respectively, when the configuration at C-7 is inverted. The reactions shown in Scheme 1 generally proceeded in good yield, but in several other cases the nucleophilic substitution did not proceed as expected. When reacting with a soft nucleophile such as NaSCN only starting material was recovered. Increase in the basicity of the nucleophiles, as in NaCN and aliphatic amines, resulted in a complex mixture of products, probably due to reaction at C-11, as previously described (Hu, 2001). In addition to the presence of multiple electrophilic sites in 16 it is believed that the steric hindrance of the bulky tert-butyl group, which is in close proximity to the reaction site, is responsible for lack of reaction. This assumption is corroborated by reaction of 16 with halogens; incorporation of fluorine (7α-F-GB, 21) proceeded in high yield, chlorine (7α-Cl-GB, 22) in slightly lower yield, whereas the larger bromine was introduced in trace amounts only, while no iodine product could be detected. These results were not affected by changing the solvent or the halide counterion.

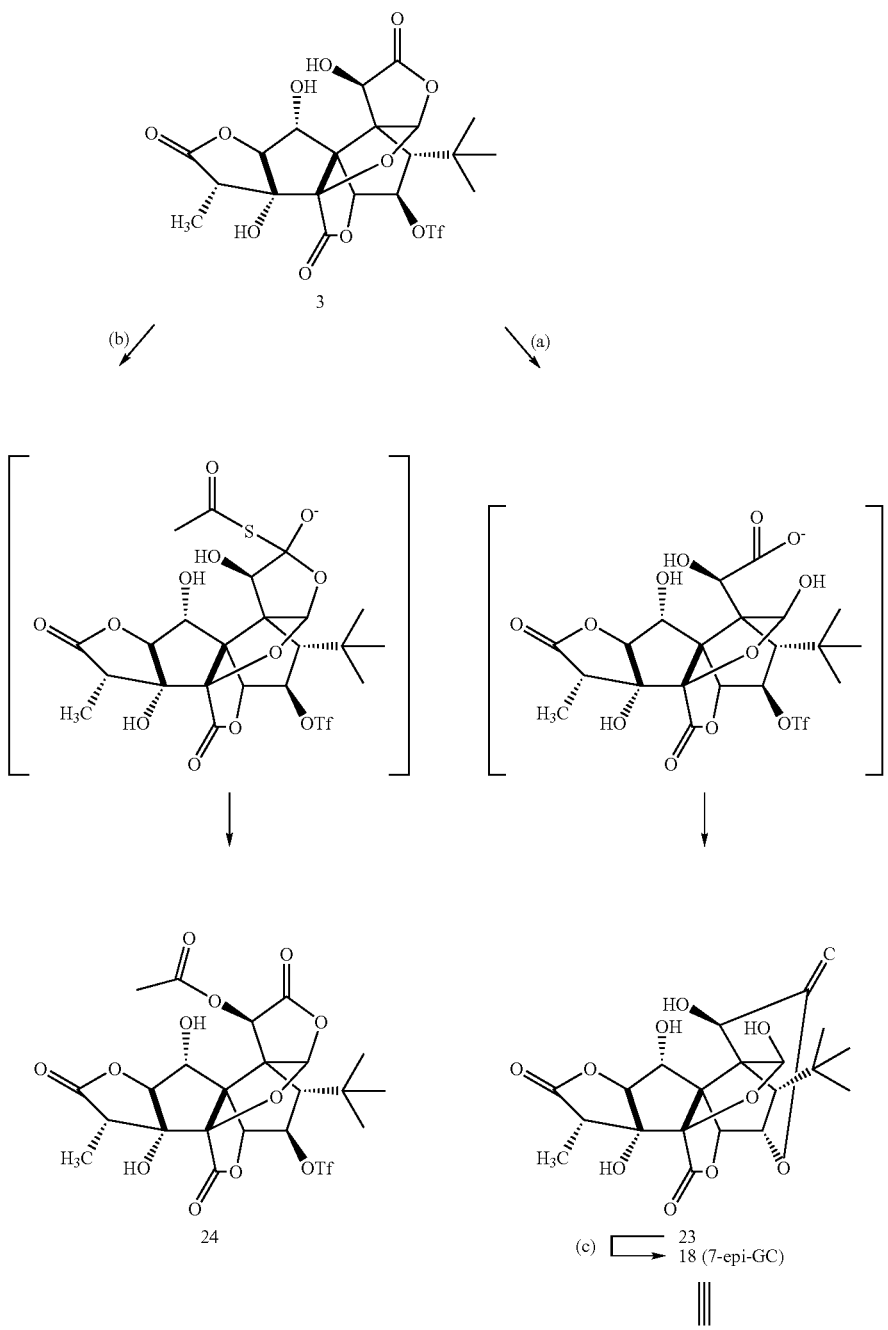

-continued

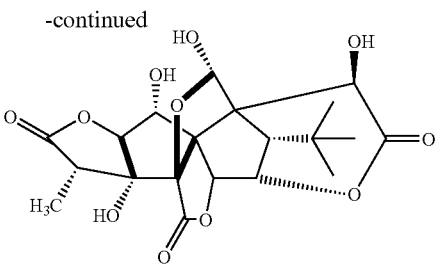

Scheme 2: Reagents:
(a) MeOH, 2,6-lutidine;
(b) KSCOCH₃ DMF;
(c) 1M NaOH, acidic work-up Steric hindrance may also be the prerequisite for two remarkable products arising from reaction of triflate 16 with MeOH and NaSCOCH₃, respectively (Scheme 2). In the former case 16 was dissolved in MeOH and 2,6-lutidine, and reacted for three days at 70° C. expecting to provide 7α-OMe-GB; instead a new product with a molecular weight similar to GC (2), but with a different ¹H NMR spectrum was obtained. Extensive NMR studies revealed a new relactonized structure, neoginkgolide C (23) (Scheme 2), arising from opening of lactone C, followed by displacement of the triflate group. The structure of this compound 23 with a new rearranged ginkgolide skeleton not encountered earlier was determined by high resolution mass spectrometry, rotating frame nuclear Overhauser and exchange spectroscopy (ROESY), correlation spectroscopy (COSY) and heteronuclear single-quantum coherence (HSQC) NMR experiments (see Supporting Information). Moreover, treatment of compound neoginkgolide C (23) with 1 M NaOH followed by acidic work-up resulted in a clean conversion to the thermodynamically more favorable 7-epi-GC (18). The reaction between triflate 16 and NaSCOCH₃ did not give the expected 7α-SCOCH₃-GB, but instead the 10-acetate, while the 7-triflate group remained intact to give 24 (Scheme 2). This product might arise from a reaction by thioacetate at C-11, followed by a transfer of the acetate to 10-OH, tautomerization to thionic acid and relactonization to give the final product (Scheme 2).

TABLE 3

Reduction of 7α-N₃-GC (20) in different solvents.

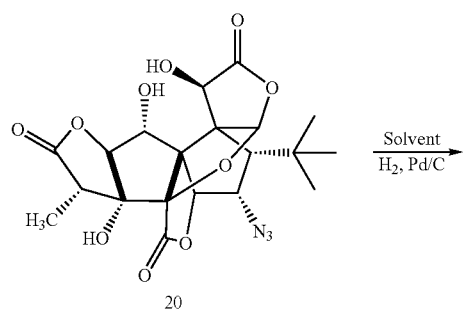

TABLE 3-continued

| Compound | Solvent | R | Yield (%)ᵃ |
|---|---|---|---|
| 25 | MeOH | CH₃ | 95 |
| 26 | EtOH | CH₂CH₃ | 68 |
| 27 | THF | H | 98 |

ᵃIsolated yield (after flash chromatography)

Another interesting feature was the reduction of azide 20 using Pd/C in MeOH under hydrogen. The reaction did not provide the expected amine, but instead gave N-methylamine 25 in quantitative yield (Table 3). To investigate this further, the reaction was carried out in EtOH, which gave N-ethyl amine 26 as the major product. The desired primary amine 27 was obtained when THF was used as solvent (Table 3). This intriguing reaction might provide a convenient way to convert azides directly into various alkylamines, an aspect which is under further investigation.

For the synthesis of 7-epi-GC (18) (Scheme 1) various approaches were attempted; GC (2) and 4-nitrobenzoic acid was treated with diethyl azodicarboxylate (DEAD) and Ph₃P in a Mitsunobu reaction, but no reaction was observed. Instead, 7β-OTf-GB (16) was reacted with KNO₂ and 18-crown-6 ether in a reaction that could potentially lead to 7-epi-GC (18) directly from 16 (Moriarty, 1993), but only starting material was recovered. Instead, the inversion of 7-OH of GC (2) was accomplished using acetate as the nucleophile, followed by basic hydrolysis of the acetate. Acetylation of 7β-OTf-GB (16) was achieved by reaction with NaOAc; attempts to use the more reactive CsOAc led to decomposition of 16, while using CsOCCF₃ did not lead to any reaction. The hydrolysis was accomplished by treating 17 with 2N NaOH to give 7-epi-GC (18) in 95% yield (Scheme 1).

To further investigate the importance of stereochemistry at C-7, we planned a series of corresponding 7β-substituted derivatives. Thus 7-epi-GC (18) was reacted with Tf anhydride, but only starting material was recovered. This lack of reaction is most likely due to a change in steric environment of 7α-OH, relative to 7β-OH, due to the tert-butyl group.

Finally, the observation that an aromatic substituent at 10-OH of GB (1) and GC (2) increases the antagonistic effect at PAFR (U.S. Pat. No. 5,541,183; Hu, 2000; Strømgaard, 2002) led us to investigate whether a similar increase would be observed for 7α-GB derivatives. Benzylated derivatives 28-31 (Table 5) were therefore prepared, following previously described procedures (U.S. Pat. No. 5,541,183; Hu, 2000).

Detailed Synthetic Procedure

GB (1) and GC (2) was obtained by extraction of leaves from *G. biloba*, purification by column chromatography and recrystallization as previously described (Lichtblau, 2002; van Beek, 1997). The purity was >98% as estimated by $^1$H NMR. Unless otherwise noted, materials were obtained from a commercial supplier and were used without further purification. Solvents were dried by eluting through alumina columns. Flash column chromatography was performed using ICN silica gel (32-63 mesh). Thin-layer chromatography was carried out using pre-coated silica gel 60 $F_{254}$ plates with thickness of 0.25 mm. Plates were heated and spots were detected by monitoring at 254 nm. $^1$H and $^{13}$C NMR spectra were obtained on Bruker DMX 300 MHz or Bruker DMX 400 MHz spectrometers and are reported in parts per million (ppm) relative to internal solvent signal, with coupling constants (J) in Hertz (Hz). HSQC, COSY and ROESY spectra were obtained on a Bruker DMX 400 MHz or Bruker DMX 500 MHz spectrometer. Analytical and preparative high performance liquid chromatography (HPLC) were performed on a HP 1100 LC instrument with detection by UV at 219 and 254 nm. Preparative HPLC was performed using a 10 μm C18 reversed-phase VYDAC column (250×22 mm) with a flow of 4 ml/min and eluting with either eluent A or B. A: water/ $CH_3CN$/TFA (60:40:0.1), raising to (40:60:1) after 20 min. B: water/$CH_3CN$/TFA (65:35:0.1), raising to (40:60:1) after 20 min. Analytical HPLC were performed using a 5 μm C18 reversed-phase Phenomenex Luna column (150×4.60 mm), with a flow of 1 mL/min eluting with water/$CH_3CN$/TFA 70:30:0.1. Compounds 18 and 23 were eluted with water/$CH_3CN$/TFA 80:20:0.10 and compounds 25-27 with water/$CH_3CN$ 90:10. Accurate mass determinations were performed on a JEOL JMS-HX110/100A HF mass spectrometer using a 3-nitrobenzyl alcohol (NBA) matrix and Xe ionizing gas, and are within ±10 ppm of theoretical values. All were crystalline compounds that decompose above 200° C.

Example 7

7-Trifluoromethanesulfonyloxy Ginkgolide B (16). In a mixture of dry $CH_2Cl_2$ (1.0 mL) and dry pyridine (1.5 mL) GC (2) (184 mg, 0.42 mmol) was dissolved. The solution was cooled to −20° C. under argon and trifluoromethanesulfonic anhydride (78 μL) was added dropwise. The reaction was stirred at −20° C. for 2 h and allowed to warm to room temperature over 1 h. The solvent was removed in vacuo, and the residue was dissolved in EtOAc (30 mL) and washed with 1 N HCl (3×20 mL), brine (10 mL), dried (MgSO$_4$) and the solvent removed in vacuo. The crude product was purified by flash chromatography eluting with CHCl$_3$/CH$_3$OH/EtOAc (30:1:1 and 20:1:1) to obtain 3 as white crystals (232 mg, 97%). $^1$H NMR (400 MHz, DMSO-d$_6$): δ 1.11 (s, tert-butyl), 1.13 (d, J=9.6, CH$_3$), 2.22 (d, J=16.5, 8-H), 2.82 (q, J=9.6, 14-H), 4.15 (dd, J=8.0, 5.9, 1-H), 4.73 (d, J=8.0, 2-H), 5.08 (d, J=7.4, 10-H), 5.24 (dd, J=16.5, 5.6, 7-H) 5.41 (d, J=5.6, 6-H), 5.54 (d, J=5.9, 1-OH), 6.20 (s, 12-H), 6.62 (s, 3-OH), 7.63 (d, J=7.4, 10-OH). $^{13}$C NMR (100 MHz, DMSO-d$_6$): δ 9.1, 29.2 (3C), 32.6, 42.1, 49.0, 64.2, 68.1, 69.4, 74.4, 75.2, 84.0, 86.3, 93.2, 99.9, 109.4, 118.6 (q, $^1J_{CF}$=316.6, CF$_3$), 173.9, 176.9, 179.2. HRMS: $C_{21}H_{23}F_3O_{13}S$ requires M+1 at m/z 573.0890; found, 573.0872.

Example 8

7α-O-Acetate Ginkgolide B (17). Sodium acetate (163 mg, 1.99 mmol) and 16 (228 mg, 0.39 mmol) were dissolved in DMSO (3 mL) and the solution was stirred at 65° C. for 17 h. The solvent was removed in vacuo, and the residue was partitioned between 1 N HCl (20 mL) and EtOAc (25 mL). The aqueous phase was extracted with EtOAc (3×25 mL) and the combined organic phases were washed with brine (2×10 mL), dried (MgSO$_4$), and the solvent removed in vacuo. The crude product was purified by flash chromatography eluting with CHCl$_3$/EtOAc/MeOH (10:1:1) to obtain 17 as white crystals (144 mg, 75%). A portion (20 mg) of this was recrystallized (MeOH/H$_2$O) for pharmacological evaluation (9 mg). $^1$H NMR (400 MHz, DMSO-d$_6$): δ 1.12 (d, J=7.1, CH$_3$), 1.10 (s, tert-butyl), 1.91 (d, J=3.3, 8-H), 2.06 (s, COCH$_3$), 2.84 (q, J=7.1, 14-H), 4.03 (dd, J=7.7, 3.6, 1-H), 4.66 (d, J=7.7, 2-H), 4.86 (d, J=3.6, 1-OH), 5.01 (s, 6-H), 5.15 (d, J=6.8, 10-H), 5.25 (d, J=3.3, 7-H), 6.16 (s, 12-H), 6.52 (s, 3-OH), 7.42 (d, J=6.8, 10-OH). $^{13}$C NMR (100 MHz, CD$_3$OD): δ 8.0, 21.0, 30.7 (3C), 33.8, 43.4, 53.2, 70.1, 70.3, 72.5, 75.3, 79.6, 80.9, 84.6, 92.6, 99.8, 112.7, 171.3, 171.5, 175.0, 178.1. HPLC-UV: 96%. HRMS: $C_{22}H_{27}O_{12}$ requires M+1 at m/z 483.1503; found, 483.1525.

Example 9

7α-O-Phenylacetate Ginkgolide B (19). Sodium phenylacetate (44 mg, 0.28 mmol) and 16 (32 mg, 0.07 mmol) were dissolved in DMSO (0.8 mL) and heated at 65° C. for 5 h and the solvent was removed in vacuo, and the residue was partitioned between 1 N HCl (10 mL) and EtOAc (15 mL) and the aqueous phase was extracted with EtOAc (3×15 mL). The combined organic phases were washed with 1 N HCl (2×10 mL), water (5×10 mL) and brine (2×10 mL), dried (MgSO$_4$) and the solvent removed in vacuo. The crude product was purified by flash column chromatography eluting with CHCl$_3$/MeOH/EtOAc (30:1:1), recrystallized (MeOH) and further purified by preparative HPLC (eluent A) to give 5 (10 mg, 26%) as white crystals. $^1$H NMR (400 MHz, DMSO-d$_6$): δ 1.07 (s, tert-butyl), 1.12 (d, J=6.9, CH$_3$), 1.93 (d, J=2.9, 8-H), 2.84 (q, J=6.9, 14-H), 3.70 (s, CH$_2$), 4.04 (dd, J=3.6, 7.7, 1-H), 4.62 (d, J=7.7, 2-H), 4.72 (d, J=3.6, 1-OH), 4.99 (s, 6-H), 5.16 (d, J=6.6, 10-H), 5.26 (d, J=2.9, 7-H), 6.16 (s, 12-H), 6.48 (s, 3-OH), 7.25-7.35 (m, aromatic, 5H) 7.46 (d, J=6.6, 10-OH). $^{13}$C NMR (100 MHz, CD$_3$OD): δ 8.0, 30.8 (3C), 33.8, 42.2, 43.4, 53.3, 70.1, 70.3, 72.5, 75.2, 80.2, 81.0, 84.6, 92.6, 99.9, 112.7, 128.4, 129.7, 130.5, 134.7, 171.4, 172.2, 175.0, 178.1. HPLC-UV: 98%. HRMS: $C_{28}H_{31}O_{12}$ requires M+H at m/z 559.1816; found, 559.1826.

Example 10

7α-Azido Ginkgolide B (20). Sodium azide (87 mg, 1.34 mmol) and 16 (153 mg, 0.27 mmol) were dissolved in DMSO (2.5 mL) and the solution was heated at 65° C. for 26 h. The solvent was removed in vacuo. The solid was partitioned between saturated aqueous NH$_4$Cl (20 mL) and EtOAc (20 mL) and the aqueous phase was extracted with EtOAc (3×20 mL). The combined organic phases were washed with brine (2×10 mL), dried (MgSO$_4$), and the solvent removed in vacuo. The crude product was purified by flash chromatography eluting with CHCl$_3$/MeOH/EtOAc (30:1:1) to give the 20 as white crystals (109 mg, 88%). A portion (23 mg) of this was recrystallized (MeOH/H$_2$O) for pharmacological evaluation (12 mg). $^1$H NMR (300 MHz, DMSO-d$_6$): δ 1.12 (d, J=7.1, CH$_3$), 1.13 (s, tert-butyl), 1.80 (d, J=4.0, 8-H), 2.73 (q, J=7.1, 14-H), 4.05 (dd, J=7.6, 3.6, 1-H), 4.70 (d, J=7.6, 2-H), 4.74 (d, J=4.0, 7-H), 4.97 (d , J=3.6, 1-OH), 5.06 (d, J=6.0, 10-H), 5.25 (s, 6-H), 6.10 (s, 12-H), 6.52 (s, 3-OH), 7.05 (d, J=6.0, 10-OH). $^{13}$C NMR (100 MHz, DMSO-d$_6$): δ 7.8, 30.1 (3C), 32.7, 41.6, 51.6, 67.2, 68.4, 68.5, 71.0, 73.7, 79.6, 82.9, 92.9, 98.2, 110.3, 169.5, 173.4, 176.2. HPLC-UV: 99%. HRMS: C$_{20}$H$_{24}$O$_{10}$N$_3$ requires M+1 at m/z 466.1462; found, 466.1445.

Example 11

7α-Fluoro Ginkgolide B (21). Tetrabutylammonium fluoride hydrate (37 mg, 0.14 mmol) and 16 (62 mg, 0.11 mmol) were dissolved in CH$_3$CN (1 mL) and heated at 80° C. for 1.5 h. The solvent was removed in vacuo, and the residue was partitioned between 1 N HCl (10 mL) and EtOAc (15 mL) and the aqueous phase was extracted with EtOAc (3×15 mL). The combined organic phases were washed with water (2×15 mL), brine (2×15 mL), dried (MgSO$_4$), and the solvent removed in vacuo. The crude product was purified by flash column chromatography eluting with CHCl$_3$/MeOH/EtOAc (30:1:1) followed by preparative HPLC (eluent B) to give 21 as white crystals (34 mg, 71%). $^1$H NMR (400 MHz, CD$_3$OD): δ 1.25 (s, tert-butyl), 1.26 (d, J=7.1, CH$_3$), 1.94 (dd, $^2J_{HF}$=45.5, J=2.3, 8-H), 3.05 (q, J=7.1, 14-H), 4.24 (d, J=8.0, 1-H), 4.59 (d, J=8.0, 2-H), 5.18 (s, 10-H), 5.35 (d, $^2J_{HF}$=10.9, 6-H), 5.38 (dd, $^1J_{HF}$=48.8, J=2.3, 7-H), 6.14 (s, 12-H). $^{13}$C NMR (75 MHz, CD$_3$OD): δ 7.0, 29.5 (3C), 32.9, 42.4, 53.7 ($^2J_{CF}$=20.4 Hz), 68.8, 69.1, 71.5, 74.5, 79.5 ($^2J_{CF}$=36.0 Hz), 83.7, 91.7, 96.9 ($^1J_{CF}$=184.2 Hz), 98.8, 111.6, 171.2, 173.9, 177.1. HRMS: C$_{20}$H$_{23}$FO$_{10}$ requires M+1 at m/z 443.1354; found, 443.1370.

Example 12

7α-Chloro Ginkgolide B (22). Tetrabutylammonium chloride (86 mg, 0.31 mmol) and 16 (36 mg, 0.06 mmol) were dissolved in CH$_3$CN (1.4 mL) and heated at 80° C. for 12 h. The solvent was removed in vacuo and the residue partitioned between 1 N HCl (20 mL) and EtOAc (20 mL). The aqueous phase was extracted with EtOAc (3×20 mL). The combined organic phases were washed with water (4×10 mL) and brine (2×10 mL), dried (MgSO$_4$), and the solvent removed in vacuo. The crude product was purified by preparative HPLC (eluent B) and recrystallized (CH$_3$CN/CHCl$_3$) to give 22 as white crystals (9 mg, 30%). $^1$H NMR (400 MHz, DMSO-d$_6$): δ 1.12 (d, J=7.0, CH$_3$), 1.17 (s, tert-butyl), 2.19 (d, J=4.2, 8-H), 2.85 (q, J=7.0, 14-H), 4.03 (dd, J=7.7, 3.3, 1-H), 4.63 (d, J=3.3, 1-OH), 4.68 (d, J=7.8, 2-H), 4.84 (d , J=4.2, 7-H), 5.13 (d, J=6.4, 10-H), 5.26 (s, 6-H), 6.17 (s, 12-H), 6.53 (s, 3-OH), 7.57 (d, J=6.4, 10-OH). $^{13}$C NMR (100 MHz, CD$_3$OD): δ 8.7, 31.2 (3C), 34.5, 42.5, 54.2, 65.1, 69.0, 70.0, 72.2, 74.4, 83.7, 84.2, 90.7, 99.4, 111.3, 169.9, 174.4, 177.1. HPLC-UV: 98%. HRMS: C$_{20}$H$_{24}$O$_{10}$Cl requires M+1 at m/z 459.1058; found, 459.1052.

Example 13

Neoginkgolide C (23). Triflate 16 (27 mg, 0.05 mmol) was dissolved in dry MeOH (470 µL) and 2,6-lutidine (150 µL) was added and the reaction mixture was heated at 65° C. for 3 days. The solvent was removed in vacuo and the residue purified by flash chromatography eluting with CHCl$_3$/MeOH/EtOAc (20:1:1) to give the crude product, which was further purified by preparative HPLC (eluent A) to give 23 as white crystals (6 mg, 29%). $^1$H NMR (400 MHz, CD$_3$OD): δ 1.20 (m, CH$_3$ and tert-butyl), 1.64 (dd, J=1.4, 1.2, 8-H), 3.72 (q, J=7.1, 14-H), 4.46 (d, J=8.0, 2-H), 4.59 (d, J=1.2, 10-H), 4.72 (d, J=8.0, 1-H), 5.00 (dd, J=1.4, 1.3, 7-H), 5.14 (d, J=1.3, 6-H), 5.96 (s, 12-H). $^{13}$C NMR (100 MHz, DMSO-d$_6$): δ 7.6, 30.2 (3C), 32.7, 41.3, 47.8, 60.2, 66.9, 67.8, 73.6, 75.6, 82.5, 83.4, 92.7, 93.7, 104.9, 170.2, 171.7, 177.6. HPLC-UV: 98%. HRMS: C$_{20}$H$_{24}$O$_{11}$, requires M+Na at m/z 463.1216; found, 463.1245.

Example 14

10-O-Acetate-7-trifluoromethanesulfonyloxy Ginkgolide B (24). Potassium thioacetate (4 mg, 0.035 mmol) and 16 (3 mg, 0.006 mmol) were dissolved in dry DMF (35 µl) and heated at 40° C. for 3 h. The solvent was removed in vacuo, and the residue was partitioned between water (10 mL) and EtOAc (15 mL) and the aqueous phase was extracted with EtOAc (3×15 mL). The combined organic phases were washed with water (5×10 mL) and brine (2×10 mL), dried (MgSO$_4$), and the solvent removed in vacuo. The crude product was purified by flash chromatography eluting with CHCl$_3$/MeOH/EtOAc (20:1:1) to give 24 (1.3 mg, 18%) as white crystals. $^1$H NMR (400 MHz, DMSO-d$_6$): δ 1.08 (s, tert-butyl), 1.13 (d, J=7.1, CH$_3$), 2.21 (s, COCH$_3$), 2.31 (d, J=12.6, 8-H), 2.85 (q, J=7.1, 14-H), 4.08 (dd, J=5.9, 5.8, 1-H), 4.75 (d, J=5.9, 2-H), 5.09 (dd, J=12.6, 4.2, 7-H), 5.48 (d, J=4.2, 6-H), 6.13 (s, 10-H), 6.33 (s, 12-H), 6.53 (s, 3-OH), 6.71 (d, J=5.8, 1-OH). HRMS: C$_{23}$H$_{26}$O$_{14}$F$_3$S requires M+1 at m/z 615.0995; found, 615.1016.

Example 15

7α-N-Methylamino Ginkgolide B (25). Azide 20 (38 mg, 0.08 mmol) was dissolved in dry MeOH (1.2 ml) and Pd/C (10%, 12 mg) was added. The suspension was stirred under an atmosphere of H$_2$ for 48 h. The solvent was removed in vacuo and EtOAc (10 mL) was added and the solution filtered through Celite. The solvent was removed in vacuo, and the crude product was purified by flash chromatography eluting with CHCl$_3$/MeOH/EtOAc (30:1:1) to give white crystals, which were recrystallized (MeOH) to give 25 (23 mg, 65%) as white crystals. $^1$H NMR (400 MHz, CD$_3$OD): δ 1.22 (m, tert-butyl and CH$_3$), 1.89 (d, J=4.4, 8-H), 2.47 (s, CH$_3$), 3.06 (q, J=7.0, 14-H), 3.46 (d, J=4.4, 7-H), 4.24 (d, J=7.2, 1-H), 4.53 (d, J=7.2, 2-H), 5.05 (s, 6-H), 5.31 (s, 10-H), 6.17 (s, 12-H). $^{13}$C NMR (100 MHz, CD$_3$OD): δ 8.2, 31.3 (3C), 33.4, 34.3, 43.3, 53.5, 69.1, 69.6, 70.8, 72.6, 75.4, 79.3, 84.4, 94.5, 100.6, 112.2, 172.6, 174.8, 178.4. HPLC-UV: 97%. HRMS: C$_{21}$H$_{28}$O$_{10}$N requires M+1 at m/z 454.1713; found, 454.1719.

Example 16

7α-N-Ethylamino Ginkgolide B (26). Azide 20 (48 mg, 0.10 mmol) was dissolved in dry EtOH (1.0 mL) and Pd/C (10%, 15 mg) was added. The suspension was stirred under an atmosphere of H$_2$ for 48 h. The solvent was removed in vacuo and EtOAc (10 mL) was added and the solution filtered through Celite. The solvent was removed in vacuo and the residue purified by flash chromatography eluting with CHCl$_3$/MeOH/EtOAc (30:1:1) to give white crystals, which were recrystallized (MeOH) to give 26 (22 mg, 47%). $^1$H NMR (300 MHz, CD$_3$OD): δ 1.11 (t, J=7.1, CH$_3$), 1.23 (m, tert-butyl and CH$_3$), 1.89 (d, J=4.5, 8-H), 2.57 (dq, J=7.1, 12.0, CH$_2$, 1H), 2.94 (dq, J=7.1, 12.0, CH$_2$, 1H), 3.06 (q, J=7.1, 14-H), 3.56 (d, J=4.5, 7-H), 4.22 (d, J=7.3, 1-H), 4.53 (d, J=7.3, 2-H), 5.08 (s, 6-H), 5.27 (s, 10-H), 6.16 (s, 12-H). $^{13}$C NMR (100 MHz, CD$_3$OD): δ 8.2, 15.5, 31.3 (3C), 34.4, 41.6, 43.3, 53.5, 67.5, 69.2, 70.8, 72.6, 75.3, 80.0, 84.4, 94.4, 100.6, 112.3, 172.6, 174.9, 178.4. HPLC-UV: 98%. HRMS: C$_{22}$H$_{29}$O$_{10}$N requires M+1 at m/z 468.1870; found, 468.1867.

Example 17

7α-Amino Ginkgolide B (27). Azide 20 (10 mg, 0.02 mmol) was dissolved in dry THF (0.4 mL) and Pd/C (10%, 8 mg) was added. The suspension was stirred under an atmosphere of H$_2$ for 14 h. EtOAc (10 mL) was added and the solution filtered through Celite. The solvent was removed in vacuo to give white crystals which were recrystallized (MeOH) to give 27 as white crystals (5 mg, 49%). $^1$H NMR (400 MHz, CD$_3$OD) δ 1.20 (s, tert-butyl), 1.23 (d, J=7.1, CH$_3$), 1.90 (d, J=3.2, 8-H), 3.08 (q, J=7.1, 14-H), 3.83 (d, J=3.2, 7-H), 4.26 (d, J=7.0, 1-H), 4.51 (d, J=7.0, 2-H), 5.01 (s, 6-H), 5.04 (s, 10-H), 6.18 (s, 12-H). $^{13}$C NMR (100 MHz, CD$_3$OD): δ 8.3, 31.0 (3C), 34.1, 43.2, 54.7, 60.3, 68.9, 70.9, 72.6, 74.9, 83.9, 84.4, 95.0, 100.3, 111.8, 172.3, 174.4, 178.4. HPLC-UV: 97%. HRMS: C$_{42}$H$_{26}$O$_{10}$N requires M+H at m/z 440.1557; found, 440.1594.

Example 18

7-Epi-ginkgolide C (18). Acetate 17 (42 mg, 0.087 mmol) was dissolved in a mixture of MeOH and 2 N NaOH (2:1, 1.8 mL) and stirred for 5 h. 1 N HCl was added and the aqueous phase was extracted with EtOAc (3×20 mL). The combined organic phases were washed with brine (2×10 mL), dried (MgSO$_4$), and the solvent removed in vacuo to give 18 (36 mg, 95%) as white crystals. A portion (15 mg) of this was recrystallized (MeOH/H$_2$O) for pharmacological evaluation (6 mg). $^1$H NMR (400 MHz, DMSO-d$_6$): δ 1.12 (d, J=7.0, CH$_3$), 1.12 (s, tert-butyl), 1.64 (d, J=2.7, 8-H), 2.89 (q, J=7.0, 14-H), 4.11 (dd, J=4.5, 6.8, 1-H), 4.37 (dd, J=2.7, 6.3, 7-H), 4.59 (d, J=6.8, 2-H), 4.98 (s, 6-H), 5.04 (d, J=2.7, 10-H), 5.52 (d, J=6.3, 7-OH), 5.64 (d, J=4.5, 1-OH), 6.13 (s, 12-H), 6.45 (s, 3-OH), 6.73 (d, J=2.7, 10-OH). $^{13}$C NMR (75 MHz, DMSO-d$_6$): δ 8.0, 30.2 (3C), 32.6, 41.4, 52.3, 68.8, 69.6, 71.5, 73.4, 76.2, 80.8, 82.8, 92.9, 98.6, 109.7, 170.0, 172.7, 176.3. HPLC-UV: 98%. HRMS: C$_{20}$H$_{25}$O$_{11}$ requires M+1 at m/z 441.1397; found, 441.1395.

Example 19

10-O-Benzyl Ginkgolide B (28). Synthesis and analytical data as previously described (Park, P.-U., et al.; Hu, L., et al., 2000).

Example 20

10-O-Benzyl Ginkgolide C (29). K$_2$CO$_3$ (31 mg, 0.22 mmol) was added to a solution of 2 (12 mg, 0.02 mmol) dissolved in DMF (0.2 mL) followed by addition of benzyl chloride (30 µL, 0.26 mmol). The suspension was stirred for 2.5 h at 60° C. The solvent was removed in vacuo, and the residue partitioned between 1 N HCl (10 mL) and EtOAc (15 mL). The aqueous phase was extracted with EtOAc (3×15 mL). The combined organic phases were washed with water (2×10 mL) and brine NaCl (2×10 mL), dried (MgSO$_4$), and the solvent removed in vacuo. The crude product was purified by flash chromatography eluting with CHCl$_3$/MeOH/EtOAc (20:1:1) and further by preparative HPLC (solvent system A) to give 16 (9 mg, 77%) as white crystals. $^1$H NMR (400 MHz, CD$_3$OD): δ 1.21 (s, tert-butyl), 1.23 (d, J=7.1, CH$_3$), 1.76 (d, J=12.5, 8-H), 3.01 (q, J=7.1, 14-H), 4.13 (dd, J=12.3, 4.3, 7-H), 4.19 (d, J=7.4, 1-H), 4.49 (d, J=7.4, 2-H), 4.76 (d, J=10,2, CH$_2$, 1H), 5.04 (s, 6-H), 5.02 (d, J=4.3, 6-H), 5.25 (s, 10-H), 5.46 (d, J=10.2, CH$_2$, 1H), 6.14 (s, 12-H), 7.37-7.44 (m, aromatic, 5H). $^{13}$C NMR (75 MHz, CDCl$_3$): δ 7.2, 29.1 (3C), 32.2, 41.6, 50.5, 64.1, 67.1, 73.8, 74.3, 75.6, 77.2, 79.3, 83.5, 90.6, 98.5, 110.1, 128.9 (2C), 129.5 (2C), 129.8, 134.2, 170.8, 170.8, 175.5. HPLC-UV: 98%. HRMS: C$_{27}$H$_{30}$O$_{11}$ requires M+Na at m/z 553.1686; found, 553.1684.

Example 21

10-O-Benzyl-7α-fluoro Ginkgolide B (30). Synthesized as described for 29 using K$_2$CO$_3$ (107 mg, 0.77 mmol), 21 (34 mg, 0.08 mmol), and benzyl chloride (89 µL, 0.77 mmol) in DMF (1.8 mL). The crude product was purified by flash chromatography eluting with CHCl$_3$/MeOH/EtOAc (30:1:1) to give 30 (16 mg, 39%) as white crystals. $^1$H NMR (400 MHz, CDCl$_3$): δ 1.25 (s, tert-butyl), 1.30 (d, J=7.0, CH$_3$), 1.88 (dd, $^2J_{HF}$=44.5, J=2.3, 8-H), 2.94 (d, J=3.1, 1-OH), 3.06 (q, J=7.0, 14-H), 4.28 (dd, J=8.1, 3.1, 1-H), 4.50 (d, J=8.1, 2-H), 4.68 (d, J=9.4, CH$_2$, 1H), 4.95 (s, 10-H), 5.29 (d, $^2J_{HF}$=10.2, 6-H), 5.30 (dd, $^1J_{HF}$=50.1, J=1.5, 7-H), 5.41 (d, J=9.4, CH$_2$, 1H), 6.04 (s, 12-H), 7.36 (m, aromatic, 5H). $^{13}$C NMR (100 MHz, CDCl$_3$): δ 7.2, 30.3 (3C), 32.9, 41.7, 53.3 ($^2J_{CF}$=20.4), 68.2, 71.6, 74.1, 74.4, 75.1, 79.5 ($^2J_{CF}$=35.6), 83.6, 90.2, 96.0 ($^1J_{CF}$=184.2), 98.2, 110.9, 128.7(2C), 129.1 (2C), 129.3, 134.8, 170.2, 170.8, 175.1. HPLC-UV: 98%. HRMS: C$_{27}$H$_{30}$O$_{10}$F. requires M+1 at m/z 533.1823; found, 533.1784.

Example 22

10-O-Benzyl-7-epi-ginkgolide C (31). Synthesized as described for 29 using K$_2$CO$_3$ (50 mg, 0.36 mmol), 18 (16 mg, 0.04 mmol), and benzyl chloride (42 µL, 0.36 mmol) in DMF (0.3 mL). The crude product was purified by flash chromatography eluting with CHCl$_3$/MeOH/EtOAc (20:1:1) and further by preparative HPLC (eluent A) to give 31 (11 mg, 56%) as white crystals. $^1$H NMR (400 MHz, CDCl$_3$): δ 1.23 (s, tert-butyl), 1.29 (d, J=7.0, CH$_3$), 1.83 (d, J=3.1, 8-H), 2.49 (d, J=3.6, 1-OH), 2.66 (d, J=11.0, 7-OH), 3.06 (q, J=7.0, 14-H), 3.40 (bs, 3-OH), 4.28 (dd, J=3.6, 7.8, 1-H), 4.48 (m, 2-H, 7-H), 4.72 (d, J=9.2, CH$_2$, 1H), 4.96 (s, 6-H), 5.51 (s, 10-H), 5.50 (d, J=9.2, CH$_2$, 1H), 6.09 (s, 12-H), 7.39-7.44 (m, aromatic, 5H). $^{13}$C NMR (100 MHz, CDCl$_3$): δ 7.3, 30.6 (3C), 33.1, 41.6, 52.9, 68.4, 71.3, 74.0, 74.4, 74.7, 77.6, 82.3, 83.2, 90.7, 98.5, 110.5, 129.2 (2C), 129.6 (2C), 130.1, 133.8, 170.3, 170.5, 175.4. HPLC-UV: 99%. HRMS: C$_{27}$H$_{31}$O$_{11}$, requires M+1 at m/z 531.1866; found, 531.1895.

BIOLOGICAL TESTING—COMPOUNDS 1-15

Radioligand Binding Assay. The radioligand binding assays were performed as previously described (Shindou, 2000). In brief, membrane fractions from hearts and skeletal muscles of PAFR-Tg mice (50 µl suspension containing 121 fmol of PAFR) were mixed with 2 pmol of [$^3$H]-WEB in 50 µl of Buffer [25 mM Hepes/NaOH (pH 7.4), 0.25 M sucrose, 10 mM MgCl$_2$, 0.1% BSA], and the compound to be tested in 100 µl of buffer in a 96-well microplate in triplicate for each concentration. These mixtures were incubated at 25° C. for 90 min, upon which the receptor-bound [$^3$H]—WEB 2086 was filtered and washed with cold Buffer. The plates were then dried at 50° C. for at least 90 min., 25 µl of MicroScint-0 scintillation cocktail was added, and filters were placed in a TopCount microplate scintillation counter. Binding data were analyzed with the nonlinear curve-fitting program Microplate Manager III (Bio-Rad, Hercules, Calif.). Calculated $IC_{50}$ values were then converted to $K_i$ values using the Cheng-Prusoff correction (Cheng, 1973), with the following equation: $K_i=IC_{50}/(1+[L]/K_D)$, where [L] is the concentration of the radioligand, and $K_D$ is the previously determined dissociation constant for $[^3H]$-WEB 2086 (4.3 nM) (Shindou, 2000). Non-specific binding was determined using methods as previously described (Shindou, 2000).

Results

Synthesis. A series of photoactivatable GB (2) and ginkgolide C (GC, 3) derivatives were synthesized. The design of GB derivatives 8a-c and GC derivatives 9a-c (FIG. 3) was based on previous SAR studies of ginkgolides which demonstrated that bulky aromatic substituents in the 10-OH position of GB (2) increases activity at the PAFR (Park, 1996; Hu, 1999; Hu, 2000). Three different photoactivatable moieties, benzophenone, trifluoromethyldiazirine and tetrafluorophenyl azide (see 7a-c, FIG. 3) were chosen as they have been described as being among the most successful for labeling receptors and enzymes (Dorman, 2000; Flemming, 1995; Kotzyba-Hilbert, 1995). Most importantly, upon irradiation these photoactivatable groups react with the receptor via different intermediates, namely, a radical, a carbene or a (singlet) nitrene for the benzophenone (7a), trifluoromethyldiazirine (7b) and tetrafluorophenyl azide (7c) moieties, respectively (Dorman, 2000). Since it is essentially impossible to predict which group will be most readily incorporated into the receptor, use of these different groups increases the likelihood of a successful incorporation.

Figure 3:
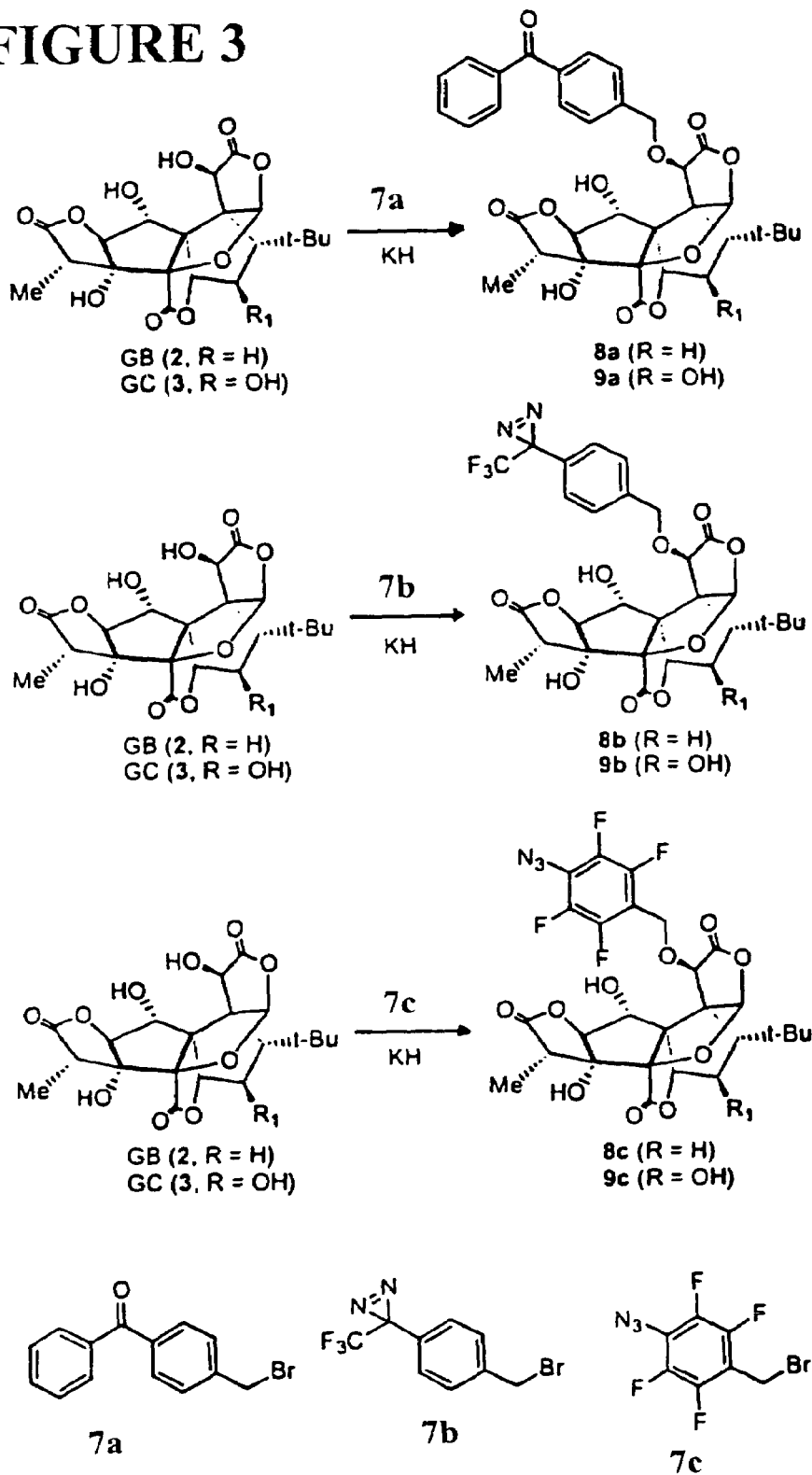
FIG. 3. Derivatives 8a-c and GC derivatives 9a-c.

Preparation of GB derivatives 8a-c and GC derivatives 9a-c was performed by reacting GB (2) and GC (3) with 4-(bromomethyl)benzophenone (7a), 3-(4-bromomethylphenyl)-3-trifluoromethyl-3H-diazirine (7b) and 1-azido-4-(bromomethyl)-2,3,5,6-tetrafluorobenzene (7c), respectively (FIG. 3). Benzophenone 7a was commercially available, whereas trifluoromethyldiazirine 7b (Nassal, 1983; Nassal, 1984) and tetrafluorophenyl azide 7c (Keana, 1990; Lei, 1998; Lei, 2000) (FIG. 5) were synthesized, respectively, in 3 and 7 steps essentially as previously described. Ginkgolides GB (2) and GC (3) were derivatized almost exclusively at 10-OH when potassium hydride (KH) was used as base, as was previously shown for GB (2) (Park, 1996), whereas other bases were less selective, giving rise to products derivatized at 1-OH as well. Generally, the position of the substituent was determined from the coupling systems of the appropriate protons in DMDO-$d_6$, as well as by COSY NMR spectra. The relative chemical shift of 12-H in DMSO-$d_6$ can also be used in differentiating 1- and 10-OH substitutions (Hu, 2000).

Figure 4:
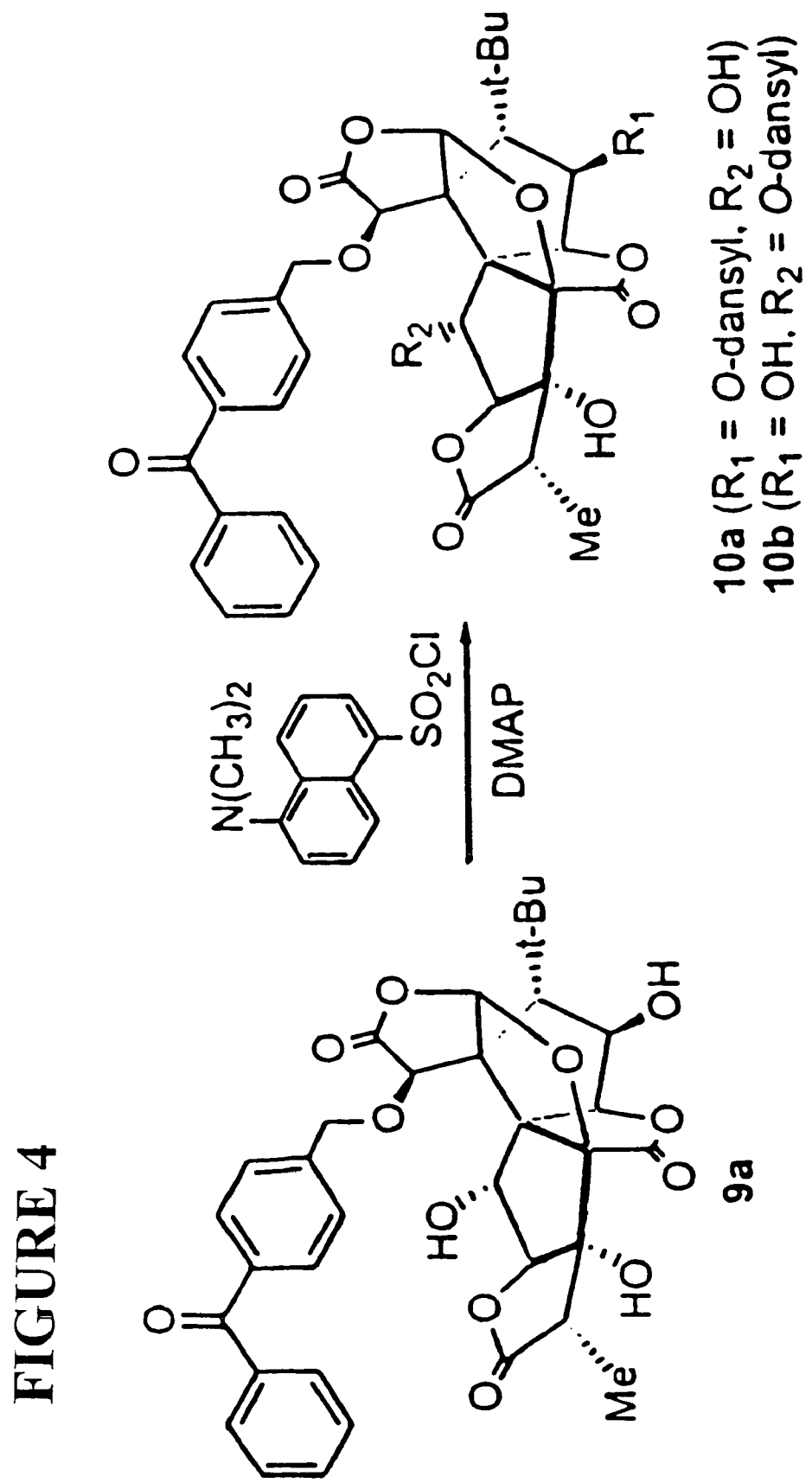
FIG. 4. 10-O-benzophenone-7-O-dansyl GC (10a) and 10-O-benzophenone-1-O-dansyl GC (10b).
Figure 5:
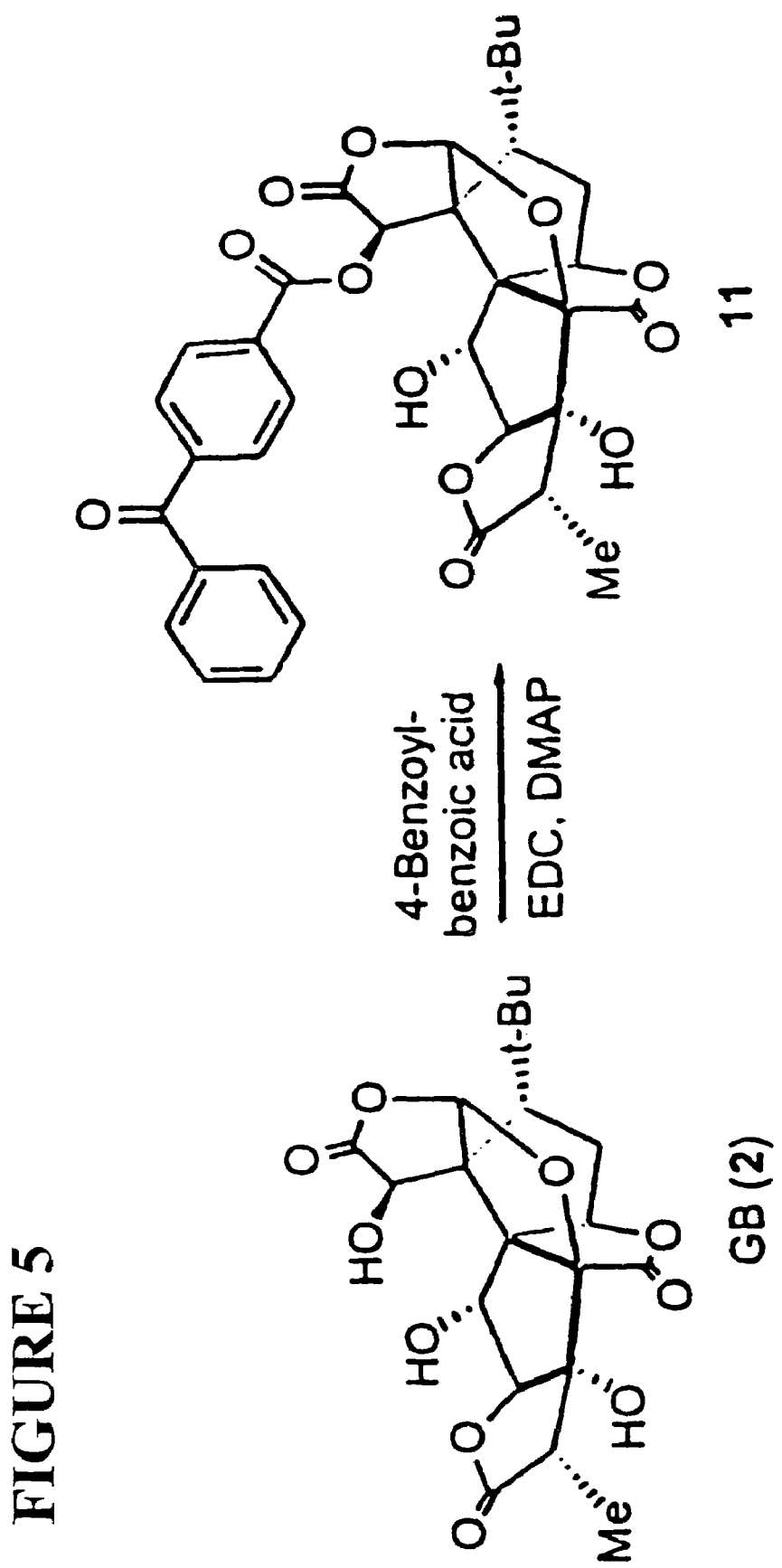
FIG. 5. 10-benzophenonecarbonyl GC (11).

GC derivatives 9a-c can be reacted further to incorporate fluorescent groups; for example, benzophenone derivative 9a was reacted with one equivalent of 5-(dimethylamino) naphthalene-sulfonyl chloride (dansyl chloride), to give 10-O-benzophenone-7-O-dansyl GC (10a) with almost exclusive reaction at 7-OH (FIG. 4). Interestingly, increasing the amount of dansyl chloride to two equivalents gave 10-O-benzophenone-1-O-dansyl GC (10b) as well as (10a) in a 1:1 ratio. The coupling of GB (2) with 4-benzoylbenzoic acid using 1-[3-(dimethylamino)propyl]-3-ethylcarbodiimide HCl (EDC) and 4-dimethylaminopyridine (DMAP) occurred exclusively at 10-OH to give 10-benzophenonecarbonyl GC (11) in good yield (FIG. 5). In 10-benzophenonecarbonyl GC (11) the photoactivatable benzophenone moiety, as in the case of 8a and 9a, is linked to the ginkgolide skeleton through an ester linkage. Upon incorporation into the receptor, the ester group can be aminolysed with a fluorescent amine such as 1-pyrenemethylamine, thus avoiding the use of radioactivity for photolabeling and sequencing (Li, 1999).

Figure 6:
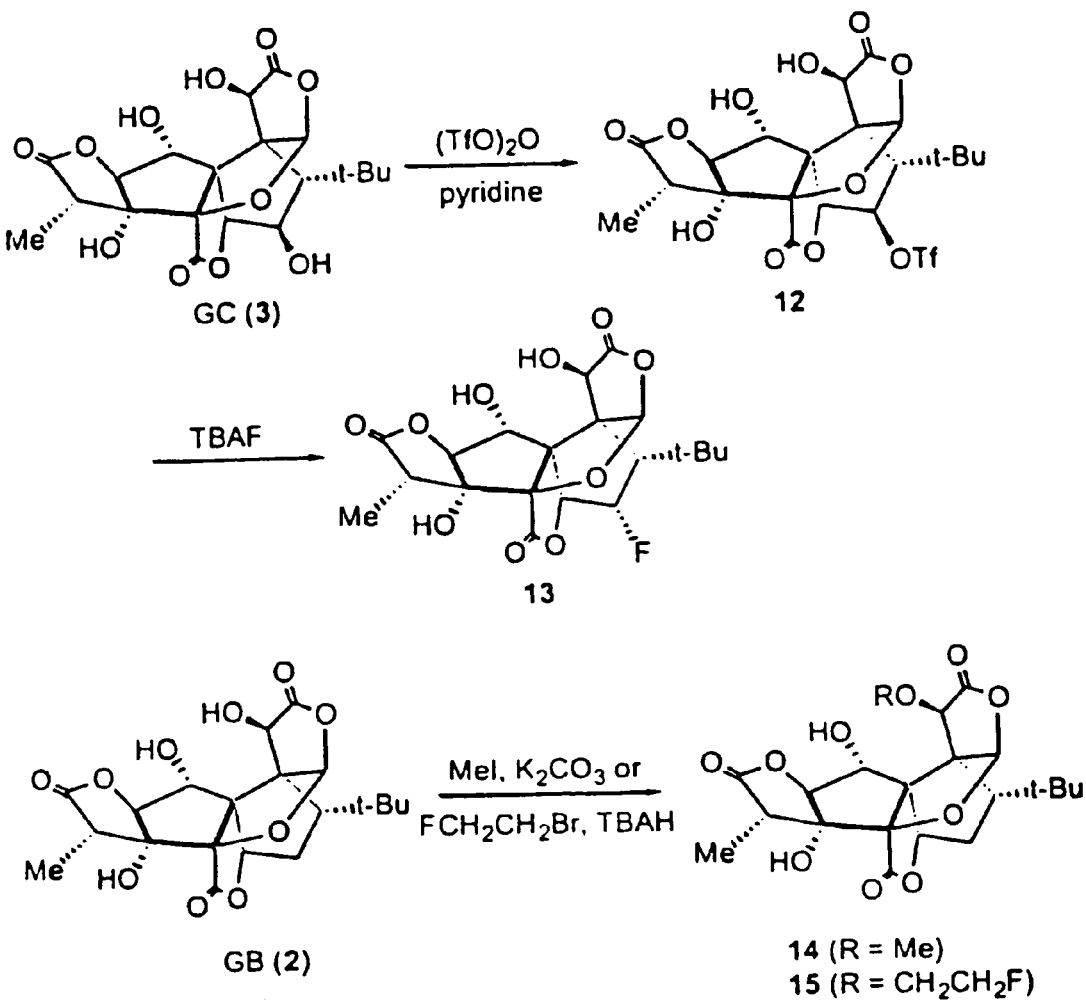
FIG. 6. 7-fluoro analog of GB (13), 10-O-methyl GB (14), and 10-O-(2-fluoroethyl) GB (15).

For positron emission tomography (PET) studies derivatives labeled with $[^{18}F]$- and $[^{11}C]$ possessing half lives of 110 min and 20 min, respectively, will be used. In the present work, preparation of the corresponding non-radioactive analogs has been performed. Compound 13, a 7-fluoro analog of GB (2) which can ultimately be labeled with $[^{18}F]$, was prepared by nucleophilic substitution of 7-O-triflate intermediate 12 with tetrabutylammonium fluoride (TBAF) (FIG. 6). As expected for nucleophilic substitution, NMR showed the relative stereochemistry at C-7 to be reversed compared to GC (3). Intermediate 12 was prepared by reaction of GC (3) with trifluoromethanesulphonic anhydride $[(CF_3SO_2)_2O]$ with remarkable selectivity for the 7-OH, as no substitutions at other hydroxyl groups was observed (Teng, 1997). Two other potential PET-ligands, which can be labeled with $[^{11}C]$, were prepared by selective reaction of the 10-OH of GB (2) with either methyl iodide or 2-bromoethyl fluoride to give 10-O-methyl GB (14) and 10-O-(2-fluoroethyl) GB (15), respectively (FIG. 6). Upon reacting GB (2) with methyl iodide, reaction at 1-OH could not be avoided, the 10-OH:1-OH product ratio being highly sensitive to the use of the appropriate base, e.g., $K_2CO_3$ gave primarily the 10-substituted analog, whereas tetrabutylammonium hydroxide (TBAH) gave mainly the 1-substituted derivative.

Figure 2:
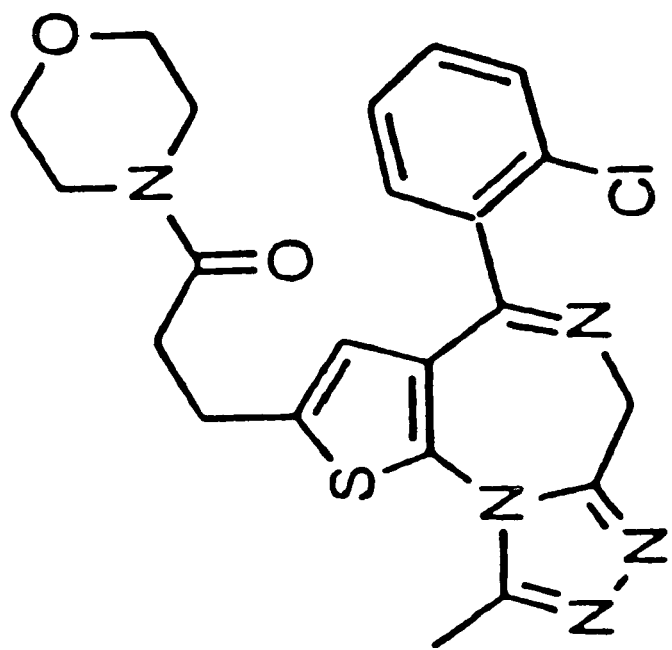
Figure 2:
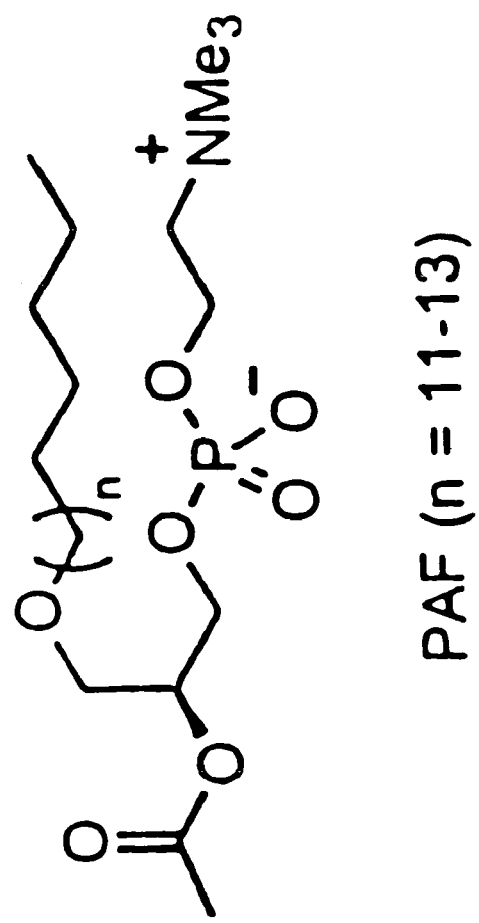

Pharmacology. The native terpene trilactones (1-6), as well as ginkgolide derivatives 8a-c, 9a-c, 10a, 10b, 11 and 13-15 were tested for their ability to bind to PAFR using radioligand binding assays with membrane fractions from hearts and skeletal muscles of PAFR transgenic mice (Shindou, 2000). Initially compounds were tested in concentrations of 5 µM against $[^3H]$-WEB 2086 (FIG. 2), a potent, competitive PAFR antagonist and [3H]-PAF; the compounds were generally less potent against $[^3H]$-PAF, but the relative potencies were comparable with the two radioligands. The degree of non-specific binding was determined to be ca. 50% for [3H]-PAF and less than 5% for $[^3H]$-WEB 2086. Accordingly, the assays were performed using $[^3H]$-WEB 2086 rather than $[^3H]$-PAF as the radioligand, mainly due to the high degree of non-specific binding of the latter.

All compounds were dissolved in DMSO to obtain 5 mM stock solutions of test compounds. Examination of the effect of DMSO on the binding of $[^3H]$-WEB 2086 revealed that up to 1% DMSO (final concentration) was acceptable, but 1-2.5% resulted in a slight inhibition of $[^3H]$-WEB 2086 binding. Generally this caused no problem; however, with very weakly binding compounds the relatively high DMSO concentration in solutions above 100 µM had a small inhibitory effect, thus leading to a slight overestimation of their potencies. Previous studies have reported problems specifically associated with the solubilization of ginkgolides in DMSO (Maclennan, 1996), but similar problems were not observed in the present study.

Native ginkgolides (1-5) and bilobalide (6) were tested with the cloned PAFR (FIG. 3A and Table 1). GB (2) was the most potent compound with a $K_i$ value of 0.56 µM, while GA (1) was slightly less potent with a $K_i$ of 1.46 µM. GC (3) and ginkgolide J (GJ, 4) were significantly less potent, while ginkgolide M (GM, 5) and bilobalide (6) both had $K_i$ values larger than 50 µM. The GB-derived photoactivatable compounds 8a-c and 11 with $K_i$ values in the range 0.09-0.15 µM (FIG. 3B and Table 2) were all more potent than GB (2), while compounds 9a-c derived from GC (3) with $K_i$ values of 0.47-0.79 μM were equipotent to GB (2) (FIG. 3C and Table 2), despite the fact that GC (3) itself is only weakly potent. Besides proving that aromatic groups linked to 10-OH enhance activity in both GB (2) and GC (3) derivatives, these results also indicate that the specific type of photoactivatable group was less important. Derivatives 10a and 10b possessing a fluorescent dansyl group at either 1- or 7-OH were both less potent than 10-O-benzophenone GC (9a) without the dansyl group (FIG. 3D). However, an important difference was observed in the activities of the two; the 1- and 10-disubstituted analog (10b) was ca. four times more potent than the 7- and 10-disubstituted analog (10a) (Table 2).

TABLE 1

The $K_i$ values of the native terpene trilactones.

| Compound | $K_i$ (μM)[a] |
|---|---|
| GA (1) | 1.46 |
| GB (2) | 0.56 |
| GC (3) | 12.6 |
| GJ (4) | 9.90 |
| GM (5) | >50 |
| BB (6) | >50 |

[a]Inhibition of [$^3$H]-WEB 2086 binding.

TABLE 2

The $K_i$ values of the synthesized derivatives.

| Compound | $K_i$ (μM)[a] |
|---|---|
| 8a | 0.15 |
| 8b | 0.15 |
| 8c | 0.09 |
| 9a | 0.58 |
| 9b | 0.47 |
| 9c | 0.79 |
| 10a | 3.94 |
| 10b | 0.96 |
| 11 | 0.13 |
| 13 | 0.99 |
| 14 | 3.16 |
| 15 | 4.87 |

[a]Inhibition of [$^3$H]-WEB 2086 binding.

Finally the potential PET analogs 13-15 were tested. The fluorinated analog 13 had a $K_i$ value of 0.99 μM (Table 2), thus being almost equipotent with the native compound GB (2). The C-10 derivatized compounds 10-O-methyl GB (14) and 10-O-(2-fluoroethyl) GB (15) were both significantly less potent than GB (2) with $K_i$ values of 3.16 and 4.87 μM for 14 and 15, respectively (Table 2).

Discussion

Nine analogs (8a-c, 9a-c, 10a, 10b and 11) with photoactivatable groups, and in the case of 10a and 10b with fluorescent dansyl groups as well, have been prepared from native ginkgolides GB (2) and GC (3) by selective derivatizations of the hydroxyl groups. Furthermore, we have prepared three analogs (13-15), the radioactive versions of which will be used for PET studies. For the synthesis of 7-O-triflate intermediate 12, reaction of GC (3) with sulfonic anhydride gave rise to remarkable selectivity at 7-OH (Teng, 1997). 10-O-Methyl GB (14) and 10-O-(2-fluoroethyl) GB (15) were synthesized by derivatization of GB (2), indicating that when the appropriate combination of alkylating agent and base is used, even small aliphatic groups react preferentially at the 10-OH. Generally, the increased reactivity of the 1-OH and 10-OH compared to 7-OH, has been rationalized by hydrogen-bonding between 1-OH and 10-OH (Corey, 1992), but this does not explain the interesting selectivity for the 10-OH position in reactions with benzyl bromide derivatives. Notably, reaction of GC (3) with a bulky silyl chloride protection group occurs exclusively at the 1-OH of GC (Weinges, 1991).

All native terpene trilactones as well as the derivatized compounds were investigated with respect to their binding to cloned PAFR isolated from transgenic mice (FIG. 3A). Previous SAR studies of PAFR antagonism with terpene trilactones and derivatives was performed by monitoring inhibition of PAF-induced rabbit platelet aggregation. GB (2) has generally been reported to be a potent antagonist of the PAFR based on the latter assay with an $IC_{50}$, value around 0.2 μM (Park, 1996; Hu, 1999; Hu, 2000).

GM (5) has only been found in the root bark of the *G. biloba* tree (Nakanishi, 1967) and is not readily available. Thus, the interaction between PAFR and GM (5) has not previously been reported. The remaining terpene trilactones are all found in the leaf of *G. biloba*. However 5, lacking the hydroxyl group at C-3, was devoid of PAFR binding at the concentrations tested. Generally the activities of GC (3), GJ (4) and GM (5) with hydroxyl groups at C-7, compared to the activity of GA (1) and GB (2) lacking the 7-OH, showing that the 7-OH is not necessary for binding to PAFR, whereas hydroxyl groups at other positions appear to be less important. The study also confirmed that bilobalide (6), a terpene trilactone with only one five-membered carbocycle and three lactones, is not active in concentrations up to 100 μM (Table 1).

The seven photolabile analogs, GB derivatives 8a-c and 11 and GC derivatives 9a-c, with aromatic substituents at 10-OH all improved the affinity to the PAFR relative to the activities of GB (2) and GC (3) (Table 2). This is in agreement with previous SAR studies of GB (2) (Park, 1996; Hu, 1999; Hu, 2000), as well as a 3D-QSAR study on ginkgolides (Chen, 1998). However, it is interesting to note that aromatic substitutions at 10-OH of GC (3) as in compounds 9a-c, improve the affinity to PAFR ca. 20 fold (FIG. 3C) thus making them equipotent to GB (2), while the same substitutions in GB (2) increases the affinity only 6-fold (FIG. 3B). Furthermore, the similar affinities of GB derivatives 8a-c (FIG. 3B) and 11 and GC derivatives 9a-c (FIG. 3C), respectively, implies that it is the steric bulk or the lipophilicity of the substituents, rather than the specific functional groups that are important for the increase in affinity (Table 2).

GC derivatives 10a and 10b (FIG. 4) with dansyl groups at 7-OH and 1-OH are less potent and equipotent, respectively to their parent compound, 10-O-benzophenone-GC (9a) (FIG. 3D). In compound 10a, which is ca. 6 times less active than 9a (Table 2), the bulk at the 7 position seems to be responsible for the reduction in affinity. The fact that compound 10b is equipotent to 9a suggests that once a bulky aromatic group occupies this area, further aromatic groups neither increase nor decrease the affinity.

The 7-fluoro GB (13, FIG. 6) was essentially equipotent to GB (2), and ca. 10 times more potent than GC (3); thus, the [$^{18}$F]-labeled analog of 13 could be a useful probe for visualizing the PAFR binding sites in mammalian brain. Furthermore, 13 could be used for probing interactions of [$^{18}$F]-13 with targets other than the PAFR. The substitution at C-7 of ginkgolides is critical for PAFR binding affinity; generally a β-OH group significantly decreases binding affinity, as in GC (3), GJ (4) and GM (5), while substitution with a dansyl group at 7-OH, as in 10a, reduces this activity further. However, an α-fluorine at C-7 position has an affinity 10-fold higher than that of GC (3) and comparable to that of GB (2). The inverted stereochemistry at C-7, rather than electronic or steric effects of the fluorine substitution, may account for the enhanced activity.

Others who have made, or purported to make, Ginkgolide derivatives with modifications at C-7 did not appreciate the importance of stereochemistry at the C-7 position (Pietry, WO 99/52911; Ceazaux, GB 2,288,599; Vasella, U.S. Pat. No. 6,143,725). The data presented shows the unexpected improvement in PAFR binding affinity when the C-7 substituent is an α-substituent. Thus, Ginkgolide derivatives having both an α-substituent at C-7 and a bulky or lipophillic substitution at 10-OH are expected to have yet further improved activity.

The two derivatives bearing alkyl substituents at C-10 of GB, 10-O-methyl GB (14) and 10-O-(2-fluoroethyl) GB (15), are both significantly less potent than GB (2). Thus, although the [$^{11}$C]-labeled derivatives are not suited for examination of interactions with the PAFR, both ligands should be useful for visualizing targets for ginkgolides in the brain, other than PAFR. Of course, all of the described compounds are expected to be useful for visualizing their targets in the brain, other than PAFR.

In conclusion, investigation of the effect of terpene trilactones isolated from G. biloba on the cloned PAFR have demonstrated that amongst the native compounds, GA (1) and GB (2) are the most potent. A series of photoactivatable analogs have been prepared, and PAFR binding assays showed that most of these analogs were more potent antagonists than their parent compounds, thus providing promising candidates for studies of the interaction of ginkgolides with the PAFR. The gingkolide derivative containing both a photoactivatable and a fluorescent group, compound 10b, retained affinity to PAFR, and could therefore be useful in photolabeling and subsequent sequencing studies. Finally, the syntheses and assays of analogs that can be radiolabeled and used for PET studies have been described; in particular the radiolabeled derivative of 7-fluoro GB (13) could be a useful probe for in vivo PET studies of the PAFR, as well as potential new targets for ginkgolides.

BIOLOGICAL TESTING—COMPOUNDS 16-31

Radioligand Binding Assay. The radioligand binding assays were performed as previously described (Shindou, 2000). In brief, membrane fractions from hearts and skeletal muscles of PAFR-Transgenic mice (50 µL suspension containing 158 fmol of PAFR) were mixed with 2 pmol of [$^3$H]-WEB 2086 in 50 µL of Buffer [25 mM Hepes/NaOH (pH 7.4), 0.25 M sucrose, 10 mM MgCl$_2$, 0.1% BSA], and the compound to be tested in 100 µL of buffer in a 96-well microplate in triplicate for each concentration. These mixtures were incubated at 25° C. for 90 min, upon which the receptor-bound [$^3$H]-WEB 2086 was filtered and washed with cold buffer. The filters were then dried at 50° C. for at least 90 min., 25 µL of MicroScint-0 scintillation cocktail was added, and filters were placed in a TopCount microplate scintillation counter. Binding data were analyzed with the nonlinear curve-fitting program Microplate Manager III (Bio-Rad, Hercules, Calif.). Non-specific binding was determined using methods as previously described (Shindou, 2000).

Results

Pharmacology. Derivatives 17-23 and 25-31 were tested for their ability to displace [$^3$H]-WEB 2086 binding to cloned PAFR (Tables 2 and 3) using membrane fractions from hearts and skeletal muscles of PAFR transgenic mice, as previously described (Shindou, 2000). In these fractions, GB (1) had a $K_i$ value of 0.88 µM, thus being similar to the previously determined $K_i$ value of 0.56 µM (Strømgaard, 2002)

TABLE 4

The $K_i$ values of ginkgolide B (1) and C (2), and 7-epi derivatives

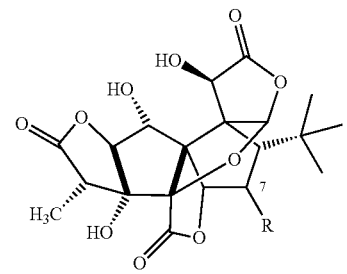

| Compound | R | $K_i$ (µM)[a] |
|---|---|---|
| GB (1) | H | 0.88 |
| GC (2) | β-OH | 12.6[b] |
| 7α-OAc-GB (17) | α-OAc | 7.84 |
| 7-epi-GC (18) | α-OH | 4.26 |
| 7α-OCOCH$_2$Ph-GB (19) | α-OCOCH$_2$Ph | 2.40 |
| 7α-N$_3$-GB (20) | α-N$_3$ | 0.55 |
| 7α-F-GB (21) | α-F | 0.99 |
| 7α-Cl-GB (22) | α-Cl | 0.11 |
| 7α-NHMe-GB (25) | α-NHMe | 0.61 |
| 7α-NHEt-GB (26) | α-NHEt | 1.62 |
| 7α-NH$_2$-GB (27) | α-NH$_2$ | 8.64 |

[a]Inhibition of [$^3$H]-WEB 2086 binding. Values are means of two independent experiments performed in triplicate.
[b]Data from previous studies (Strømgaard, K., et al.).

Derivatives with 7α-substituents were all more potent than GC (2) (Table 4), but within this group of compounds there were marked differences; 7α-OAc, 7α-OCOBn, 7α-OH and 7α-NH$_2$ ginkgolide B derivatives all had $K_i$ values between 2.4-7.8 µM, thus being slightly more potent than GC (2), but still significantly less potent than GB (1). Compounds 20, 21, 25 and 26 with 7α-N$_3$, 7α-F, 7α-NHMe and 7α-NHEt substituents, respectively, were equipotent to GB (1) with $K_i$ values in the range of 0.55-1.62 µM. Finally, 7α-chloro ginkgolide B (22) was the most potent compound in this series with a $K_i$ value of 0.11 µM, thus being the most potent non-aromatic ginkgolide derivative described.

TABLE 5

The $K_i$ values of benzylated derivatives.

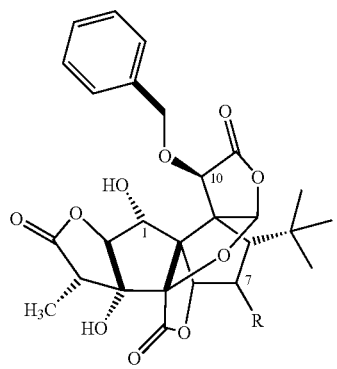

| Compound | R | $K_i$ (µM)[a] |
|---|---|---|
| 10-OBn-GB (28) | H | 0.12 |
| 10-OBn-GC (29) | β-OH | 1.67 |

TABLE 5-continued

| 10-OBn-7α-F-GB (30) | α-F | 0.10 |
| 10-OBn-epi-GC (31) | α-OH | 0.60 |

[a]Inhibition of [$^3$H]-WEB 2086 binding. Values are means of two independent experiments performed in triplicate.

The relactonized compound 23 (Scheme 2) was also tested for binding to PAFR and was found to be essentially inactive with a $K_i$ value>40 µM. Benzyl derivatives were investigated as well (Table 3), and as expected a 10-O-benzyl group significantly improved the affinity for PAFR. Compounds 28 and 30 were the most potent with $K_i$ values of 0.12 and 0.10 µM, respectively, while 10-O-benzyl-GC (29) and 10-O-benzyl-7-epi-GC (31) were slightly less potent with $K_i$ values of 1.67 and 0.60 µM, respectively.

Discussion

Figure 8:
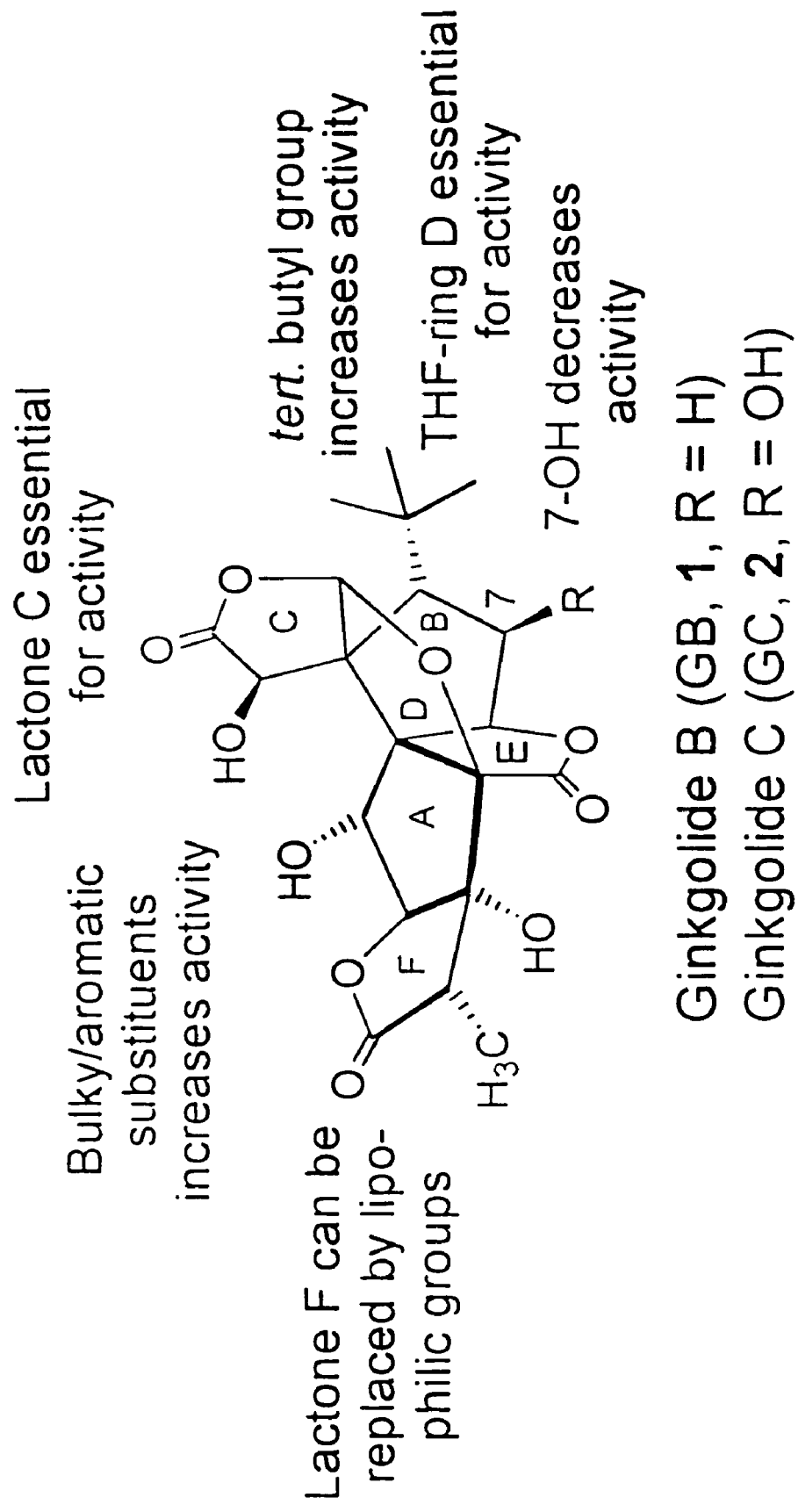
FIG. 8. Summary of structure-activity relationship (SAR) studies of ginkgolides as PAFR antagonists. GB (1) is ca. 25-fold more potent than GC (2).

Structure-activity relationship (SAR) studies of ginkgolides on the PAFR have primarily focused on GB (1) (FIG. 8) derivatives (Corey, 1989; Corey, 1991; Park, U.S. Pat. No. 5,541,183; Hu, 1999; Hu, 2000) as outlined in FIG. 8, e.g. the importance of lactones and the tert-butyl group has been investigated, whereas the effect of stereochemistry of hydroxyl groups remains to be examined. Ginkgolide C (GC, 2, FIG. 8), having a hydroxyl group at C-7, is significantly less potent than GB (1) (Strømgaard, 2002), which has been explained by the hydrophilic 7α-OH of GC (2) being next to the lipophilic tert-butyl group, which is believed to interact with a lipophilic pocket in the PAFR (Braquet, 1991). Moreover, substitution at 7-OH further decreases antagonistic activity, as demonstrated by 7-O-(4-methylphenyl)-GB that was devoid of PAFR activity (Pietri, 2001), and a 7-O-dansyl-GB derivative was also less potent than the parent compound (Strømgaard, 2002).

Preliminary studies showed that 7α-F-GB was equipotent to GB, and 15-fold more potent as a PAFR antagonist as compared to GC (2) (Suehiro, M., et al.), despite the fact that fluorine is sterically equivalent to OH, and more polar than hydrogen (Smart, 2001). Since configuration of the fluorine atom is α, whereas that of the 7-hydroxyl in GC (2) is β, it is not clear whether this difference in activity is due to changes in stereochemistry, steric effects or electronic effects. In the following, we describe a series of ginkgolide derivatives with variation at the critical 7-position, and the assessment of these derivatives for their ability to displace radioligand binding to cloned PAFR.

Herein the effect of modification of the C-7 position of ginkgolides has been investigated by synthesis of fifteen analogs (17-31), which have been prepared from native ginkgolides GB (1) and GC (2), and evaluated with the cloned PAFR.

The derivatives with 7α-substituents were prepared by nucleophilic substitution of 7β-OTf-GB (16), but in several cases these reactions did not proceed as expected. Attempts to introduce larger halogens such as bromine and iodine, as well as other nucleophiles failed. In the reaction between 16 and NaSCOCH$_3$, the 7-OTf group remained intact; instead the reaction presumably took place at C-11 of lactone C to give 24 (Scheme 2). Reaction of 16 with MeOH and 2,6-lutidine gave rise to neoginkgolide C (23) with a novel rearranged skeleton (Scheme 2). This compound had a $K_i$ value>40 µM, which is in agreement with previous studies which showed that modification of lactone C significantly reduced PAFR binding (FIG. 8) (Hu, 2001).

During the reduction of azide 20 interesting observations were made; when carried out in MeOH this reaction did not give the expected primary amine 27, but gave N-methylamine 25 instead, and when carried out in EtOH the reduction gave N-ethylamine 26. Besides being a potential novel procedure for a direct conversion of azides into alkylated amines, it also raises mechanistic considerations. Treatment of 27 with Pd/C in MeOH gave 25, albeit in lower yield than starting from azide 20, and with several side products. This implies that in the preparation of 25 and 26 the azide 20 is initially reduced to amine 27, which then reacts instantly with the oxidized solvent to form an imine, that is reduced to yield the products. Further studies should confirm this pathway, as well as the generality of this reaction.

The prepared derivatives were tested for binding to cloned PAFR (Tables 4 and 5). It was observed that 7α-derivatives were slightly more potent than the 7β-derivatives, as GC (2) had a $K_i$ value of 12.6 µM, while for 7-epi-GC (18) $K_i$ is 4.26 µM. Likewise 7α-OAc-GB (17) had a $K_i$ of 7.84 µM, while 7β-OAc-GB (i.e., 7-OAc-GC) had been shown to have low potency comparable to that of GC (2) (Jaracz, 2002). Furthermore, the 7β-derivative 19 is a reasonably potent PAFR antagonist with a $K_i$ value of 2.40 µM (Table 4) in contrast to 7β-O-(4-methylphenyl)-GB, which is devoid of PAFR activity (Pietri, 2001).

The nature of the 7α-substituent, on the other hand, had a major impact on the binding to PAFR. It appears that polarizable substituents at C-7 lead to increased potency. Introduction of azide and fluorine groups yielded compounds that were equipotent to GB (1) (Table 4), while introduction of a chlorine as in 7α-Cl-GB (22) leads to a dramatic increase in binding affinity. Thus 22 with $K_i$=0.11 µM, was 115-fold more potent than GC (2), and 8-times more potent than GB (1), thereby being the most potent non-aromatic ginkgolide derivative described to date. On the other hand, it appears that polar groups that can form hydrogen bonds decrease activity, as seen in the case of a hydroxyl group at C-7 to give 7-epi-GC (18) and an amino group to give 7α-NH$_2$-GB (27), compounds with binding affinities lower than GB. However, alkylation of 27 to give 7α-NHMe-GB (25) and 7α-NHEt-GB (26) led to significant increases in binding affinities, with $K_i$ values of 0.61 µM and 1.62 µM, respectively. It may be that such alkylations of the 7α-amino group sterically disfavors hydrogen bonding. Nevertheless, rationalization of these trends requires further developments in ongoing molecular mechanistic studies of the ginkgolide/PAFR interaction.

Introduction of benzyl groups in the 10-OH position of ginkgolides is known to improve affinity for PAFR (Park, P.-U., et al., U.S. Pat. No. 5,541,183; Hu, 2000; Strømgaard, 2002), but whether this is true for 7α-substituted derivatives was not known. The affinities of 10-O-benzyl-7α-F-GB (30) and 10-O-benzyl-7-epi-GC (31) (Table 5) shows 10- and 7-fold improved affinity compared to their non-benzylated derivatives. Thus 10-benzylation of 7α-substituted derivatives improves binding affinity as previously shown for other ginkgolide derivatives.

In conclusion we have synthesized several ginkgolide derivatives with modifications at C-7. These syntheses have led to several unexpected products such as 23 and 24, as well as a potential novel procedure for a direct conversion of azides into alkylamines. Moreover, contrary to previous convictions, we have shown that introducing lipophilic groups in the C-7 position, in particular chlorine, significantly improves PAFR affinity compared to GB (1). This gives rise to new possibilities for improving affinity of ginkgolides to PAFR, as well as providing material for future SAR studies of ginkgolides and PAFR.

REFERENCES

Aoki, Y., Nakamura, M., Kodama, H., Matsumoto, T., Shimizu, T. & Noma, M. (1995) *J. Immunol. Methods*, 186, 225-231.

van Beek, T. A.; Lelyved, G. P. Preparative isolation and separation procedure for ginkgolides A, B, C, and J and bilobalide. *J. Nat. Prod.* 1997, 60, 735-738.

Bito, H., Nakamura, M., Honda, Z., Izumi, T., Iwatsubo, T., Seyama, Y., Ogura, A., Kudo, Y., & Shimizu, T. (1992) *Neuron* 9, 285-294.

Bradford, M. M. (1976) *Anal. Biochem.* 72, 248-254.

Braquet, P., Spinnewyn, B., Braquet, M., Bourgain, R. H., Taylor, J. E., Etienne, A., & Drieu, K. (1985) *Blood Vessels* 16, 559-572.

Braquet, P. The ginkgolides: potent platelet-activating factor antagonists isolated from *Ginkgo biloba* L.: chemistry, pharmacology and clinical applications. *Drugs. Future* 1987, 12, 643-699.

Braquet, P. Esanu, A.; Buisine, E.; Hosford, D.; Broquet, C.; Koltai, M. Recent progress in ginkgolide research. *Med. Chem. Rev.* 1991, 11, 295-355.

Ceazaux et al., UK Patent Application GB 2 288 599 A.

Chen, J., Hu, L., Jiang, H., Gu, J., Zhu, W., Chen, Z., Chen., K., & Ji, R. (1998) *Bioorg. Med. Chem. Lett.* 8, 1291-1296.

Chen, C., Magee, J. C., Marcheselli, V., Hardy, M., & Bazan, N. G. (2001) *J. Neurophysiol.* 85, 384-390.

Cheng, Y. & Prusoff, W. H. (1973) *Biochem. Pharmacol.* 22, 3099-3103.

Chung, S.-K.; Ban, S. H.; Woo, S. H. Heterocyclic lipids with PAF antagonist activities 3. Synthesis of 2,4-bis(hydroxymethyl)-oxetane and 1,3-bis(hydroxymethyl)-cyclobutane derivatives. *Korean J. Med. Chem.* 1995, 5, 84-93.

Corey, E. J. & Ghosh, A. K. (1988) *Tetrahedron Lett.* 29, 3205-3206.

Corey, E. J., Kang, M. C., Desai, M. C., Ghosh, A. K., & Houpis, I. N. (1988) *J. Am. Chem. Soc.* 110, 649-651.

Corey, E. J. & Su, W. G. (1987) *J. Am. Chem. Soc.* 109, 7534-7536.

Corey, E. J. & Gavai, A. V. (1989) *Tetrahedron Lett.* 30, 6959-6962.

Corey, E. J. & Rao, K. S. (1991) *Tetrahedron Lett.* 32, 4623-4626.

Corey, E. J.; Rao, K. S. & Ghosh, A. K. (1992) *Tetrahedron Lett.* 33, 6955-6958.

Cruzado, J. M.; Torras, J.; Riera, M.; Borobia, F.; Condom, E.; Matorell, J.; Herrero, I.; Lloberas, N.; Seron, D.; Gil-Vernet, S.; Alsina, J.; Grinyo, J. M. A Platelet Activating Factor Receptor Antagonist (BN52021) prevents hyperacute rejection in a pig kidney-human blood xenoperfusion model. *ASTP Meeting Abstracts* 1997.

DeFeudis, F. V. *Ginkgo biloba* extract (EGb 761). From chemistry to clinic. Ullstein Medical, Wiesbaden, 1998, pp. 401.

DeFeudis, F. V. & Drieu, K. (2000) *Curr. Drug Targets*, 1, 25-58.

Diamond, B. J., Shiflett, S.C., Feiwel, N., Mathies, R. J., Noskin, O., Richards, J. A., & Schoenberger, N. E. (2000) *Arch. Phys. Med. Rehabil.* 81, 668-678.

van Dongen, M. C. J. M., van Rossum, E., & Knipschild P. (2000) in *Medicinal and Aromatic Plants-Industrial Profiles: Ginkgo biloba*, ed. van Beek, T. A. (Harwood Academic Publishers, Amsterdam), Vol. 12, pp. 385-442.

Dorman, G. & Prestwich, G. D. (2000) *Trends Biotech.* 18, 64-77.

Drieu, K., Jaggy, H. (2000) in *Medicinal and Aromatic Plants-Industrial Profiles: Ginkgo biloba*, ed. van Beek, T. A. (Harwood Academic Publishers, Amsterdam), Vol. 12, pp. 267-277.

Ebara, T.; Miura, K.; Matsuura, T.; Imanishi, M.; Yamano, Y.; Kim, S.; Iwao, H. Role of Platelet Activating Factor and prostanoids in hemodynamic changes in rat experimental end toxic shock. *Jpn. J. Pharmacol.* 1996, 71, 247-253.

Flemming, S. A. (1995) *Tetrahedron* 51, 12479-12520.

Fukunaga, K., Ishii, S., Asano, K., Yokomizo, T., Shiomi, T., Shimizu, T. & Yamaguchi, K. (2001) *J. Biol. Chem.*, 276, 43025-43030.

Grino, J. M. BN52021: A Platelet Activating Factor Antagonist for preventing post-transplant renal failure. *Annals Int. Med.* 1994, 121, 345-347.

Hasler, A. (2000) in *Medicinal and Aromatic Plants-Industrial Profiles: Ginkgo biloba*, ed. van Beek, T. A. (Harwood Academic Publishers, Amsterdam), Vol. 12, pp. 109-142.

Hu, L., Chen, Z., Cheng, X., & Xie, Y. (1999) *Pure Appl. Chem.* 71, 1153-1156.

Hu, L., Chen, Z., Xie, Y., Jiang, H., & Zhen, H. (2000) *Bioorg. Med. Chem.* 8, 1515-1521.

Hu, L., Chen, Z., Xie, Y., Jiang, Y., & Zhen, H. (2000) *J. Asian Nat. Prod. Res.* 2, 103-110.

Hu, L., Chen, Z., & Xie, Y. (2001) *J. Asian Nat. Prod. Res.* 3, 219-227.

Ishii, S., Nagase, T., Tashiro, F., Ikuta, K., Sato, S., Waga, I., Kume, K., Miyazaki, J., & Shimizu, T. (1997) *EMBO J.* 16, 133-142.

Ishii, S. & Shimizu, T. (2000) *Prog. Lipid. Res.* 39, 41-82.

Jaracz, S.; Strømgaard, K.; Nakanishi, K. Ginkgolides: selective acetylations, translactonization and biological evaluation. *J. Org. Chem.* 2002, 67, 4623-4626.

Kanowski, S., Hermann, W. M., Stephan, K., Wierich, W., & Horr, R. (1996). *Pharmacopsychiatry* 29, 47-56.

Kato, K., Clark, G. D., Bazan, N. G., & Zorumski, C. F. (1994) *Nature* 367, 175-179.

Keana, J. F. W. & Cai, S. X. (1990) *J. Org. Chem.* 55, 3640-3647.

Kennedy, D. O., Scholey, A. B., & Wesnes, K. A. (2000) *Psychopharmacol.* 151, 416-423.

Kleijnen, J. & Knipschild, P. (1992) *Lancet* 340, 1136-1139.

Kobayashi, K., Ishii, S., Kume, K., Takahashi, T., Shimizu, T., & Manabe, T. (1999) *Eur. J. Neurosci.* 11, 1313-1316.

Kornecki, E., Wieraszko, A., Chan, J. C., & Ehrlich, Y. H. (1996) *J. Lipid Mediators Cell Signal.* 14, 115-126.

Kotzÿba-Hilbert, F., Kapfer, I., & Goeldner, M. (1995) *Angew. Chem. Int. Ed. Engl.* 34, 1296-1312.

Krieglstein, J. Neuroprotective properties of *Ginkgo biloba*-constituents. *Zeitschrift Phytother* 1994, 15, 92-96.

Kroegel, C., Kortsik, C., Kroegel, N. & Matthys, H. (1992) *Drugs Aging* 2, 345-355.

Le Bars, P. L., Katz, M. M., Berman, N., Itil, T. M., Freedman, A. M., & Schatzberg, A. F. (1997) *J. Am. Med. Assoc.* 278, 1327-1332.

Lei, H., Marks, V., Pasquale, T., & Atkinson, J. K. (1998) *Bioorg. Med. Chem. Lett.* 8, 3453-3458.

Lei, H. & Atkinson, J. (2000) *J. Org. Chem.* 65, 2560-2567.

Li, H., Liu, Y., Fang, K., & Nakanishi, K. (1999) *Chem. Commun.* 365-366.

Lichtblau, D.; Berger, J. M.; Nakanishi, K. An efficient extraction of ginkgolides and bilobalide from *Ginkgo biloba* leaves. *J. Nat. Prod.* 2002, 65, 1501-1504.

Lindsberg, P. J.; Yue, T.-L.; Frerichs, K. U.; Hallenbeck, J. M., Feuerstein, G. Evidence for Platelet-Activating Factor as a Novel Mediator in Stroke in Rabbits. *Stroke* 1990, 21, 1452-1457.

Logani, S., Chen, M. C., Tran, T., Le, T., & Raffa, R. B. (2000) *Life Sci.* 67, 1389-1396.

Maclennan, K. M., Smith, P. F., & Darlington, C. L. (1996) *Neurosci. Res.* 26, 395-399.

Mori, M., Aihara, M., Kume, K., Hamanoue, M., Kohsaka, S., & Shimizu, T. (1996) *J. Neurosci.* 16, 3590-3600.

Moriarty, R. M.; Zhuang, H.; Penmasta, R.; Liu, K.; Awasthi, A. K.; Tuladhar, S. M.; Rao, M. S.C.; Singh, V. K. Inversion of configuration of a-trisubstituted (neopentyl) type secondary alcohols, *Tetrahedron Lett.* 1993, 34, 8029-8032.

Nagase, T.; Ishii, S.; Shindou, H.; Ouchi, Y.; Shimizu, T. Airway hyperresponsiveness in transgenic mice overexpressing platelet activating factor receptor is mediated by an atropine-sensitive pathway. *Am. J. Respir. Crit. Care Med.* 2002, 165, 200-205.

Nakanishi, K. (1967) *Pure Appl. Chem.* 14, 89-113 and references therein.

Nakanishi, K., Habaguchi, K., Nakadaira, Y., Woods, M. C., Maruyama, M., Major, R. T., Alauddin, M., Patel, A. R., Weinges, K., & Bäher, W. (1971) *J. Am. Chem. Soc.* 93, 3544-3546.

Nassal, M. (1983) *Liebigs Ann. Chem.* 1510-1523.

Nassal, M. (1984) *J. Am. Chem. Soc.* 106, 7540-7545.

Okabe, K., Yamada, K., Yamamura, S., & Takada, S. (1967) *J. Chem. Soc. C,* 2201-2206.

Oken, B. S., Storzbach, D. M., & Kaye, J. A. (1998) *Arch. Neurol.* 55, 1409-1415.

Park, P.-U., Pyo, S., Lee, S.-K., Sung, J. H., Kwak, W. J., Park, H.-K., Cho, Y.-B., Ryu, G. H., & Kim, T. S. (1996) U.S. Pat. No. 5,541,183. See, also, U.S. Pat. No. 5,466,829.

Perry, S. W., Hamilton, J. A., Tjoelker, L. W., Dbaibo, G., Dzenko, K. A., Epstein, L. G., Hannun, Y., Whittaker, J. S., Dewhurst, S., & Gelbard, H. A. (1998) *J. Biol. Chem.* 273, 17660-17664.

Pietri, S.; Liebgott, T.; Finet, J.-P.; Culcasi, M.; Billottet, L.; Bernard-Henriet, C. Synthesis and biological studies of a new ginkgolide C derivative: evidence that the cardioprotective effect of ginkgolides is unrelated to PAF inhibition. *Drug. Dev. Res.* 2001, 54, 191-201.

Pietri et al., PCT International Publication WO 99/52911.

Polich, J. & Gloria, R. (2001) *Hum. Psychopharmacol. Clin. Exp.* 16, 409-416.

Prescott, S. M., Zimmerman, G. A., Stafforini, D. M., & McIntyre, T. M. (2000) *Annu. Rev. Biochem.* 69, 419-445.

Rigney, U., Kimber, S., & Hindmarch, I. (1999) *Phytother. Res.* 13, 408-415.

Shindou, H., Ishii, S., Uozumi, N., & Shimizu, T. (2000) *Biochem. Biophys. Res. Commun.* 271, 812-817.

Shukla, S. D. (1996) *Biomembranes* 2B, 463-479.

Singh, M.; Saraf, M. K. Platelet-activating factor: a new target site for the development of nootropic agents. *Drug. Future,* 2001, 26, 883-888.

Smart, B. E. Fluorine substituent effects (on bioactivity) *J. Fluor. Chem.* 2001, 109, 3-11.

Smith, P. F., Maclennan, K., & Darlington, C. L. (1996) *J. Ethnopharmacol.* 50, 131-139.

Smith, P. F. & Maclennan, K. (1999) *Curr. Opin. Anti-Inflamm. Immuno. Invest. Drugs* 1, 205-218.

Søholm, B. (1998) *Adv. Nat. Ther.* 15, 54-65.

Stough, C., Clarke, J., Lloyd, J., & Nathan, P. J. (2001) *Int. J. Neuropsychopharmacol.* 4, 131-134.

Strømgaard, K.; Saito, D. R.; Shindou, H.; Ishii, S.; Shimizu, T.; Nakanishi, K. Ginkgolide derivatives for photolabeling studies: preparation and pharmacological evaluation. *J. Med. Chem.* 2002, 45, 4038-4046.

Suehiro, M; Strømgaard, K.; Nakanishi, K. Unpublished results.

Taniguchi, H.; Iwasaka, T.; Takayama, Y.; Sugiura, T.; Inada, M. Role of Platelet Activating Factor in pulmonary edema after coronary ligation in dogs. *Chest* 1992, 102, 1245-1250.

Teng, B.-P. (1997) U.S. Pat. No. 5,599,950. See, also, GB 2 288 599 A.

Tsuneyuki Ebara; Katsuyuki Miura; Takeshi Matsuura; Masahito Imanishi; Yoshiki Yamano; Shokei Kim and Hiroshi Iwao Role of Platelet Activating Factor and Prostanoids in Hemodynamic Changes in Rat Experimental End toxic Shock *Jpn. J. Pharmacol.* 1996, 71(3): 247-253

Vasella et al., U.S. Pat. No. 6,143,725.

Watanabe, M. H., Wolffram, S., Ader, P., Rimbach, G., Packer, L., Maguire, J. J., Shultz, P. G., & Gohil, K. (2001) *Proc. Natl. Acad. Sci. USA* 98, 6577-6580.

Weinges, K. Hepp, M., & Jaggy, H. (1987) *Liebigs Ann. Chem.* 521-526.

Weinges, K. & Schick, H. (1991) *Liebigs Ann. Chem.* 81-83.

http://www.herbs.org/greenpapers/ginkgo.htm

What is claimed is:

1. A compound having the structure:

wherein $R_1$ is H or OH, wherein $R_3$ is H or OH; and wherein $R_2$ is Cl or I and $R_4$ is H, $(C_1$-$C_{10})$ alkyl, $(C_2$-$C_{10})$ alkenyl, $(C_2$-$C_{10})$ alkynyl, -A-Ar, -A-Z-Ar, —$SO_2$—Ar, or -A-$NR_6$, or —$R_6$, where A is $(C_1$-$C_8)$ alkyl, $(C_2$-$C_8)$ alkenyl, $(C_2$-$C_8)$alkynyl, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may be unsubstituted or substituted by one to five substituents selected from the group consisting of hydrogen, halogen, a hydroxy group, a carboxylic acid group, substituted or unsubstituted $(C_1$-$C_{10})$ alkyl, $(C_2$-$C_{10})$ alkenyl, $(C_2$-$C_{10})$ alkynyl, $(C_1$-$C_{10})$ haloalkyl, $(C_1$-$C_{10})$ alkoxy, $(C_2$-$C_{10})$ alkenyloxy, $(C_2$-$C_{10})$ alkynyloxy, $(C_1$-$C_{10})$ haloalkoxy, a phenyl group, a phenoxy group, an aralkyl group, an aralkyloxy group, a substituted phenyl group, a substituted phenoxy group, a substituted aralkyl group, a substituted aralkyloxy group, —$COR_6$, —$CONR_6R_6$, —$CO_2R_6$, —NH-$COR_6$, —NH(OH), —N(OH)$COR_6$, —$CH_2OR_6$, —$OCH_2CO_2R_6$, —$CH_2SR_6$, —$CH_2NR_6R_6$, —$SR_6$, —$OSR_6$, —$NR_6R_6$, —$NR_6SO_2R_6$, where $R_6$ is hydrogen, $(C_1$-$C_{10})$ alkyl, $(C_3$-$C_{10})$ cycloalkyl, —$SCX_3$ in which X is a halogen, —CN, —$NO_2$ or -Z-A-Z'- in which Z and A are as defined above and Z' represents carbon, oxygen, sulfur, or nitrogen;

or wherein $R_2$ is OH or halogen and $R_4$ is $(C_2-C_{10})$ alkenyl, $(C_2-C_{10})$ alkynyl, -A-Ar, -A-Z-Ar, or -A-$NR_6$ where A is $(C_2-C_8)$ alkenyl, or $(C_2-C_8)$alkynyl, which is unsubstituted or substituted by a straight or branched alkyl chain group having 1 to 5 carbon atoms where $R_6$ is hydrogen, $(C_1-C_{10})$ alkyl, $(C_3-C_{10})$ cycloalkyl, —$SCX_3$ in which X is a halogen, —CN, —$NO_2$ or -Z-A-Z'- in which Z and A are as defined above and Z' represents carbon, oxygen, sulfur, or nitrogen;

or an optically pure enantiomer, or a tautomer, or a salt of the compound.

2. The compound of claim 1, wherein $R_2$ is a halogen and is F, Br or Cl.

3. The compound of claim 2, wherein $R_1$ is OH.

4. The compound of claim 2, wherein $R_4$ is H.

5. The compound of claim 2, wherein $R_3$ is OH.

6. The compound of claim 1, wherein $R_2$ is OH.

7. The compound of claim 6, wherein $R_1$ is OH.

8. The compound of claim 6, wherein $R_3$ is OH.

9. The compound of claim 1, wherein $R_4$ is

-A-Ar, -A-Z-Ar, —$SO_2$—Ar, or -A-$NR_6$, or —$R_6$, where A is $(C_1-C_8)$ alkyl, $(C_2-C_8)$ alkenyl, $(C_2-C_8)$alkynyl, which is unsubstituted or substituted by a straight or branched alkyl chain group having 1 to 5 carbon atoms;

Z is carbon, oxygen, sulfur or nitrogen;

Ar is a phenyl group, a pyridyl group, a naphthyl group, a pyrimidyl group, or a quinolyl group, each of which may be unsubstituted or substituted by one to five substituents selected from the group consisting of hydrogen, halogen, a hydroxy group, a carboxylic acid group, substituted or unsubstituted $(C_1-C_{10})$ alkyl, $(C_2-C_{10})$ alkenyl, $(C_2-C_{10})$ alkynyl, $(C_1-C_{10})$ haloalkyl, $(C_1-C_{10})$ alkoxy, $(C_2-C_{10})$ alkenyloxy, $(C_2-C_{10})$ alkynyloxy, $(C_1-C_{10})$ haloalkoxy, a phenyl group, a phenoxy group, an aralkyl group, an aralkyloxy group, a substituted phenyl group, a substituted phenoxy group, a substituted aralkyl group, a substituted aralkyloxy group, —$COR_6$, —$CONR_6R_6$, —$CO_2R_6$, —NH$COR_6$, —NH(OH), —N(OH)$COR_6$, —$CH_2OR_6$, —$OCH_2CO_2R_6$, —$CH_2SR_6$, —$CH_2NR_6R_6$, —$SR_6$, —$OSR_6$, —$NR_6R_6$, —$NR_6SO_2R_6$, where $R_6$ is hydrogen, $(C_1-C_{10})$ alkyl, $(C_3-C_{10})$ cycloalkyl, —$SCX_3$ in which X is a halogen, —CN, —$NO_2$ or -Z-A-Z'- in which Z and A are as defined above and Z' represents carbon, oxygen, sulfur, or nitrogen.

10. The compound of claim 9, wherein $R_4$ is -A-Ar, where A is $(C_1-C_8)$ alkyl, $(C_2-C_8)$ alkenyl, $(C_2-C_8)$alkynyl, which is unsubstituted or substituted by a straight or branched alkyl chain group having 1 to 5 carbon atoms;

and Ar is a substituted phenyl group.

11. The compound of claim 10, wherein A is a $C_1$ alkyl.

12. The compound of claim 10, wherein Ar is substituted with a substituted $C_1$ alkoxy.

13. The compound of claim 12, wherein the substituted $C_1$ alkoxy is substituted with a substituted aromatic.

14. The compound of claim 13, wherein the substituted aromatic is substituted with a halogen.

15. The compound of claim 14, wherein $R_1$ and $R_3$ are OH.

16. A pharmaceutical composition comprising a therapeutically effective amount of the compound of claim 1 and a pharmaceutically acceptable carrier.

17. A process for producing the compound of claim 2 comprising:
 a) dissolving 7-trifluromethanesulfonyloxy ginkgolide B and tetrabutylammonium fluoride hydrate in $CH_3CN$;
 b) removing the $CH_3CN$ and partitioning the product between HCl and EtOAc so as to form an organic phase; and
 c) purifying the organic phase so as to produce the compound.

18. A process for producing the compound of claim 6 comprising:
 a) dissolving ginkgolide B or ginkgolide C in THF;
 b) contacting the product of step a) with benzophenone;
 c) contacting the product of step b) with HCl;
 d) extracting the product of step c) with EtOAc and washing with saturated $NH_4Cl$;
 e) drying the product of step d) with $MgSO_4$;
 f) purifying the product of step e) with flash column chromatography with $CHCl_3$/MeOH so as to produce the compound.

19. A method of inhibiting activation of the platelet-activating factor receptor (PAFR) which comprises contacting the PAFR with the compound of claim 1 so as to thereby inhibit activation of the PAFR.

* * * * *